US007736909B2

(12) United States Patent
Kodadek

(10) Patent No.: US 7,736,909 B2
(45) Date of Patent: Jun. 15, 2010

(54) METHODS AND COMPOSITIONS COMPRISING CAPTURE AGENTS

(75) Inventor: Thomas Kodadek, Dallas, TX (US)

(73) Assignee: Board of Regents, the University of Texas System, Austin, TX (US)

(*) Notice: Subject to any disclaimer, the term of this patent is extended or adjusted under 35 U.S.C. 154(b) by 1388 days.

(21) Appl. No.: 10/754,457

(22) Filed: Jan. 9, 2004

(65) Prior Publication Data

US 2004/0161798 A1  Aug. 19, 2004

Related U.S. Application Data

(60) Provisional application No. 60/438,805, filed on Jan. 9, 2003.

(51) Int. Cl.
*G01N 33/543* (2006.01)
(52) U.S. Cl. ....................................... 436/518
(58) Field of Classification Search ............... 436/8, 436/578, 523–527, 518; 435/4, 7.1, 292
See application file for complete search history.

(56) References Cited

U.S. PATENT DOCUMENTS

| | | | | |
|---|---|---|---|---|
| 4,789,628 | A | 12/1988 | Nayak | 435/7 |
| 5,011,771 | A * | 4/1991 | Bellet et al. | 435/7.94 |
| 5,149,626 | A | 9/1992 | Fleming | 435/7.9 |
| 5,705,614 | A * | 1/1998 | Ring | 530/387.3 |
| 6,153,596 | A * | 11/2000 | Liotta et al. | 514/44 |
| 6,197,599 | B1 * | 3/2001 | Chin et al. | 436/518 |
| 6,297,059 | B1 | 10/2001 | Song et al. | 436/501 |
| 6,306,643 | B1 | 10/2001 | Gentalen et al. | 435/287.2 |
| 6,344,330 | B1 | 2/2002 | Ellman et al. | 435/7.1 |
| 6,344,334 | B1 | 2/2002 | Ellman et al. | 435/7.1 |
| 6,365,418 | B1 | 4/2002 | Wagner et al. | 436/518 |
| 6,406,921 | B1 | 6/2002 | Wagner et al. | 436/518 |
| 6,465,183 | B2 | 10/2002 | Wolber | 435/6 |
| 6,465,430 | B1 * | 10/2002 | Dower et al. | 514/13 |
| 6,800,728 | B2 * | 10/2004 | Schwartz | 530/345 |
| 7,091,046 | B2 * | 8/2006 | Monforte | 436/173 |
| 7,504,364 | B2 | 3/2009 | Carlson | 506/30 |
| 7,504,365 | B2 | 3/2009 | Carlson | 506/30 |
| 2002/0006620 | A1 | 1/2002 | Short | 435/6 |
| 2002/0018749 | A1 * | 2/2002 | Hudson et al. | 424/1.49 |
| 2002/0022227 | A1 | 2/2002 | Short | 435/6 |
| 2002/0098493 | A1 | 7/2002 | Nathan | 435/6 |
| 2002/0137106 | A1 | 9/2002 | Leung et al. | 435/7.9 |
| 2004/0171068 | A1 * | 9/2004 | Wehland et al. | 435/7.1 |

FOREIGN PATENT DOCUMENTS

| | | |
|---|---|---|
| EP | 0268296 | 5/1988 |
| EP | 0317804 | 5/1989 |
| EP | 0491362 | 6/1992 |
| EP | 0586618 | 7/1997 |
| EP | 0818467 | 1/1998 |
| WO | WO 01/69258 | 9/2001 |
| WO | WO 02/31510 | 4/2002 |
| WO | WO 02/063299 | 8/2002 |
| WO | WO 03/074990 | 9/2003 |

OTHER PUBLICATIONS

Bachhawat-Sikder and Kodadek, "Mixed-element capture agents: a simple strategy for the construction of synthetic, high-affinity protein capture ligands," *J. Am. Chem. Soc.*, 125:9550-9551, 2003.
Burkoth et al., "Toward the synthesis of artificial proteins: the discovery of an amphiphilic helical peptoid assembly," *Chem. Biol.*, 9:647-654, 2002.
Cussac et al., "A Sos-derived peptidimer blocks the Ras signaling pathway by binding both Grb2 SH3 domains and displays antiproliferative activity," *FASEB J.*, 13:31-38, 1999.
Fancy and Kodadek, "Chemistry for the analysis of protein-protein interactions: rapid and efficient cross-linking triggered by long wavelength light," *Proc. Natl. Acad. Sci., USA*, 96:6020-6024, 1999.
Figliozzi et al., "Synthesis of N-substituted glycine peptoid libraries," *Methods Enzymol.*, 267:437-447, 1996.
Hajkuk et al., "Discovering high-affinity ligands for proteins," *Science*, 278(5337):497-499, 1997.
Han and Kodadek, "Peptides selected to bind the Gal80 repressor are potent transcriptional activation domains in yeast," *J. Biol. Chem.*, 275(20):14979-14984, 2000.
Kiessling et al., "Synthetic multivalent ligands in the exploration of cell-surface interactions," *Curr. Opin. Chem. Biol.*, 4:696-703, 2000.
Kirshenbaum et al., "Sequence-specific polypeptoids: a diverse family of heteropolymers with stable secondary structure," *Proc. Natl. Acad. Sci., USA*, 95:4303-4308, 1998.
Kitov et al., "Shiga-like toxins are neutralized by tailored multavalent carbohydrate ligands," *Nature*, 403:669-672, 2000.
Kodadek, "Protein microarrays: prospects and problems," *Chem. Biol.*, 8:105-115, 2001.
Kodadek, "Development of protein-detecting microarrays and related devices," *Trends Biochem. Sci.*, 27(6):295-300, 2002.
Koehler et al., "Discovery of an inhibitor of a transcription factor using small molecule microarrays and diversity-oriented synthesis," *J. Amer. Chem. Soc.*, 125:8420-8421, 2003.
Kuruvilla et al., "Dissecting glucose signaling with diversity-oriented synthesis and small-molecule microarrays," *Nature*, 416:653-657, 2002.
Ladbury et al., "Measurement of the binding of tyrosyl phosphopeptides to SH2 domains: a reappraisal.," *Proc. Natl. Acad. Sci., USA*, 92:3199-3203, 1995.
Maly et al., "Combinatorial target-guided ligand assembly: identification of potent subtype-selective c-Src inhibitors," *Proc. Natl. Acad. Sci., USA*, 97:2419-2424, 2000.
Melcher and Xu, *EMBO J.*, "Gal80-Gal80 interaction on adjacent Gal4p binding sites is required for complete GAL gene repression," 20:841-851, 2001.
Merritt et al., "Characterization and crystal structure of a high-affinity pentavalent receptor-binding inhibitor for cholera toxin and *E. coli* heat-labile enterotoxin," *J. Amer. Chem. Soc.*, 124:8818-8824, 2002.

(Continued)

*Primary Examiner*—Ann Y Lam
(74) *Attorney, Agent, or Firm*—Fulbright & Jaworski, L.L.P.

(57) ABSTRACT

The present invention relates to methods and compositions for detecting a substance using mixed or multiple element capture agents (MECA). The affinity of a MECA for a target is produced by the concomitant binding of at least two low to moderate affinity capture agents providing a high affinity interaction with a capture target.

20 Claims, 26 Drawing Sheets

OTHER PUBLICATIONS

Olejniczak et al., "Stromelysin inhibitors designed from weakly bound fragments: effects of linking and cooperativity," *J. Amer. Chem. Soc.*, 119:5828-5832, 1997.

Oliver et al., "Multiplexed Analysis of Human Cytokines by Use of the FlowMetrix System," *Clinical Chemistry*, 44:2057-2060, 1998.

Schreiber, "Target-oriented and diversity-oriented organic synthesis in drug discovery," *Science*, 287(5460), 1964-1969, 2000.

Shuker et al., "Discovering high-affinity ligands for proteins: SAR by NMR," *Science*, 274:1531-1534, 1996.

Stoll et al., "Chalcone derivatives antagonize interactions between the human oncoprotein MDM2 and p53," *Biochemistry*, 40:336-344, 2001.

Terskikh et al., "'Peptabody': a new type of high avidity binding protein," *Proc. Natl. Acad. Sci., USA*, 94:1663-1668, 1997.

Thoma et al., "Nanomolar E-selectin inhibitors: 700-fold potentiation of affinity by multivalent ligand presentation," *J. Amer. Chem. Soc.*, 123:10113-10114, 2001.

Vignali, "Multiplexed particle-based flow cytometric assays," *J. of Immunol. Methods*, 243:243-255, 2000.

Woodbury and Vinton., "Methods of screening combinatorial libraries using immobilized or restrained receptors," *J. Chromatogr B Biomed. Sci. Appl.*, 725:113-137, 1999.

* cited by examiner

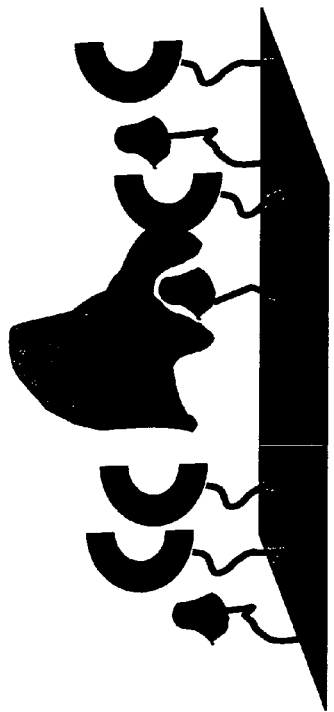
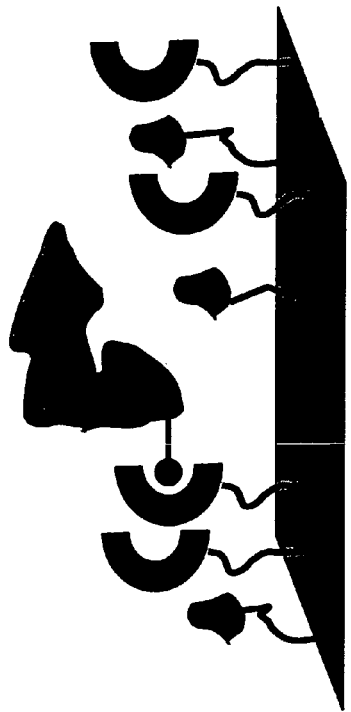
FIG. 5

G80BP-A: YDQDMQNNTFDDLFWKEGHR
G80BP-B: NEDWERDDQNPWDKLWMNRA
GAL4 AD: MDQTAYNAFGITTGMFNTTTMDDVYNYLFDDEDT

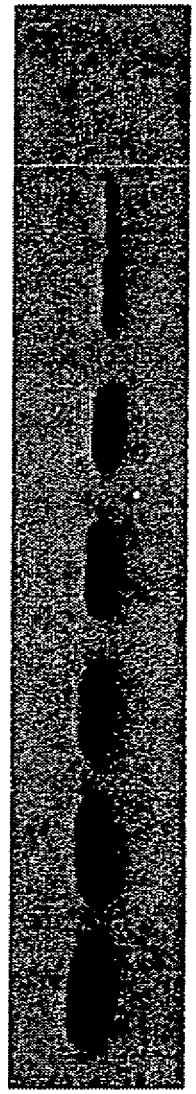
FIG. 8

(1) Npip-Npip-Nbsa-Nser-Nlys-Npip-Nbsa-Nlys
(2) Nbsa-Npip-Nlys-Nser-Nbsa-Nser-Nbsa-Npip
(3) Nbsa-Nlys-Npip-Nser-Nbsa-Nser-Nall-Nlys
(4) Nbsa-Nbsa-Nall-Nser-Nall-Npip-Nall-Npip
(5) Nall-Nall-Nbsa-Nser-Nlys-Nbsa-Nser-Nall
(6) Nlys-Nlys-Nser-Nser-Npip-Nall-Nbsa-Nser
(7) Nlys-Nlys-Nser-Nser-Npip-Nbsa-Nall-Nbsa
(8) Nall-Nlys-Nser-Nser-Nbsa-Nser-Nlys-Nlys
(9) Npip-Nlys-Nall-Nser-Nbsa-Nser-Nbsa-Nall
(10) Nbsa-Nlys-Npip-Nser-Nbsa-Nser-Nall-Nlys

FIG. 13

(A)
- Nleu-Nbsa-Nlys-Napp-Ntrp-Nleu
- Nmba-Nleu-Napp-Nmba-Nbsa-Nffa
- Nlys-Nmea-Ntrp-Napp-Nleu-Nleu
- Nmea-Npip-Nmba-Nffa-Napp-Nleu
- Nleu-Nlys-Nmea-Nleu-Ntrp-Nmea
- Ntrp-Nffa-Ntrp-Nbsa-Napp-Npip
- Nffa-Nleu-Nmea-Npip-Nlys-Nleu
- Npip-Nmea-Nmba-Napp-Nleu-Napp
- Napp-Nmea-Nmba-Npip-Nffa-Nffa
- Nleu-Npip-Nbsa-Nmea-Nmba-Nmea (B)

```
                      SEQUENCE LISTING

<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ccgcgggatc cgcctgttct ctcccacact gtcg                                  34

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gaattcaagc ctttagtggt gatggtggtg atgggctgct ggttgcccca tgcccacac      59

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Tyr Asp Gln Asp Met Gln Asn Asn Thr Phe Asp Asp Leu Phe Trp Lys
 1               5                  10                  15
```

```
Glu Gly His Arg
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Asp Leu Gln Arg Asp Thr Asn Lys Gly Phe His Glu Met Phe Asp Trp
 1               5                  10                  15

Asp Tyr Gln Asn
            20

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ser His Ser Thr Ala Arg Gly Glu Gln Glu Arg Ala Ala Val Tyr Leu
 1               5                  10                  15

Trp Phe Thr Tyr Asp His Arg Ser Glu Arg
            20                  25

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Ser Glu Phe Ala Arg Asp Leu Ala Tyr Gly Glu Tyr Ser Gln His Val
 1               5                  10                  15

Arg Trp Thr His Glu Arg Ala Thr Ser Arg
            20                  25

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Arg Gly Trp Val Glu Ile Cys Ala Ala Asp Asp Tyr Gly Arg Cys Leu
 1               5                  10                  15

Thr Glu Ala Gln
            20

<210> SEQ ID NO 8
<211> LENGTH: 20
<212> TYPE: PRT
<213> ORGANISM: Artificial Sequence
<220> FEATURE:
```

-continued

<223> OTHER INFORMATION: Description of Artificial Sequence:  Synthetic
      Peptide

<400> SEQUENCE: 8

Cys Gln Glu Cys Asp Tyr Trp Arg Glu Val Arg Gly Ala Asp Ala Leu
1               5                   10                  15

Ile Thr Gly Ala
            20

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Pro Leu Ser Gln Glu Thr Phe Ser Asp Leu Trp Lys Leu Leu Pro Glu
1               5                   10                  15

Asn Asn Val

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Asn Val Lys Trp Leu Asp Pro Asn Gln Glu Leu Pro Ser Phe Leu Thr
1               5                   10                  15

Ser Leu Glu

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Ser Val Pro Gly Ser Val Ser Trp Phe Glu Phe Trp Ser Ala Val Asp
1               5                   10                  15

Ala Val Glu Thr
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Phe Ser Ala Ser Phe Thr Glu Val Val Asp Ala Gly Trp Val Ser Pro
1               5                   10                  15

Trp Ser Val Glu
            20

METHODS AND COMPOSITIONS COMPRISING CAPTURE AGENTS

This application claims priority to U.S. Provisional Patent Application Ser. No. 60/438,805, filed on Jan. 9, 2003, which is incorporated herein by reference in its entirety.

This invention was made with government support under grant numbers R21CA932701 and R21CA093287 awarded by the National Cancer Institute, contract No. NO1-HV-28185 awarded by the National Institutes of Health, and grant number I-1299 awarded by the Welch Foundation. The government has certain rights in the invention.

BACKGROUND OF THE INVENTION

1. Field of the Invention

The present invention relates generally to the fields of chemistry, molecular biology, and diagnostics. More particularly, it concerns methods and compositions for obtaining a high affinity synthetic capture agent for a molecular or biomolecular target by co-immobilizing at least two low-to-moderate affinity ligands on a suitable surface. Such a high affinity synthetic capture agent is referred to as a mixed element capture agent (MECA). MECAs will be of great utility in the construction of medical diagnostic devices.

2. Description of Related Art

There is great interest in the development of techniques with which to monitor the levels, post-translational modification states and activities of large numbers of proteins simultaneously. One approach is to construct protein-detecting arrays (Kodadek, 2001; Kodadek, 2002), akin to the DNA microarrays used widely in genomics research. Such devices may be comprised of many different protein-binding molecules arrayed on a suitable surface in a defined pattern, each capable of recognizing its target protein with high affinity and high specificity. These high affinity and high specificity protein-binding molecules or ligands are referred to as capture agents. An alternative format is to immobilize protein-binding molecules on encoded beads (Vignali, 2000; Oliver et al., 1998). A significant challenge in the development of such technology is the isolation of large numbers of protein-binding compounds with a sufficiently high binding affinity and specificity to be useful in the capture of particular proteins from a complex mixture.

Most of the effort in this area has focused on the use of macromolecular biomolecules as capture agents, such as antibodies (Eggers et al., 1998; Hunag et al., 2002; Huang, 2001; Wiese et al., 2001; Huang et al., 2001; Walter et al., 2000; and Haab et al., 2001), nucleic acids (particularly RNA) aptamers (Osborne et al., 1997; Jhaveri et al., 2000; Famlouk and Jenne, 1998; Seethsnunan et al., 2001; and Vaish et al., 2002) and protein-RNA fusions (Roberts and Szostak, 1997; Wilson et al., 2001; and Colas et al., 1996).

Protein-binding molecules can be readily isolated from combinatorial libraries or other types of large compound collections using a number of methods. Unfortunately, small molecules, peptides, peptidomimetics and other synthetically accessible compounds rarely bind to their target protein with an affinity comparable to that of a good antibody (equilibrium dissociation constant $(K_D) \leq 10^{-9}$ M). Instead, small molecule/protein complexes generally exhibit $K_D$s in the μM range, with the exception of molecules optimized through extensive medicinal chemistry efforts or natural selection. This modest affinity is insufficient to capture low abundance proteins from complex mixtures. In addition, the relatively rapid dissociation rates of such complexes result in the loss of most of the bound capture target during the inevitable washing steps required to minimize non-specific "background" binding of high abundance or "sticky" proteins. Therefore, a central problem in applying organic chemistry to the development of protein-detecting microarrays is obtaining higher affinity synthetic ligands in a high-throughput fashion.

In the case of pharmaceuticals, optimization of a lead compound is generally achieved through a tedious and labor-intensive process in which hundreds of relatives of the lead molecule are synthesized and evaluated for activity. It is not possible to apply this approach on a scale where ligands are required for hundreds or even thousands of proteins. One potential "shortcut" in the path from low to high affinity agents is to employ multivalency. For example, coupling two or more modest affinity protein ligands with an appropriate linker can provide a high affinity bivalent or multivalent ligand (Shukery et al., 1996; Olejniczak et al., 1997; Thorn et al., 2001; Terskikh et al., 1997; Merritt et al., 2002; Kitov et al., 2000; Kiessling et al., 2000 and Cussac et al., 1999). Unfortunately, linker optimization can be time consuming, and most approaches to this problem are unsuitable for high-throughput proteomics applications (see Maly et al., 2000, for an exemplary combinatorial approach). Thus, there remains a need for rapid, selective and high-affinity compositions and methods for rapidly providing a high affinity synthetic capture agent.

SUMMARY OF THE INVENTION

This invention describes how two low to modest affinity binding elements can be combined on a surface in such a way as to form a high affinity capture agent without any requirement for the design or discovery of a suitable linker to connect the two ligands. Various embodiments of the invention include novel capture agent compositions and methods for obtaining these types of mixed element capture agents (MECAs) even if only a single binding element is known for a given molecular target. In certain embodiments, methods and compositions of the invention include a plurality of low to moderate affinity binding elements distributed on a surface of and operatively coupled to a support, wherein concomitant binding of a first target molecule to two of the low-to-moderate affinity binding elements results in a high affinity interaction with the first target molecule producing a mixed or multiple element capture agent (MECA).

In certain embodiments, MECAs are comprised of two or more binding elements that have been previously demonstrated to bind to the target molecule, for example a protein, with low to modest affinity (defined as an equilibrium dissociation constant ($K_D$) between $10^{-3}$ M and $10^{-8}$ M). The other stipulation is that these binding elements do not compete for binding to the target molecule. In certain embodiments, these low to modest affinity binding elements may be peptides, peptoids or other peptide-like oligomers. The crux of the invention is that if two or more such low-to-moderate affinity binding elements are immobilized (covalently or non-covalently) at high density on a suitable surface, then some fraction of the possible pairs of molecules on the surface will have an appropriate geometry relative to one another to bind the target molecule cooperatively. In other words, the surface will provide a "library" of suitable linker geometries. This allows for the creation of a bidentate (or multidentate) capture agent that will retain the target molecule with high affinity and specificity without any effort expended in linker discovery, design and optimization.

The individual binding elements that make up a MECA may be combined on the surface in a number of ways. Either two or more binding elements can be added simultaneously to a suitably functionalized surface in order to achieve a statistical distriubution of the two or more binding elements on the surface, or two or more binding elements may be operatively coupled to one another prior to immobilization. In the latter case, a single chimeric species, containing two binding elements, would then be attached to the surface, providing the highest possible density of immobilized species. This pre-linkage could consist of linear or branched fusions of the ligands or coupling them to a variety of scaffolds. Importantly, these couplings would not involve any linker design, discovery or optimization. In various embodiments of the invention, a support is a cross-linked polymer bead or a chemically-modified glass slide. Samples that could be analyzed with these immobilized capture agents include, but are not limited to, a cell lysate, a blood sample, a sputum sample, or a urine sample. Samples may include various other biological and non-biological materials. A target molecule may be any molecule or substance to which a MECA may bind including, but not limited to, polypeptides. Targets could also include assemblages of molecules, such as multi-protein complexes, sub-cellular compartments (nucleus, etc.) or even whole cells. A target polypeptide may also be a proteolytic fragment or part of polypeptide or may carry post-translational modifications. Post-translational modification includes, but is not limited to phosphorylation, glycosylation, ubiquitylation, SUMOylation (Sternsdorf et al., 1999) and the like.

In various embodiments, compositions may comprise a third and a fourth low-to-moderate affinity binding element that bind a second target molecule (i.e., a second MECA), the third and fourth low affinity binding element are distributed on a surface of, and operatively coupled to, a support, wherein concomitant binding of the second target molecule to the third and fourth low affinity binding elements results in a high affinity interaction with the second target molecule. The third and fourth low affinity binding elements typically have a distinct binding specificity as compared to each other. The third and fourth low to moderate affinity binding elements (second MECA) will typically have distinct binding specificity as compared to a first and second low affinity binding elements (first MECA). In other words, the second MECA will capture a different target molecule or assemblage of molecules than the first MECA. In various embodiments, a composition may include 1, 2, 3, 4, 5, 6, 7, 8, 9, 10, 100, 1000 or more MECAs that can be arranged in an addressable array, wherein each MECA or a group of MECAs may be segregated from other MECAs or groups of MECAs.

Once a target molecule or assemblage of molecules is captured by a MECA (or multiple targets are captured on an array of MECAs), these binding events can be detected and quantified by a variety of methods including, but not limited to spectroscopy, mass spectrometry, fluorescense, magnetic resonance imaging surface plasmon resonance and the like.

In certain embodiments, contemplated methods include analyzing the modification of a protein in a sample. The method may include exposing the protein-containing sample to one or more MECAs, which would be designed to discriminate between different modified forms of the protein. This would be achieved by co-immobilizing one or more low-to-modest affinity binding elements that recognize the protein and which are relatively insensitive to the modification, with one or more low-to-modest affinity binding elements that recognize the modification (for example a ubiquitin molecule or phosphoserine) but which is relatively insensitive to the identify of the polypeptide. This type of MECA would have a high affinity for only the protein of interest decorated with the post-translational modification of interest, whereas other proteins modified in this way or the target protein decorated with other types of modifications would evince only low-to modest affinity binding to the MECA.

In another embodiment, a specific multi-protein complex could be captured by a MECA comprised of ligands for two or more different proteins in the complex.

Another embodiment of the invention includes methods of discovering MECAs when only a single low-to-modest affinity ligand for a given molecular target is available. This is done by coupling the known low-to-moderate affinity binding element to each molecule in a combinatorial library of oligomers. The library is screened on a suitable surface (modified polystyrene bead, chemically modified glass slide, etc.) under conditions that demand a high affinity capture event to retain the target protein on the surface. This procedure will allow the high affinity, cooperative binding of the lead compound and a library-derived molecule to the target molecule. Capture agents derived via this method are described below as chimeric mixed element capture agents. The oligomer may be a peptide or peptide derivative, nucleic acid or nucleic acid derivative, or an oligomer comprising a plurality of heterogeneous monomer units. A peptide derivative may include one or more non-natural amino acids and may include one or more peptoid monomers. In certain aspects, the binding element or ligand may be a nucleic acid, amino acid, peptide, steroid, inorganic molecule or organic molecule. The ligand may be operatively coupled to a terminal or internal position in an oligomer.

Certain embodiments include compositions for assessing the presence of at least a first target molecule in a sample comprising a plurality of low-to-moderate affinity binding elements distributed on a surface of, and operatively coupled to a support, wherein concomitant binding of the first target molecule to two or more of the binding elements results in a high affinity interaction with the first target molecule. In certain aspects the binding element are known low to moderate affinity binding elements of a target molecule. The binding elements may be, but are not limited to peptides, peptoids (N-substituted oligoglycines) or other peptide-like oligomers. In further embodiments, the plurality of binding elements comprises at least a first and a second binding element having distinct binding specificity for a target molecule as compared to each other. The first binding element may be operatively coupled to the second binding element. A spacer may be operatively coupled to the first binding element, the second binding element or both the first and second binding element. The second binding element may be an oligomer. The oligomer may be, but is not limited to a peptide or peptide derivative. A peptide derivative or a peptide like molecule is comprised of one or more non-natural amino acid or analogous molecule. The peptide derivative may be comprised of one or more peptoid monomers. A first binding element may be a nucleic acid, peptide, steroid, inorganic molecule or organic molecule. In certain embodiments, one or more first binding element may be operatively coupled to a terminal and/or internal monomer of the oligomer or second binding element.

In still further embodiments of the invention a sample may be an environmental sample, a cell lysate, a blood sample, a sputum sample or a urine sample. The sample may include one or more target molecules. A target molecule may a biological molecule or metabolite. A biological molecule is molecule produced or utlzed by an organism. An organism includes, but is not limited to humans, mammals, pathogens, microbes, bacteria, fungi, virus, prokaryotes and eukaryotes. The target molecule may be a polypeptide. The polypeptide may be modified. Modification includes, but is not limited to phosphorylation, SUMOylation or ubiquitylation. A target molecule may or may not be coupled to a detectable label.

The binding elements are typically distributed randomly on the surface of the support. A support may be a cross-linked polymer bead or a chemically-modified glass slide.

In still further embodiments, the composition may include at least a third and a fourth low-to-moderate binding element that bind a second target molecule, the third and fourth binding element distributed on a surface of, and operatively coupled to, the support, wherein concomitant binding of the second target molecule to the third and fourth binding elements results in a high affinity interaction with the second target molecule. The third and fourth low affinity binding elements may have distinct binding specificity as compared to each other and/or to the first and second low affinity binding elements. The first and second low affinity binding elements may be segregated from at least the third and fourth low affinity binding elements. In certain embodiments, the first and second low affinity binding elements are segregated from the third and fourth low affinity binding elements on the surface of the support. The first and second binding elements, and the third and fourth binding elements, are typically distributed randomly on the surface of the support within their respective segregated areas.

In other embodiments, methods of determining the presence of target molecule in a sample are contemplated that comprise a) exposing the sample to a plurality of low-to-moderate affinity binding elements distributed on a surface of, and operatively coupled to a support, wherein concomitant binding of the target molecule to at least a two of the binding elements results in a specific high affinity interaction with the target molecule; and b) evaluating binding of the target molecule to the binding elements. Binding may be observed by spectroscopy. Spectroscopy may be fluorescent and/or magnetic resonance imaging spectroscopy. The binding of a protein may be compared with the binding of the unmodified protein.

Embodiments of the invention include methods of producing a chimeric binding element comprising a) providing a first low-to-moderate affinity binding element; b) providing a combinatorial library of oligomers; c) operatively coupling the first binding element to one or more members of the combinatorial library; and d) identifying a first binding element/oligomer combination with a high affinity for a target molecule, wherein at least a portion of the oligomer is a second binding element. The oligomer may be a peptide or peptide derivative. A peptide derivative is typically comprised of one or more non-natural amino acid or analogous molecule. The peptide derivative may comprise one or more peptoid monomers.

In certain embodiments, a composition for assessing the presence of at least a first target molecule in a sample comprising chimeric binding elements distributed on a surface of, and operatively coupled to a support, wherein concomitant binding of the first target molecule to two or more of the chimeric binding elements results in a high affinity interaction with the first target molecule is contemplated.

It is contemplated that any embodied method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5 illustrates an exemplary characterization of Gal80-binding peptides isolated by phage display. Gal80 is a homodimer that can also tetramerize at concentrations above 100 nM. Note that the solution binding curve shown on the left reveals that the $K_D$ of the peptide-protein complex in solution is modest 0.3 µM.

FIG. 6A illustrates a schematic representation of the assay employed to monitor the half-life of the immobilized peptide/protein complexes. FIG. 6B shows SDS-PAGE/Western blot analysis of the amount of Gal80 remaining on the peptide-coated beads following dilution. Time elapsed following dilution is indicated in part A for each tube. Lanes 10 contain samples in which the peptide-coated beads were added to the highly dilute protein solution (approx. 5 pmol) and incubated for two hours to control for protein reassociation with the beads under these conditions. Lanes 11 represent experiments using scrambled sequences attached to the beads. Lanes 12 represent experiments done with Tentagel beads lacking any peptide. Note that dissociation of the peptide/protein complex in solution occurred within seconds (data not shown).

(FIG. 7A) The amount of $His_6Gal80$ protein indicated was added to 500 µl of buffer containing 5.7 mg E. coli lysate and 2 mg of Tentagel-Gal80 bp. After incubation and washing, the amount of protein retained on the beads is shown. (FIG. 7B) Calibration blot using known amounts of purified $His_6Gal80$ protein. This figure shows that the immobilized peptide binds the Gal80 dimer with a sub-nanomolar dissociation constant.

FIGS. 8A-8B are an exemplary comparisons of the dissociation rates from immobilized peptides of monomeric and dimeric fusion constructs containing the same target protein. A protocol similar to that described for FIG. 6A was employed, except fewer time points were taken. (FIG. 8A) SDS-PAGE/western blot analysis showing the levels of dimeric GST-Mdm2 or monomeric MBP-Mdm2 remaining associated with Tentagel-Mdm2 bp after dilution for the time indicated. (FIG. 8B) A similar experiment was conducted with dimeric GST-KIX or monomeric $His_6$-KIX. Lanes 1 and 3 show the protein standards. Lanes 2 and 4 show the amount of protein remaining on the Tentagel-KIXbp1 beads immediately following the washing step. This experiment proves that the dimmers are held tightly via a two-point contact and validate the idea that two different binding elements that bind the same monomeric protein non-competitively could collaborate to bind a target protein with very high affinity.

FIG. 9A shows the beads displaying both peptides bound the Tx Red-labeled fusion protein to a 1:1 mixture of beads displaying either the simple peptide or MECA. The micrographs show that in each case, the MECA bound the labeled fusion protein with much higher affinity than the beads that displayed a single peptide. Binding studies (FIG. 9B) done by isothermal calorimetry revealed that in free solution however, the MECA binds the fusion protein only slightly (<2-fold) better than the component peptides, highlighting the importance of surface immobilization in the result shown in FIG. 9A. Presumably, the spacing between the peptides in the MECA is inappropriate for high affinity, bidentate 1:1 binding in solution.

FIG. 13 illustrates the text sequences of ten random peptoids picked from the 78,125 compound library. The sequences, were determined by automated Edman degradation.

(FIG. 15A) A photomicrograph showing a field of beads that contains the one picked as a putative "hit. " (FIG. 15B) An Edman sequencing trace of the bright bead shown in part (FIG. 15A). (FIG. 15C) The sequence of the isolated peptoid deduced from automated Edman degradation from the single bead.

FIGS. 16A-16B show characterization of the peptoid/protein complex by isothermal titration calorimetry (ITC). ITC traces for binding of Nlys-Nbsa-Nlys-Nser-Nbsa-Npip-Nbsa-Npip to: (FIG. 16A) MBP-Mdm2 and (FIG. 16B) MBP. The top panel shows the raw data whereas the bottom panel shows the integrated curve of the experimental points (solid circles) and the best fit (solid line) of the curve. The $K_D$ values derived from these data were 37 µM for the MBP-Mdm2/peptoid complex and greater than 1 mM (i.e., little or no binding) for MBP, indicating that the peptoid targets the Mdm2-derived polypeptide.

(FIG. 17A) TentaGel beads displaying Nlys-Nbsa-Nlys-Nser-Nbsa-Npip-Nbsa-Npip were incubated with 500 nM of Texas Red-labeled MBP-Mdm2 (left panel) or 500 nM Texas Red-labeled MBP (right panel). (FIG. 17B) Capture of native protein. TentaGel beads displaying the peptoid indicated were incubated with 1 µM native protein and a 1000-fold excess of E. coli extract. The protein retained was analyzed by SDS-PAGE. A Western blot using anti-Mdm2 antibody is shown. Lane 1: molecular mass standards. Lane 2: 20% of the input. Lane 3: protein retained by TentaGel beads displaying the hit Nlys-Nbsa-Nlys-Nser-Nbsa-Npip-Nbsa-Npip. Lane 4: protein retained by the control peptoid Nmba-Nbsa-Nleu-Nlys-Npip-Nmba-Nleu-Nleu. Lane 5: Protein retained by TentaGel beads lacking a displayed peptoid (bead only control).

FIGS. 18A-18C show characterization of a large peptoid library containing more than half a million compounds. (FIG. 18A) Sequences of the peptoids obtained from ten beads picked randomly from the library. (FIG. 18B) Representative Edman traces obtained from one of these beads. (FIG. 18C) HPLC traces of two hexamers (Ntrp-Nmea-Npip-Nlys-Nffa-Nmba and Nbsa-Nleu-Napp-Napp-Nffa-Nmea-Npip) that, between them, contain each of the amines employed in the construction of the library.

(FIG. 19A) Edman traces of the hit picked from the screening experiment. (FIG. 19B) Sequence of the peptoid derived from the Edman traces.

(FIG. 20A) Photomicrographs obtained after incubation of TentaGel beads displaying the putative GST-binding peptoid Nbsa-Nlys-Nbsa-Npip-Nlys (left and middle panels) or a control peptoid Npip-Nser-Nbsa-Nall-Nlys-Npip (right panel) with 500 nM Texas Red-labeled GST or 500 nM Texas Red-labeled MBP. Two percent BSA was included in each solution to reduce non-specific interactions. (FIG. 20B) Capture of native GST by TentaGel-displayed peptoid. A Western blot obtained using anti-GST antibodies is shown. Lane 1: molecular mass standards. Lane 2: 5% of the input (1 µM GST+1000 fold excess E. coli extract). Lane 3: GST retained by TentaGel-Nbsa-Nlys-Nbsa-Npip-Nlys. Lane 4: GST retained by TentaGel-displayed Nmba-Nbsa-Nleu-Nlys-Npip-Nmba-Nleu-Nleu (the control peptoid). Lane 5: GST retained by TentaGel beads without a displayed peptoid (beads only control). (FIG. 20C) Dilution experiment measuring the capture of Texas-Red-labeled protein by TentaGel-displayed Nbsa-Nlys-Nbsa-Npip-Nlys at the protein concentrations indicated. All solutions contained a 100-fold excess of E. coli extract.

(FIG. 23A Fluorescence micrograph of the "hit" bead mixed with a population of sorted library beads; (FIG. 23B) Edman trace of the chalcone-peptoid chimera from the single "hit" bead and (FIG. 23C) its structure as elucidated by Edman sequencing.

(FIG. 26A) Solution titrations of the lead peptide (left) and the chimeric binding element (right) with ubiquitin, monitored by ITC. The equilibrium dissociation constants calculated from these data are shown. (FIG. 26B) Determination of the apparent affinity of the indicated immobilized peptides for ubiquitin. The beads were incubated with the indicated amount of native ubiquitin, washed thoroughly, then probed with Texas Red-labeled anti-ubiquitin antibody. After another wash, the beads were photographed under a fluorescence microscope. (FIG. 26C) Direct comparison of beads displaying the chimeric binding element or no peptide at all (left) and beads displaying the chimeric binding element and a control peptide (right).

DESCRIPTION OF ILLUSTRATIVE EMBODIMENTS

Figure 1:
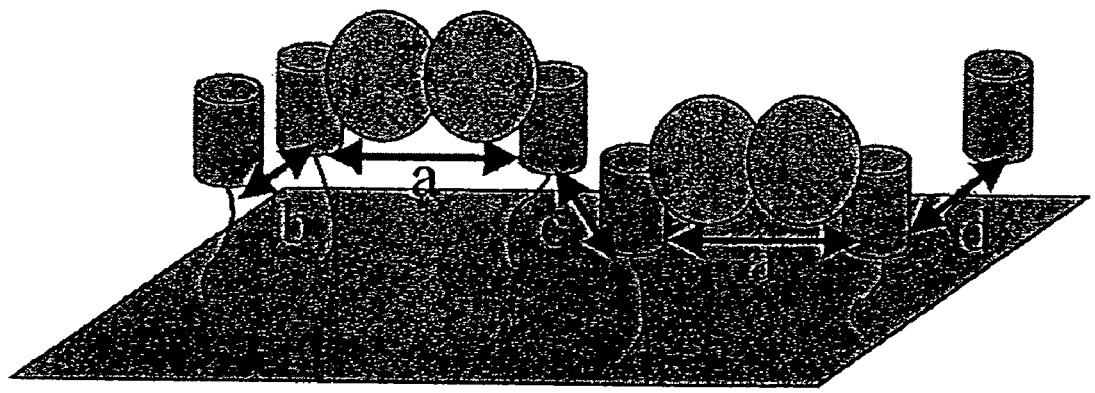
FIG. 1 is a schematic diagram of one anticipated mode of binding of a dimeric protein with a surface densely functionalized with a capture agent. Some fraction of the molecule pairs on the surface are anticipated to have the correct spacing to facilitate high-affinity, bidentate binding, as represented by length "a". Distances between molecules other than length "a," denoted as "b," "c," and "d," will not support bidentate binding.

Embodiments of the invention include compositions and methods related to the develop of high affinity mixed element capture agents (MECAs). One aspect of the invention uses a randomized distribution of binding elements to provide a mixed element capture agent (MECA). Another aspect of the invention uses a low affinity binding element in conjunction with a randomized oligomer of additional binding elements to form a chimeric binding element. A chimeric binding element may then be randomly distributed on a support to form a MECA.

I. Mixed Element Capture Agents (MECA)

As described above, there is a need for detecting substances from a variety of samples in a rapid high-throughput (HTP) format using methods and compositions comprising high-affinity and high-specificity capture agents. Most efforts in this area have focused on the use of a single high-affinity biomolecule, such as antibodies, as capture agents. Furthermore, methods for identifying a single high-affinity capture agent are time consuming and laborious. High affinity capture agents of the invention described herein include capture agents based on high affinity interactions produced by concomitant binding of two or more low to moderate affinity binding elements referred to as a mixed or multiple element capture agent (MECA). Various embodiments of the invention described herein provide methods and compositions for production of synthetic high-affinity MECA and compositions incorporating MECA(s). There are many reasons to explore synthetic, relatively low molecular mass molecules as capture agents. For example, synthetic molecules are easier to produce in large quantities with efficient quality control and can easily be tailored to allow attachment to, surfaces in a defined manner. The invention provides an easy, fast, reproducible and cost effective method of screening, detecting and characterizing various components from a variety of samples.

It is known that by properly tethering together two modest affinity, non-competitive ligands by use of a linker molecule, a high affinity chimeric ligand can be obtained. However, to achieve this, a linker with a particular length and geometry is required. Current methods to identify optimal linkers are relatively tedious and labor-intensive, grossly limiting the application of this strategy to high volume applications such as the construction of protein-detecting arrays. As described herein, a novel approach to construct high affinity capture agents without the need for linker synthesis and optimization is disclosed.

By obviating the need for linker synthesis and optimization, binding elements with modest binding affinity may be incorporated into high affinity capture agents (i.e., MECAs). This is accomplished by immobilizing binding elements on a surface that provides a library of numerous geometries between binding elements. For example, if one were to affix two protein-binding ligands on a surface in a random fashion and at high density, a fraction of the pairs of immobilized molecules would be oriented appropriately for binding to a given target. Furthermore, since this technique can use simple synthetic molecules (e.g., peptides and peptide-like compounds) one eliminates the need for the production and purification of large numbers of biological protein-binding elements, which is far more labor-intensive than small molecule synthesis. Although, in certain embodiments, recombinant peptides or polypeptides may be used as binding elements.

Typically, synthetic molecules do not bind a target with an affinity necessary for detecting substances in a sample. The composition and methods described herein may utilize a low to moderate affinity synthetic molecules to produce MECAs and provide not only time efficient, but also cost effective high-affinity capture agent compositions and detection methods. The speed with which new capture agents can be isolated and produced makes the invention an attractive pathway to diagnostic tools, especially when fast diagnosis and high throughput analysis of a sample(s) is needed.

While applicable to any kind of molecule, a particular embodiment of the invention uses synthetic molecules as binding elements. Synthetic molecules may be isolated from combinatorial libraries and generally do not have sufficient affinity as a single binding element to serve as useful capture agents (for exemplary molecules for use in combinatorial libraries see Eichler et al., 1995; Cho et al., 1999; LePlae et al., 2002; Ostergaard and Holm, 1997; and Yang et al., 1999 each of which is incorporated herein by reference). Furthermore, synthetic molecules are much cheaper and easier to make in quantity than macromolecular protein-binding compounds such as antibodies. This is one of a variety of advantages in the production of compositions and devices, as described herein, for the parallel analysis of hundreds of proteins simultaneously.

In certain embodiments, the invention describes the use of synthetic molecules as protein MECAs, which was not previously possible due to their low affinity and the tedious nature of transforming low affinity protein-binding elements into high affinity ligands. This technology will typically render small molecules the equal of good antibodies or nucleic acid aptamers in terms of binding affinity. However, small molecules are far easier to produce and to adapt as surface-immobilized protein ligands than these macromolecular species. This confers numerous advantages over current macromolecular ligand-based protein detection methods, some of which include: (a) high throughput, robust technology that makes it a frontrunner in the military, medical and research field; (b) suitable for capture of low abundance polypeptides in the sample; (c) small molecule ligands that may be used in this technology typically have the advantage of being more robust than macromolecular protein ligands or nucleic acid ligands (this gives this technology an edge over currently available technologies in large-scale production for commercialization); and (d) in addition, this technology is typically not as labor-intensive and is cost effective.

In various embodiments, methods for rapid isolation of MECA(s) for polypeptide or peptide targets or any other target molecules particularly those that can be described as an oligomer of linked monomers, such as polysaccharides or nucleic acids are contemplated. The compositions and methods described herein may be used to detect a polypeptide in a sample, via the high affinity binding of the polypeptide to two or more surface-immobilized binding elements (MECA). A binding element may be isolated from phage, peptide, and/or chemical libraries and the like.

In examples provided herein, a model system is described in which immobilized peptides are used as binding elements to form a model capture agent for homodimeric proteins. In this simplest case, there is only one type of binding element, thus technically not a mixed element capture agent, on the surface, but two identical molecules must collaborate to bind the target dimer tightly. Simple, linear peptides that exhibit modest affinities for their target proteins in solution ($K_D$s in the μM range) act as sub-nanomolar capture agents when immobilized on a surface.

In the case where the target protein is a monomer, two different, non-competitive surface-linked binding elements, i.e., a MECA, must collaborate to provide high affinity binding. In the case shown in FIGS. 9A-9B, this was achieved by co-immobilizing peptides that bind monomeric MBP and monomeric mdm2 (in the form of a single fused linear peptide, a chimeric binding element), thus providing a high affinity MECA for the efficient capture of the MBP-mdm2 model protein. The fused linear peptide is referred to as a chimeric binding element because two distinct binding elements are operatively coupled to each other. The immobilized peptide-protein complexes are shown to be long-lived, with lifetimes well in excess of what would be required for a protein-detecting application. MECAs comprised of two or more binding elements can bind any protein with high affinity, regardless of its molecularity, and is thus a completely general approach to the development of high affinity capture agents.

In various embodiments of the invention, heteromultimer or heteromeric complexes may also be bound by MECAs. Each binding element may bind the same or different component of a heteromultimer. A "heteromultimer" is defined as a higher order complex of different or heterologous molecules or substances. For instance, a heteromultimer refers to a complex of heterologous proteins. A heteromultimer may be an association of 2, 3, 4, 5, 6, 7, 8, 9, 10, or more molecules or compounds, e.g., proteins. In some instances, a component of a heteromultimer may be present one or more times within the heteromultimer. For example, A is a first protein and B is a second protein. A heteromultimer may be protein complex with a structure of (BAAB).

Various embodiments of the invention include two or more protein binding elements that bind with low to modest affinity in solution and act as tenacious capture agents when immobilized on a support. Linear peptides immobilized on beads are able to capture dimeric proteins from dilute (<1 nM protein) solutions essentially quantitatively (see FIGS. 7A-7B). Furthermore, immobilized peptide/protein complexes have been demonstrated to have kinetic half-lives of several hours. The specificity of MECA binding rivals that of a good antibody. Simple molecules isolated directly from various readily available combinatorial libraries can be used as practical capture agents for a capture target, for example, a monomeric, homodimeric or higher-order protein(s).

In certain embodiments, two low to moderate affinity, non-competing binding elements may be co-immobilized on a surface. For example, a combination of binding elements for a variety of molecules with almost any desired distance between them may be identified on a surface. Consequently, two or more binding elements will be appropriately spaced to form high-affinity binding site(s) on some fraction of the surface. One can envision that the higher the immobilized binding element density, the greater the fraction of the surface would represent high-affinity binding sites.

Figure 2:
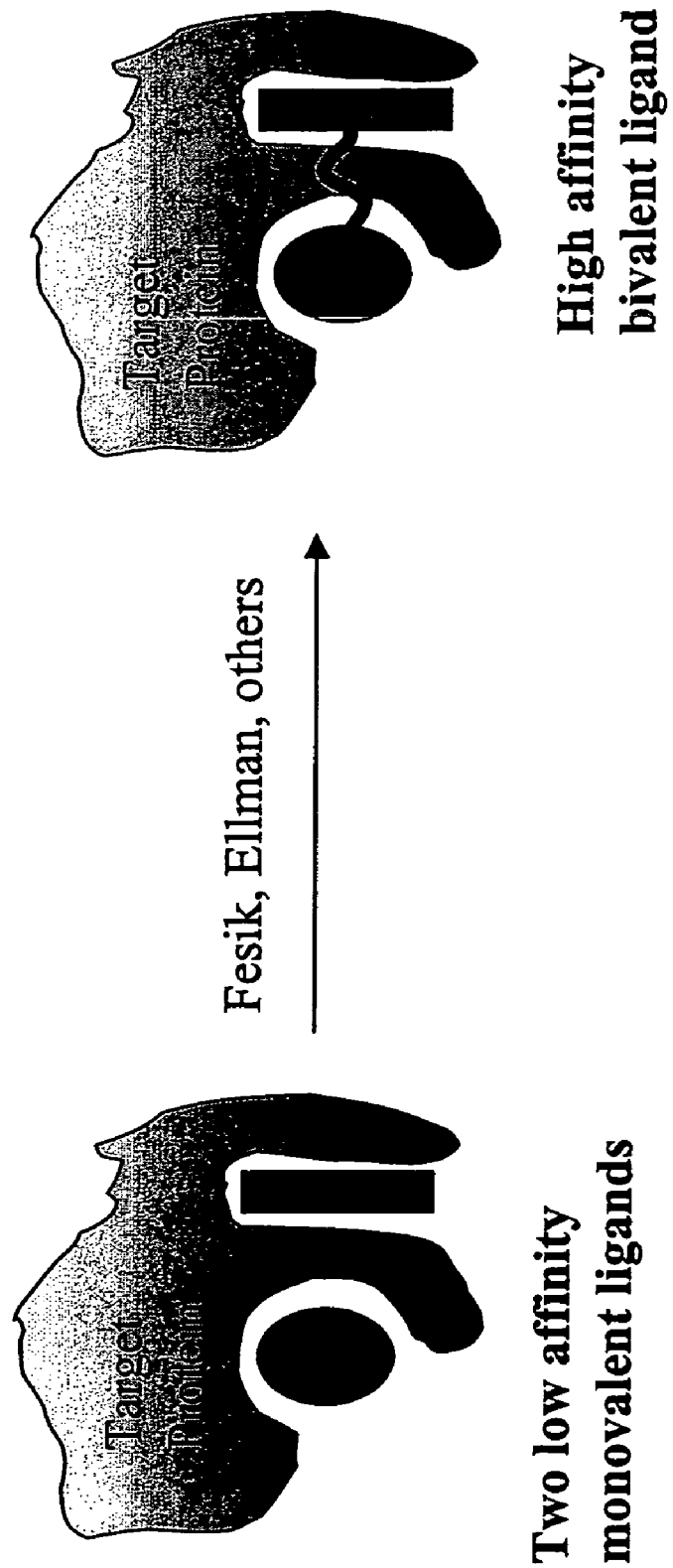
FIG. 2 illustrates an example of high affinity protein ligand created by immobilizing two different modest affinity binding elements onto a surface. The surface is anticipated to act as a "library of linkers." In other words, the two binding elements should be spaced appropriately on some fraction of the surface to bind in a bivalent fashion to the protein.
Figure 3:
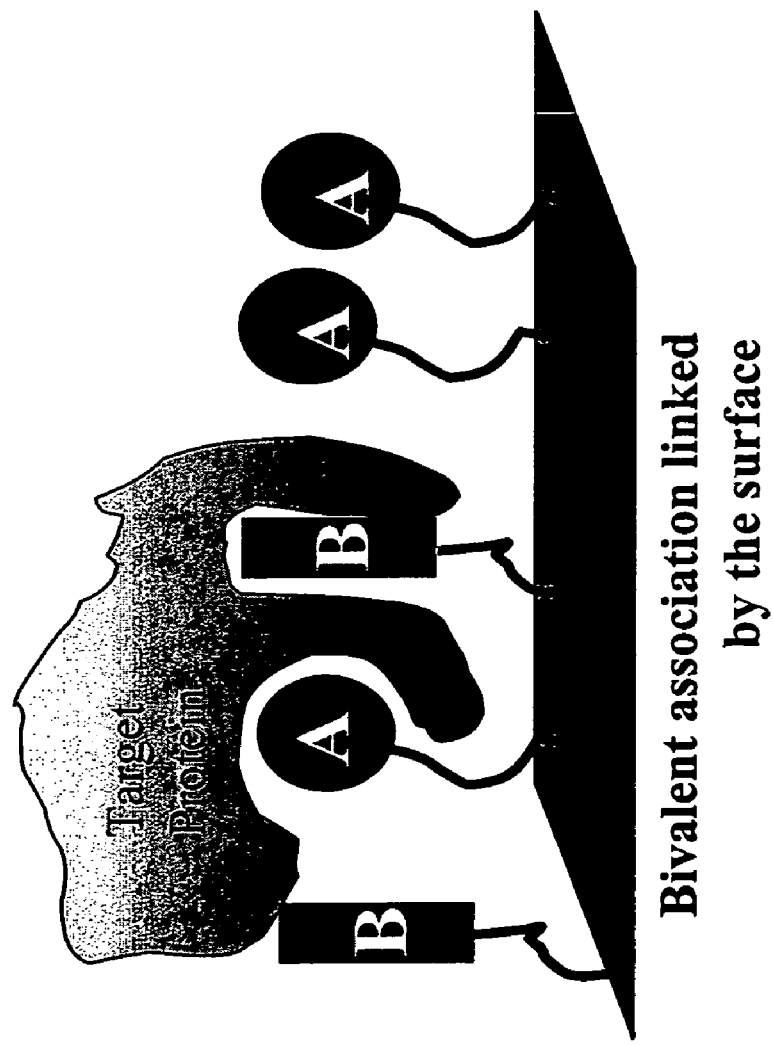
FIGS. 3A-3D illustrate examples of different ways in which modest affinity binding elements could collaborate when immobilized to a support to capture proteins with high affinity.
Figure 4:
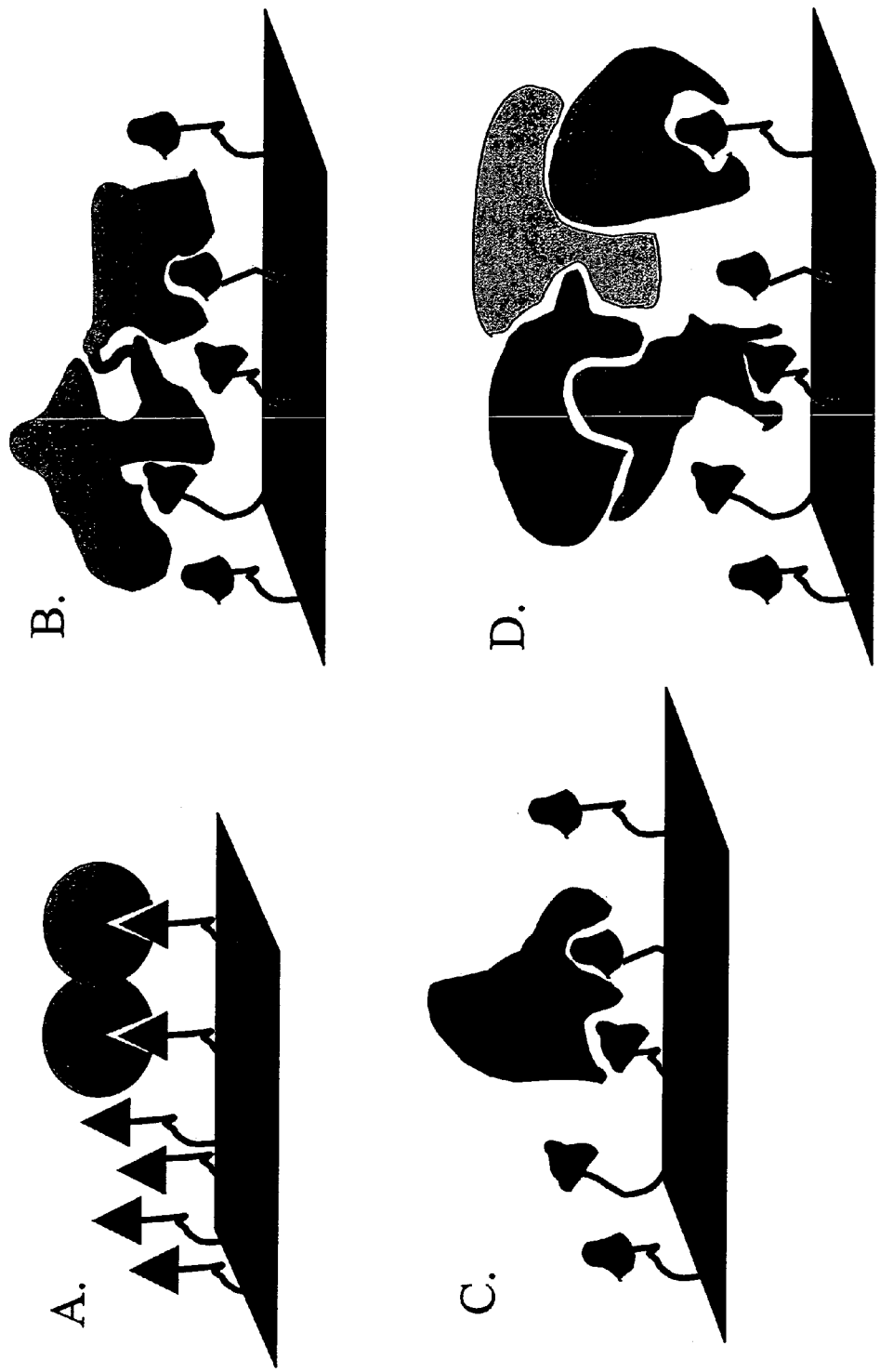
FIG. 4 illustrates an example of how high affinity binding of a particular post-translationally modified protein through a two-point contact is accomplished.

Examples of how this may be implemented to provide high affinity immobilized capture agents include two binding elements that are different and non-competitive bind to different surfaces of a monomeric protein. The different surfaces could be different domains of a multi-domain protein or different surface features on a single domain. Note that one could distinguish between splice variants of a protein using this approach (see FIG. 2 for an example). Another aspect includes two binding elements bind different proteins which are part of the same multiprotein complex (see FIGS. 3A-3D for an example). Still another aspect includes one binding element that recognizes the polypeptide, while a second binding element recognizes a particular post-translational modification (phosphorylation, ubiquitination, glycoslyation, etc.) (see FIG. 4 for an example). Thus the two binding elements would cooperate to bind tightly to a modified form of a protein and not to an unmodified protein.

Surface-immobilized capture agents may be one-half or a portion of a device for the sensitive detection of a target, e.g., proteins. The other half or portions would comprise a method to quantify the amount of target(s) captured by the capture agent. There are many ways this could be accomplished, for example using a "sandwich assay" in which the captured proteins are probed with a fluorescently labeled antibody against the protein of interest. The level of bound fluorescence, which corresponds to the level of the captured protein, would then be monitored using a number of commercially available instruments. Luminex (Austin, Tex.) as well as other companies market instruments that enable this type of assay to be done in a high-throughput format. Another possibility is to immobilize the binding elements on a surface capable of intrinsically sensing the binding of the target molecule. For example, a modified gold surface, which would allow surface plasmon resonance (SPR) to be used to quantify binding. Many other detection schemes, some of which are described below, are possible and it is important to note that the invention, which focuses on the development of novel capture agents, could be wedded to any of them.

Certain embodiments of the invention relate to compositions and methods for detection of a target or capture target. A detector may comprise one or more sensing elements or regions of a support. In some embodiments, for example when the support is a planar surface, a support may include segregated areas separating sensing elements. The segregated sensing elements or regions may include one or more MECAs. In some embodiments, one or more sensing elements or regions for a number of targets are contemplated. A support may contain one, tens, hundreds, or thousands of sensing elements. One or more supports may be incorporated in or used in conjunction with a detection means to form a detector. These detectors may be useful in methods of analyzing complex mixtures of substances such as clinical samples or cell extracts, as well as gaseous or volatile substances of both biological and non-biological origin.

A detector may comprise a support surface on which capture agents are immobilized (e.g., peptides or proteins). The building blocks of a detector and related methods include surface chemistry (the chemical bonds that immobilize binding elements), sample(s) (substances used to study interactions, compositions or expression levels), capture agents (agents used to capture and quantify target(s)) and detection methods (methods used to detect binding to or interact with capture agents on the surface of support).

Embodiments of the invention may have several uses in research, medicine, military, forensics and other fields. In general, almost any application (e.g., diagnostics) that currently uses immobilized antibodies could employ these capture agents, which are superior to antibodies in many ways. Furthermore, proteomics devices, such as protein-detecting microarrays designed to monitor the levels of hundreds of proteins simultaneously, would be greatly enabled by the existence of these capture agents. Currently, most such devices are based upon biological macromolecules such as antibodies or nucleic acid aptamers, which are difficult to produce in large quantities and can often lose activity when attached to a surface. A variety of the capture agents described herein may be produced in bulk and at less cost, as well as being stable in a variety of conditions and for extended periods of time.

For example, in medicine, MECAs may detect the presence or absence of multiple biological markers in complex samples such as blood or urine, providing a valuable diagnostic tool. In the military, the presence of certain polypeptides can signal the presence of a biological warfare agent in the environment. In the research field, it is an efficient and fast screening/detection tool. The invention as described herein does not require any prior knowledge of the polypeptide, molecule, or substance to be bound to the MECAs. Binding elements may be identified by screening various combinatorial or expression libraries or other types of compound collections.

Compositions and methods disclosed herein may include "chimeric binding elements," in particular chimeric binding elements that include a first known low to moderate affinity binding element and a second oligomeric component that provides a second binding element. Typically, a chimeric binding element is identified by screening a plurality of oligomeric compounds coupled to the known binding element. Certain chimeric binding elements provide for the rapid transformation of low to moderate affinity binding elements into high affinity capture agents. Embodiments of the invention also include a facile method to obtain high affinity synthetic protein capture agents. Various embodiments of the chimeric binding element approach is a simple and efficient route to such molecules is described herein.

Relatively low molecular weight synthetic species may be isolated that are shown to capture a target protein, e.g., Mdm2 and/or Ubiquitin, from solutions containing a large excess of other proteins. A semi-automated screening protocol is described below that makes this system capable of high throughput. The invention provides for screening combinatorial chemical libraries or large compound collections for chimeric binding elements with a reasonable assurance of success.

Most ligands obtained from screening naïve libraries bind their target protein with equilibrium dissociation constants ($K_D$s) in the μM range. Such modest affinity ligands are suitable for some applications such as chemical genetics studies (Schreiber, 2003; Koehler et al., 2003; Kuruvilla et al., 2002), but for other important applications much higher affinity is required. For example, there is considerable interest in the development of protein-detecting microarrays based on small molecule capture agents attached to a modified glass slide, encoded beads or some other suitable surface (for reviews, see Kodadek, 2001; 2002). In order for such devices to be applied to the analysis of low abundance proteins, the synthetic capture agents must exhibit binding properties comparable to that of a good monoclonal antibody, forming complexes with $K_D$s in the $10^{-8}$ M to $10^{-12}$ M range. To evolve a modest affinity lead compound to a high affinity capture agent by traditional medicinal chemistry methods is time-consuming and labor-intensive, which make it difficult to apply on a proteomic scale.

The inventors describe a rapid and economical method to transform modest affinity lead compounds into high affinity agents. Typically, the protocol involves capping a combinatorial library of oligomeric compounds, such as peptides, peptoids or other types of molecules that may be used to produce combinatorial libraries, with the lead compound (i.e., first binding element) and screening this library against the target protein under conditions too demanding for the first binding element to support binding. The screen will simultaneously select for a second binding element within the oligomer and a suitable linker connecting this element and the lead compound, thus providing a MECA comprising a chimeric binding element. The efficacy of this approach may be demonstrated with the isolation and characterization of two synthetic molecules that are able to capture Mdm2 protein and ubiquitin, respectively, from complex solutions containing a large excess of other proteins even when the target is present at nanomolar concentrations, see Examples below.

II. Supports for Immobilizing Binding Elements

In various embodiments of the invention binding elements and MECAs may be operatively coupled to a support. "Support" refers to a solid phase onto which a MECA can be provided, (e.g., by attachment, deposition, coupling and other known methods). One or more binding elements may be immobilized on supports including, but not limited to glass (e.g., a chemically modified glass slide), latex, plastic, membranes, microtiter, wells, mass spectrometer plates, beads (e.g., cross-linked polymer beads) or the like.

In one aspect, the invention provides supports adapted for use with a detector or a detection method(s) (e.g., ELISA), wherein the support comprises a MECA immobilized on the support surface. The MECA(s) will typically bind with a high affinity and specificity to a component of a sample. In various non-limiting embodiments the sample is a biological sample. The component may be involved in a biological pathway (e.g., signal transduction, immunological response, cytoplasmic or membrane enzyme mediated pathway, cell cycle or developmental cycle pathway). Typically, MECAs are located at different addressable, segregated regions referred to as sensing elements or regions on a support so that one can readily distinguish which components in a sample are bound to a support. In some embodiments, MECAs can be placed in the same sensing element or region of the support as long as the components can be differentially detected. The supports and the MECAs are described in detail herein.

Targets or capture targets can be captured on any of a variety of MECA/support. One of the various MECA/support is a protein biochip. Among the many protein biochips described in the art are those biochips produced by Ciphergen Biosystems (Fremont, Calif.), Packard BioScience Company (Meriden Conn.), Zyomyx (Hayward, Calif.) and Phylos (Lexington, Mass.). In general, protein biochips comprise a support having a generally planar surface. A binding element(s) and/or a MECA(s) is typically attached to the surface of the support. In certain embodiments of the invention a surface may comprise a plurality of addressable locations, each of which location has one or more binding elements bound to form a MECA. The binding element can be a biological molecule, such as a peptide, polypeptide or a nucleic acid, which binds other biomolecules in a specific manner. Examples of protein biochips are described in the following patents or patent applications: U.S. Pat. Nos. 6,225,047 and 6,329,209, and International publication WO 99/51773 and WO 00/56934, each of which is incorporated herein by reference.

In one embodiment the support is capable of being engaged by an interface of a mass spectrometer which positions the support in an interrogatable relationship with an ionization source. The support can be in any shape, e.g., in the form of a strip, a plate, or a dish with a series of wells. Each MECA(s) may be immobilized at different addressable locations at the support surface.

Typically, each sensing element or region comprises a different MECA so that one can readily distinguish which target(s) in a sample is/are bound to the support. In some embodiments, different MECAs can be produced in the same sensing region of the support as long as the MECAs have different detectable characteristics.

Each sensing region on the support may be "addressable" in that during detection of capture target binding, a detection method may be directed to, or "addresses" the sensing region where a capture target is bound to the MECA. The addressable locations can be arranged in any pattern on the support, but are preferably in regular pattern, such as lines, orthogonal arrays, or regular curves (e.g., circles). Alternatively, MECAs can be placed on the support surface in continuous patterns, rather than in discontinuous patterns.

Alternatively, the support can be a separate material. For example, a support can be a solid phase, such as a polymeric, paramagnetic, latex or glass bead, upon which are immobilized binding elements, which produce a MECA for binding a target. A solid phase material may be placed onto a probe or detectable media (e.g., fluorescently tagged bead) that is removably insertable into a gas phase ion spectrometer or passed by a detector such as a laser/spectrometer device. The solid phase with each type of capture agent is typically placed at different addressable locations of the support surface. Alternatively, as noted above, different capture agents can be placed on the same addressable locations as long as they are able to be differentially detected.

The support can be also shaped so that it is adapted for use with various components of a gas phase ions spectrometer, such as inlet systems and detectors. For example, the support can be adapted for mounting in a horizontally and/or vertically translatable carriage that horizontally and/or vertically moves the support to a successive position. This allows components bound to different locations of the support surface to be analyzed without requiring repositioning of the support by hand.

The support can be made of any suitable material. For example, the support materials include, but are not limited to, insulating materials (e.g., glass such as silicon oxide, plastic, ceramic), semi-conducting materials (e.g. silicon wafers), or electrically conducting materials (e.g., metals, such as nickel, brass, steel, aluminum, gold, or electrically conductive polymers), organic polymers, biopolymers, or any combination thereof. The support material can also be solid or porous. Examples of supports suitable for use in embodiments of the invention are described in U.S. Pat. No. 5,617,060 and International Publication WO 98/59360, each of which are incorporated by reference.

The support can be conditioned to bind binding elements. In some embodiments, the surface of the support can be conditioned (e.g., chemically or mechanically such as roughening) to place binding elements on the surface. Typically, a support comprises reactive groups that can immobilize binding elements. For example, the support can comprise a carbonyldiimidazole group which covalently reacts with amine groups of nucleic acids or peptides. In another example, the support can comprise an epoxy surface which covalently reacts with amine and thiol groups of DNA and proteins. Supports with these reactive surfaces are commercially available from Ciphergen Biosystems (Fremont, Calif.).

III. Binding Elements

Binding elements are molecules or portions of molecules that demonstrate an affinity for a particular target, which may or may not bind with a high enough affinity to capture a particular target. Binding elements are typically operatively coupled to a support as described herein and may be part of a MECA. In other embodiments, a binding element includes a chimeric binding element wherein two or more binding elements are operatively coupled. Typically, high affinity binding of a target will result from concomitant binding of two or more chimeric binding elements to a single target. As used herein, these binding elements include low and/or moderate affinity binding elements. "Low affinity," as used herein, is defined as an interaction with a dissociation constant ($K_D$) of $\geq 10^{-5}$ M, "moderate affinity" as used herein is defined as a $K_D$ between $10^{-5}$ M and $10^{-8}$ M, and "high affinity" as used herein is defined as a $K_D$ of $<10^{-8}$ M. Binding elements used to form a MECA may be any molecule or substance that binds a target molecule (capture target) with preferably a low to moderate affinity. In various embodiments a binding element(s) may include, but is not limited to a peptide, a peptoid (i.e., N-substituted oligoglycines), a peptide-like molecule, a polypeptide, a protein, a polysaccharide, a nucleic acid, a small molecule, an inorganic molecule, an organic molecule, a single chain antibody or the like. It is also contemplated that combinations of different classes of binding elements may also be used, for example, a peptide modified with a small molecule and the like. Capping molecules used to form chimeric binding elements may be any molecule or substance that binds a target molecule with a low to moderate affinity. In various embodiments a capping molecule may include, but is not limited to a peptide, a peptoid (i.e., N-substituted oligoglycines), a peptide-like molecule, a polypeptide, a protein, a polysaccharide, a nucleic acid, a small molecule, an inorganic molecule, an organic molecule, a single chain antibody or the like. It is contemplated that combinations of different classes of binding elements may be used in forming a chimeric binding element, for example, a peptoid with a small molecule as a capping molecule and the like. Binding elements may be identified by a variety of known methods including, but not limited to combinatorial, expression, phage display, yeast two hybrid libraries and the like. One or more binding element may be used to form a MECA as described herein. In some embodiments, binding elements may be covalently coupled or fused to each other, for example a fusion of two peptides, with or without intervening residues, into a single linear molecule, i.e., a chimeric binding element. For each MECA, a preferred density may be empirically determined by arraying a number of sensing elements, which include one or more binding elements, at varying densities and identifying an optimal binding element density. In some embodiments, the individual binding elements could be anchored in a fluid membrane, such a lipid bilayer, allowing them to reorient so as to achieve proper spacing to act as a high affinity MECA.

In certain embodiments, a binding element may be derived from a biological pathway(s) of interest. Biological pathways include, but are not limited to components such as metabolites, intermediates, polypeptides, lipids, lipoproteins, carbohydrates, and nucleic acids. Binding elements may be selected from any suitable materials as long as they bind to a target. For example, binding elements may be selected from polypeptides, lipids, lipoproteins, carbohydrates, nucleic acids, steroids, glycolipids, small organic, inorganic molecules and/or derivatives thereof. Typically, binding elements may include, but are not limited to entities that bind proteins, receptors, ligands, antibodies, organelles, microbes, pathogens, and nucleic acids.

One or more different types of binding elements and/or MECA may be immobilized on a support surface. MECAs may be localized or segregated to particular regions on a support or on particular supports, e.g., latex beads. Each of these particular regions will be able to bind at least one target. These regions are referred to as sensing elements or regions. Typically, at least 2, 3, 4, 5, 6, 7, 8 or more different binding elements, or even hundreds or thousands of different binding elements can be immobilized on a support surface to form various MECAs. MECAs can be selected to bind to a single target or multiple targets.

In certain embodiments, a target(s) may be indicative of a particular state of a non-biological or biological substance, sample or pathway. For example, many signal transduction pathways and their components are known, and the selection of a MECA depends on analysis of which signal transduction pathway(s) are to be monitored. For example, binding elements and/or MECAs may be selected from those that selectively bind to components of the Ras/Raf signal transduction pathway, the p53 tumor suppressor signal transduction pathway, the BRCA1 signal transduction pathway, a pathogen or pathogen bi-product, a marker related to a disease state or any combination thereof. Many other signal transduction pathways are known in the art, and are described in, e.g., Alberts et al. (1994) and Lodish et al. (2000). In other embodiments, a MECA may be chosen to detect the presence or absence of one or more pathogen, such as bacteria, viruses, parasites or a portion or by product thereof.

In certain aspects, MECAs may be selected so that a number of MECAs bind to a target or to components of a target pathway, disease or organism. An array of MECAs may be selected so that at least two different MECAs on the support surface bind to components that are sequential in their activation in a signal transduction or other biologic/non-biologic pathway. Having a number of MECAs that bind to components of a single pathway, disease or organism on a support allows those skilled in the art to readily determine which component in a sample is, for example defective. In some embodiments, a sample may be related to normal/non-normal cell development, normal/disease condition, infected/non-infected condition, presence/absence of an organism/agent and the like.

A capping molecule or first binding element of a chimeric binding element may be coupled to a monomer, polymer or oligomer of at least 1, 2, 3, 4, 5, 6, 7, 8, 9, 10, 11, 12, 13, 14, 15, 16, 17, 18, 19, 20 or more units that will vary in order and compositions from candidate element to candidate element. Each unit may be an amino acid, a nucleic acid, a saccharide, an inorganic molecule, organic molecule, or a combination thereof, including various derivatives thereof. Thus, providing a library of candidates from which a chimeric binding element may be selected.

A. Peptides and Peptide Like Molecules

In various aspects of the invention, peptides, peptoids, polypeptides, and/or proteins may be used as a binding element or as a portion of a chimeric binding element. The peptides, polypeptides and/or proteins used as a binding element or an oligomer in a chimeric binding element may be an isolated, a recombinant or a synthetic peptide(s), peptoid(s), polypeptide(s), proteins and/or other oligomeric molecule. A peptide, peptoid or polypeptide may be identified as a binding element by various known methods, such as phage display library, combinatorial peptide or peptoid library, classical binding studies and the like. Typically, the composition of a peptide, peptoid, polypeptide or other oligomer will be variable and, in certain embodiments, will be operatively coupled with a capping molecule and/or first binding element to form a library of candidate chimeric binding elements.

The present invention may also relate to fragments of a polypeptide. Fragments, including the N-terminus of the molecule may be generated by genetic engineering of translation stop sites within a coding region. Alternatively, treatment of polypeptide with proteolytic enzymes, known as proteases, can produce a variety of N-terminal, C-terminal and internal fragments. In certain embodiments, peptides or peptide like molecule, i.e., peptoids, may be synthesized by known methods. Examples of fragments may include contiguous residues of 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300 or more amino acids, amino acid mimetics, derivatives, or combinations thereof. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

B. Synthetic Peptides

Various embodiments of the invention describe peptides or peptide mimetics for use in the production of MECAs. Peptides, peptide mimetics or peptide like molecules of the invention may also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide or oligomeric sequences, or libraries of overlapping peptides or oligomers, usually from about 6 up to about 35 to 50 amino acids or monomers, which correspond to binding elements or second binding elements of chimeric binding elements described herein, can be readily synthesized and then screened in screening assays designed to identify molecules, peptides, peptide mimetics, or other oligomer of interest. In some embodiments, recombinant DNA technology may be employed wherein a nucleotide sequence which encodes a peptide of the invention is inserted into an expression vector, transformed or transfected into an appropriate host cell and cultivated under conditions suitable for expression.

C. Fusion Peptides

A specialized kind of insertional variant is the fusion protein or peptide. This molecule generally has all, a substantial portion, or a portion of a first molecule, linked at the N- or C-terminus, to all or a portion of a second molecule. For example, fusions typically employ leader sequences from other species to permit the recombinant expression of a protein in a heterologous host. Other useful fusions include linking of binding elements. Fusions of the invention include a fusion of two or more binding elements. In certain embodiments the two or more elements are reversibly or irreversibly coupled to each other.

D. Purification of Peptides

In certain embodiments, it may be desirable to purify a peptide or polypeptide. Protein and peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide or peptide like molecule are ion-exchange chromatography, exclusion chromatography; polyacrylamide gel electrophoresis; isoelectric focusing. A particularly efficient method of purifying peptides or peptide like molecules is fast protein liquid chromatography or even HPLC. These purification techniques may be used to purify other binding elements or portions of chimeric binding elements.

Certain aspects of the present invention concern the purification, and in particular embodiments, the substantial purification, of a peptide, peptide like molecule, or other binding element. The term "purified peptide, peptide like molecule, polypeptide or binding element" as used herein, is intended to refer to a composition, isolatable from other components, wherein the peptide is purified to any degree relative to its naturally-obtainable state. A purified protein, peptide, or binding element therefore also refers to a protein, peptide, or binding element, free from the environment in which it may naturally occur.

Generally, "purified" will refer to a protein, peptide, or binding element composition that has been subjected to fractionation to remove various other components, and which composition substantially retains its activity. Where the term "substantially purified" is used, this designation will refer to a composition in which the protein, peptide, or binding element forms the major component of the composition, such as constituting about 50%, about 60%, about 70%, about 80%, about 90%, about 95% or more of the peptides, peptide like molecules, polypeptides, or binding elements in the composition. Various methods for quantifying the degree of purification will be known to those of skill in the art in light of the present disclosure.

Various techniques suitable for use in purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified peptide or binding element.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Monoclonal and Single Chain Antibodies

Binding elements may be antibodies that bind to a target. A majority of single chain antibodies do not bind a target with an affinity sufficient for the antibody to be used as a capture agent. Therefore, certain embodiments of the invention may utilize sub-optimal single chain antibodies to produce a capture agent. In various aspects of the invention antibodies that demonstrate a low or moderate affinity for a target may be used as a binding element to produce a capture agent. These include, e.g., monoclonal antibodies, antibody fragments, single chain antibodies, and the like. Methods for making these molecules are well-known in the art.

For example, monoclonal antibodies can be prepared by any technique that provides for the production of antibody molecules by continuous cell lines in culture, including the hybridoma technique (Kohler and Milstein, 1975), as well as the trioma technique, the human B-cell hybridoma technique (Kozbor et al., 1983), and the EBV-hybridoma technique to produce human monoclonal antibodies (Cole et al., 1985).

Fragments of antibodies may also be useful as binding elements. While various antibody fragments can be obtained by the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). Single chain antibodies may also be useful in the production of capture agents. Methods for producing single chain antibodies were described in, for example, U.S. Pat. No. 4,946,778. Techniques for the construction of Fab expression libraries were described by Huse et al. (1989); these techniques facilitate rapid identification of monoclonal Fab fragments with the desired specificity for pathway components.

F. Aptamers

In certain embodiments, binding elements may comprise nucleic acids. As discussed below, a nucleic acid may contain a variety of different bases and yet still produce a binding element that may be used in the production of a MECA.

The methods of the present invention may select and use nucleic acids that bind to a variety of substances with a low to moderate affinity. In certain embodiments, a nucleic acid may comprise or encode an aptamer. An "aptamer" as used herein refers to a nucleic acid that binds a target molecule through interactions or conformations other than those of nucleic acid annealing/hybridization. Methods for making and modifying aptamers, and assaying the binding of an aptamer to a target molecule may be assayed or screened for by any mechanism known to those of skill in the art (see for example, U.S. Pat. Nos. 5,840,867, 5,792,613, 5,780,610, 5,756,291 and 5,582,981, incorporated herein by reference).

G. Other Binding Elements

Virtually any molecule or compound having a low to moderate affinity for a target molecule may be used as a binding element and/or a capping molecule. Binding elements may include non-biological or biological polymers, polysaccharides, a variety of small molecules, lipids, and the like.

Methods have been developed for the combinatorial (e.g., rapid-serial or parallel) synthesis and screening of libraries of small molecules of pharmaceutical interest, and of biological polymers such as peptoids, polypeptides, proteins, oligonucleotides and deoxyribonucleic acid (DNA) polymers (Eichler et al., 1995; Cho et al., 1999; LePlae et al., 2002; Ostergaard and Holm, 1997; Yang et al. 1999). U.S. Pat. Nos. 6,475,391 and 6,461,515; and Brocchini et al. describe exemplary methods and compositions for the preparation and characterization of polymer combinatorial libraries for selecting polymer materials (Brocchini et al., 1997). Exemplary synthetic methods for oligosaccharides is provided in Kanemitsu and Kanie (2002).

Various small molecule libraries may be obtained from commercial or non-commercial sources, as well as synthesizing such compounds using standard chemical synthesis techniques.

nology or combinatorial synthesis technology (see U.S. Pat. No. 6,344,334; Gallop et al. (1994), Gordon et al. (1994), Thompson and Ellman (1996), each of which is incorporated herein by reference).

IV. Methods of Detection

Methods detecting targets captured on a solid support can generally be divided into photometric methods of detection and non-photometric methods of detection.

Photometric methods of detection include, without limitation, those methods that detect or measure absorbance, fluorescence, refractive index, polarization or light scattering. Methods involving absorbance include measuring light absorbance of an analyte directly (increased absorbance compared to background) or indirectly (measuring decreased absorbance compared to background). Measurement of ultraviolet, visible and infrared light all are known. Methods involving fluorescence also include direct and indirect fluorescent measurement. Methods involving fluorescence include, for example, fluorescent tagging in immunological methods such as ELISA or sandwich assay. Methods involving measuring refractive index include, for example, surface plasmon resonance ("SPR"), grating coupled methods (e.g., sensors uniform grating couplers, wavelength-interrogated optical sensors ("WIOS") and chirped grating couplers), resonant mirror and interferometric techniques. Methods involving measuring polarization include, for example, ellipsometry. Light scattering methods (nephelometry) may also be used.

Non-photometric methods of detection include, without limitation, magnetic resonance imaging, gas phase ion spectrometry, atomic force microscopy and multipolar coupled resonance spectroscopy. Magnetic resonance imaging (MRI) is based on the principles of nuclear magnetic resonance (NMR), a spectroscopic technique used by scientists to obtain microscopic chemical and physical information about molecules, for a review see Homak, 2002. Gas phase ion spectrometers include mass spectrometers, ion mobility spectrometers and total ion current measuring devices.

Mass spectrometers measure a parameter which can be translated into mass-to-charge ratios of ions. Generally ions of interest bear a single charge, and mass-to-charge ratios are often simply referred to as mass. Mass spectrometers include an inlet system, an ionization source, an ion optic assembly, a mass analyzer, and a detector. Several different ionization sources have been used for desorbing and ionizing analytes from the surface of a support or biochip in a mass spectrometer. Such methodologies include laser desorption/ionization (MALDI, SELDI), fast atom bombardment, plasma desorption and secondary ion mass spectrometers. In such mass spectrometers the inlet system comprises a support interface capable of engaging the support and positioning it in interrogatable relationship with the ionization source and concurrently in communication with the mass spectrometer, e.g., the ion optic assembly, the mass analyzer and the detector.

Solid supports for use in bioassays that have a generally planar surface for the capture of targets and adapted for facile use as supports with detection instruments are generally referred to as biochips. Protein biochips are biochips adapted for use in the detection of peptides or proteins or targets captured by proteins.

In certain embodiments, methods for detecting components of a biological pathway, e.g., a signal transduction pathway, wherein the methods may comprise: providing a support comprising at least two different capture agents immobilized on a surface of the support, wherein the capture agents specifically bind to a target component(s) of a biological pathway, contacting a sample with a support, and detecting the components of the biological pathway bound to their corresponding capture agents on the support by gas phase ion spectrometry. In some embodiments, data generated by gas phase ion spectrometry from a test sample can be compared to a control to determine if there is any defect in the biological pathway in the test sample. The sample preparation methods and gas phase ion spectrometry analysis are described in U.S. Patent Application 20020137106, incorporated herein by reference.

V. Sample Preparation and Handling

The sample used in this invention can be derived from essentially any source. In particular embodiments the sample may be derived from a biological source. These include, e.g., body fluids such as blood, feces, sputum, urine, serum, saliva, or extracts from biological samples, such as bacterial or cell lysates. In certain embodiments, a sample is in liquid form. In some embodiments a sample may be derived from a gas sample, such as an air sample.

The sample is contacted with a support comprising a capture agent in any suitable manner, e.g., bathing, soaking, dipping, spraying, washing over, or pipetting. Generally, a volume of sample containing from 1 pM to 1 mM of a capture target in a volume from about 1 µl to 1 ml is sufficient for binding to the capture agent. The sample can contact the support comprising one or more capture agents for a period of time sufficient to allow the target molecules to bind to the capture agent. Typically, the sample and the support comprising the capture agents are contacted for a period of between about 30 seconds and about 12 hours. In some embodiments, between about 30 seconds and about 15 minutes. Typically, the sample is contacted with the capture agent under ambient temperature and pressure conditions. For some samples, however, modified temperature (typically 4° C. through 37° C.) and pressure conditions may be desirable. These conditions are determinable by those skilled in the art.

After the support contacts the sample or sample solution, it is preferred that unbound and weakly absorbed materials on the support surface are washed out or off so that only the tightly bound materials remain on the support surface. Washing a support surface can be accomplished by, e.g., bathing, soaking, dipping, rinsing, spraying, or washing the support surface with an eluant. A microfluidics process may be used when an eluant is introduced to small spots of capture agents on the support. Typically, an eluant may be at a temperature of between 0° C. and 100° C. or between 4° C. and 37° C. In some embodiments, washing unbound materials from the probe surface may not be necessary if pathway components bound on the probe surface can be resolved by gas phase ion spectrometry without a wash or are detected using a high specificity sandwich reagent that will ignore molecules that might be present other than the target.

Any suitable eluants (e.g., organic or aqueous) that preserve the relevant interaction can be used to wash the support surface. Preferably, an aqueous solution is used. Exemplary aqueous solutions include, e.g., a HEPES buffer, a Tris buffer, or a phosphate buffered saline. To increase the wash stringency of the buffers, additives can be incorporated into the buffers. These include, but are limited to, ionic interaction modifier (both ionic strength and pH), hydrophobic interaction modifier, chaotropic reagents, affinity interaction displacers. Specific examples of these additives can be found in, e.g., PCT publication WO98/59360. The selection of a particular eluant or eluant additives is dependent on experimental conditions (e.g., types of capture agents used or biological pathway, e.g., signal transduction, immunological, plasma membrane enzyme mediated, cell cycle or developmental cycle components to be detected), and can be determined by those of skill in the art.

Prior to desorption and ionization of a target from a support surface, an energy absorbing molecule ("EAM") or a matrix material is typically applied to the support surface. The energy absorbing molecules can assist absorption of energy from an energy source from a gas phase ion spectrometer, and can assist desorption of targets from the support surface. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in the art. See, e.g., U.S. Pat. No. 5,719,060 for additional description of energy absorbing molecules.

The energy absorbing molecule and the sample can be contacted in any suitable manner. For example, an energy absorbing molecule is mixed with the sample, and the mixture is placed on the support surface. In another example, an energy absorbing molecule can be placed on the support surface prior to contacting the support surface with the sample. In another example, the sample can be placed on the support surface prior to contacting the support surface with an energy absorbing molecule. Then the components bound to the capture reagents on the support surface are desorbed, ionized and detected as described in detail below.

VI. Analysis of Data

Data generated by desorption and detection of a bound target (e.g., signal transduction, immunological, plasma membrane enzyme mediated, cell cycle, developmental cycle, pathogen components) can be analyzed using any suitable means. In one embodiment, data is analyzed with the use of a programmable digital computer. The computer program generally contains a readable medium that stores codes. Certain code can be devoted to memory that includes the location of each feature on a support, the identity of the capture agents at that feature and the elution conditions used to wash the support surface. The computer also contains code that receives as input, data on the strength of the signal at various addressable locations on the support. This data can indicate the number of targets detected, including the strength of the signal generated by each target.

Data analysis can include the steps of determining signal strength (e.g., height of peaks) of a target(s) detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each target can be displayed in the form of relative intensities in the scale desired. Alternatively, a standard may be admitted with the sample so that a peak from the standard can be used as a reference to calculate relative intensities of the signals observed for each target detected.

Data generated by desorption and detection of target(s) in a test sample can be compared to control data to determine if the target(s) in the test sample is normal. A control data refers to data obtained from comparable samples from a normal cell, sample or person, which or who is known to have defined profile with regard to target molecules or sample conditions. For each target being analyzed, a control amount of each component from a normal or standardized sample is determined. Preferably, the control amount of each target is determined based upon a significant number of samples taken from samples such as normal cells or persons so that it reflects variations of the amount of these targets seen in the normal cell or population.

If the test amount of a particular target is significantly increased or decreased compared to the control amount of the component, then this is a positive indication that the test sample has an underlying defect or contains a particular test substance or organism. For example, if the test amount of a biological pathway component is increased or decreased by at least 1.5-fold, 2-fold, 5-fold or 10-fold compared to the control amount, then this is an indication that the test sample has a defect in the biological pathway.

Data generated by the detector, e.g., the mass spectrometer, can then be analyzed by computer software. The software can comprise code that converts signal from the detector into computer readable form. The software also can include code that applies an algorithm to the analysis of the signal to determine whether the signal represents a "peak" in the signal corresponding to a target. The software also can include code that executes an algorithm that compares signal from a test sample to a typical signal characteristic of "normal" and determines the closeness of fit between the two signals. The software also can include code indicating whether the test sample has a normal profile of the target(s) or if it has an abnormal profile.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Mixed Element Capture Element Studies—Materials and Methods

Plasmids. PQE60/PRE1 and pProEX-1/Gal80, the expression vectors for $His_6$PRE and $His_6$Gal80, were provided by Prof. Stephen Johnston (UT Southwestern, Dallas). pQE60 places the $His_6$ tag at the carboxy terminus of PRE1 while the $His_6$ tag for pProEX-1/Gal80 is at the N terminus of Gal80. The GST fusion of PRE1 was constructed by inserting a PCR amplicon containing the PRE1 gene into Nco1/BamHI-cut pGEXCSTEV plasmid (provided by Prof. Johnston). The plasmid expressing GST fused human Mdm2, pGEX Mdm2, was provided by Prof. David Lane, University of Dundee, Dundee. Construction of pMal-c2X-Ndm2 was achieved by restriction digest of pGEX-Mdm2 with BamHI/EcoRI and ligation of the resulting fragment into the pMA1-c2X plasmid purchased from NEB. The plasmid encoding full-length mouse Creb binding protein (CBP), was pRC/RSV-mCBP-HA-RK. A fragment of CBP including the KIX domain, amino acids 378-817, was amplified by PCR and inserted into BamHI/HindIII digested pRSET-A vector (Invitrogen) to produce the resultant plasmid pRSET-CBP(378-8 17), which expresses the $His_6$ tag at the N-terminus of the protein. The plasmid expressing the GST fusion of CBP(378-817), pGEX-2T-CBP(378-817), was constructed by insertion of the same CBP amplicon into BamHI/HindIII digested pGEX-2T vector purchased from Pharmacia Biotech that was engineered with a HindIII site. A $His_6$ tag was added to the pGEX 2T-CBP (378-817) construct at the carboxy terminus of CBP by amplifying the CBP fragment with the primers 5'-CC GCG GGA TCC GCC TGT TCT CTC CCA CAC TGT CG-3' (SEQ ID NO:1) and 5'-GAA TTC AAG CCT TTA GTG GTG ATG GTG GTG ATG GGC TGC TGG TTG CCC CAT GCC CAC AC-3' (SEQ ID NO:2) and inserting back into the BamHI/HindIII digested pGEX 2T vector.

Proteins and Antibodies. Glutathione-S-transferase (GST) fusion proteins were expressed in *E. coli* cells gown in LB media+ampicillin to an $OD_{600}$ of 0.6-0.8 and induced with 1 mM IPTG for 2-3 hours at 37° C. The cells were lysed using sonication and centrifuged at 83,000 g to remove cell debris. Glutathione sepharose beads (Pharmacia Biotech) equilibrated with PBS buffer were added to the lysate and incubated for 1 hour at 4° C. with agitation. The beads were poured into a column, washed with 20 column volumes of PBS+0.5% triton X-100, followed by 10 column volumes of PBS buffer. The GST protein was eluted from the beads with 10 mM reduced glutathione in 50 mM tris, pH 8.0 and dialyzed into PBS buffer+10% glycerol.

$His_6$ tagged fusions were expressed using the same protocol as described above for the GST fusions. After centrifugation, triton X-100 was added to 1% Ni-NTA beads (Qiagen) that had been equilibrated with 50 mM sodium phosphate buffer (PB)+300 mM NaCl were added to the lysate and incubated for one hour at 4° C. The beads were poured into a column, washed with 20 column volumes of PB+500 mM NaCl+0.1% triton X-100+40 mM imidazole followed by 10 column volumes of 50 mM sodium phosphate buffer (PB)+ 300 mM NaCl. The $His_6$ tagged protein was eluted from the beads with 400 mM imidazole and dialyzed into PBS buffer+ 10% glycerol.

MBP-Mdm2 was expressed in *E. coli* cells grown in rich broth (10 g tryptone, 5g yeast extract, 5g NaCl per liter)+ glucose (2g/liter)+ampicillin to an $OD_{600}$ of 0.5 and induced with 0.3 mM IPTG for 2 hours at 37° C. The cells were lysed using sonication and centrifuged at 87,000 g to remove cell debris. Amylose resin (NEB) equilibrated with column buffer (20 mM tris+200 mM NaCl+1 mM EDTA) was added to the lysate and incubated for 1 hour at 4° C. The beads were poured into a column and washed with 20 column volumes of column buffer. The MBP-Mdm2 was eluted from the beads with column buffer+10 mM maltose and dialyzed into PBS buffer+10% glycerol.

All other proteins were obtained from commercial sources including VEGF (US Biological), MBP (NEB) and Glutathione-S-transferase (Sigma). Antibodies for western blotting were provided by Prof. Stephen Johnston with the exception of mouse anti-GST (sc-138) and goat anti-VEGF (sc-152 G) which were purchased from Santa Cruz and mouse anti-Penta Histidine purchased from Qiagen.

Synthesis of Peptides. Peptides were synthesized using a Symphony peptide synthesizer (Protein Technology Incorporated) via Fmoc chemistry on Fmoc(aminoethyl)-Photolinker NovaSyn TentaGel resin (Nova Biochem). The linker is resistant to cleavage with TFA, therefore, the peptide side-chains can be deprotected with TFA without releasing the peptide from the bead. The bead-bound peptides were sequenced by automated Edman Degradation on an Applied Biosystems 476A Protein Sequencer.

Fluorescently labeled peptides were synthesized using Fmoc chemistry on Rink Amide MBHA resin (Nova Biochem). The peptides were modified at the N-terminus with 5(6)-carboxyfluorescein (Fluka) activated with HBTU (Advanced Chemtech). Peptides were cleaved from the resin with TFA and purification was performed on a Biocad Sprint HPLC. The masses of each peptide were analyzed by MALDI-TOF mass spectrometry (Voyager DE Pro—Applied Biosystems) and were within 0.1% of the predicted mass.

Phage Display. A 20 amino acid peptide library expressed at the N terminal pIII of M13 phage (named ON.543) was provided by Prof. Stephen Johnston (originally obtained from Affymax (Needels et al., 1993) and contained approximately $10^8$ different peptides. Pre1 binding peptide (PREbp) was isolated after six rounds of panning as follows. Round (RD) 1: $His_6PRE1$(40 μg) was absorbed onto an ELISA plate, incubated with $10^8$ phage in PBS (20 mM sodium phosphate, pH=7.5, and 150 mM NaCl) buffer for 2 hours at room temperature, washed 8 times with 1X PBS+0.1% tween 20, and eluted with 50 mM glycine HCl pH=2.0. Round (RD) 2: GST Pre1(80 μg) was bound to glutathione beads, incubated with $10^8$ phage from RD 1 in PBS+0.5% triton X-100 for 2 hours at 4° C., washed 4 times PBS+1% triton X-100 then twice with PBS, and eluted by cleavage with TEV protease. RD 3 GST Pre1 (40 μg) was bound to glutathione beads, incubated with $10^9$ phage from RD2 in PBS+1% triton X-100 for 2 hours at 4° C., washed 4 times with PBS+1% triton X-100+ 350 mM NaCl, then twice with PBS, and eluted by cleavage with TEV protease. RD 4 same as RD 3. RD 5 $His_6PRE1$(12 μg) was bound to Ni-NTA beads, incubated with $10^{10}$ phage from RD4 in PBS+1% triton X-100 +10 mM imidazole for 2 hours at 4° C., washed 4 times PBS+1% triton X+350 mM NaCl+20 mM imidazole, then twice with PBS, and eluted with 200 mM imidazole. RD 6 same as RD 5. After round 6, phage DNA was isolated and sequenced. Since the free synthetic peptide was insoluble, an additional six polar amino acids were added, three on each end, to enable the peptide to be displayed on beads.

CBP(378-817) binding peptide (KIXbp1) was found after four rounds of panning as follows. Round (RD) 1: GSTCBP (378-817) was absorbed onto an ELISA plate, incubated with $10^8$ phage in PBS (20 mM sodium phosphate, pH=7.5, and 150 mM NaCl) buffer for 2 hours at room temperature, washed 8 times with 1×PBS+0.1% tween 20, and eluted with 50 mM glycine HCl pH=2.0. RD 2: GSTCBP(378-817) was bound to glutathione beads, incubated with $10^9$ phage from RD1 in PBS+1% triton X-100 for 2 hours at 4° C., washed 4 times with PBS+1% triton X-100 then twice with PBS, and eluted with 20 mM glutathione in 50 mM tris-HCl, pH=8.0. RD 3 same as RD2. RD 4 GSTCBP(378-817) was bound to glutathione beads, incubated with $10^9$ phage from RD3 in PBS+1% triton X-100 for 2 hours at 4° C., washed 3 times with PBS+1% triton X-100+400 mM NaCl then twice with PBS, and eluted with 20 mM glutathione in 50 mM tris-HCl, pH=8.0. After round 4, phage DNA was isolated and sequenced.

Determination of solution binding constants. Titration experiments were monitored by fluorescence polarization spectroscopy using a PanVera Beacon 2000 instrument capable of measuring anisotropy of fluorescein-labeled molecules. Approximately 5 nM of the fluorescein-labeled peptide was added to 200 μL of PBS buffer (with the exception of VEGF; to conserve protein only 100 μL volume was used), which also contained 0.2 mg/ml bovine serum albumin and various concentrations of the target protein. The samples were incubated for 20 minutes at room temperature to allow equilibrium to be reached. The sample was then placed into the fluorescence spectrometer and the polarization of the emitted light was measured. A plot of the change in anisotropy verses the protein concentration was used to determine the dissociation constant ($K_D$).

To determine the rate of dissociation of the peptide/protein complex in solution, the fluorescein-labeled peptide and the partner protein were incubated at a protein concentration 10-fold above $K_D$. Unlabeled peptide was then added at a concentration 10- to 100-fold above the labeled protein concentration. Fluorescence anisotropy measurements were taken every 30 seconds. The anisotropy verses time was plotted and fit to a first order decay equation. In all cases, the dissociation reaction was >90% complete in the time required to mix the unlabeled peptide with the complex and return the cuvette to the spectrometer (approximately 10 seconds).

Comparing Monomeric verses Dimeric Proteins. Approximately 0.02 g of p53 peptide/tentagel was blocked with 10% milk overnight at 4° C. The beads were split into 2 tubes and 6 μM of GSTMDM2 or MBPMDM2 was added along with 1% milk. The beads were incubated 2 hours at 4° C. and then washed four times at room temperature for 5 minutes with 10 mM Tris (hydroxymethyl) aminomethane, pH=8.0,150 mM NaCl, and 0.1% tween 20 (TBST buffer) and then two times with 20 mM sodium phosphate, pH=7.5, and 150 mM NaCl (PBS buffer). After washing, each sample was aliquoted into three tubes with excess buffer (15 mL PBS) added to tubes 2 and 3 and exchanged every 15 minutes. The dissociation of the peptide/protein complexes was monitored at one hour and two hours. Gel loading-dye (50 mM tris base, pH=6.8, 2% sodium dodecyl sulfate, 10% glycerol, 5% β-mercaptoethanol, 0.1% bromophenol blue, and 0.1% xylene cyanol) was added directly to the beads, which were then boiled. After cooling, the supernatant was loaded onto a SDS (sodium dodecyl sulfate) polyacrylamide gel and analyzed by western blotting.

The same procedure above was carried out for GST-KIX and $His_6KIX$ at a protein concentration of 300 nM with the exception that BSA (3% for blocking and 0.3% for binding) was used instead of milk.

Dissociation of protein from peptide on Tentagel beads. Approximately 0.02 g of peptide/Tentagel beads were blocked with 10% milk (except PRE1bp was blocked with 3% BSA) overnight at 4° C. One tenth of the beads were aliquoted and set aside to be used as a control (tube #10). To the remaining beads, target protein (500 μL of a 300 nM solution) was added along with 1% milk (or 3% BSA+1% triton X-100 for PRE1) and allowed to bind for 2 hours at 4° C. The beads were then washed four times at room temperature for 5 minutes with 10 mM Tris (hydroxymethyl) aminomethane, pH=8.0, 150 mM NaCl, and 0.1% tween 20 (TBST buffer) and then two times with 20 mM phosphate, pH=7.5, and 150 mM NaCl (PBS buffer). PRE1bp was washed four times at room temperature for 5 minutes with 20 mM phosphate, pH=7.5, 350 mM NaCl, and 1% triton X-100 and then two times with PBS buffer. The beads were then equally divided into 9 tubes and 10 or 15 mL of excess buffer was added to tubes 2-9. To control for possible rebinding of dissociated protein, to tube #10, the protein was added to the peptide on beads after the addition of excess buffer. The dissociation of the complex was monitored over a two-hour period with exchange of buffer every 15 minutes. Gel loading dye was added directly to the beads and after boiling, the supernatant was loaded onto a SDS polyacrylamide gel and analyzed by western blotting.

Capturing Dilute Proteins. Approximately 0.014 g of Tentagel beads displaying Gal80 binding peptide was blocked with 10% milk overnight at 4° C. The beads were divided equally into 7 tubes and incubated with 500 μL of buffer containing various amounts of $His_6Gal80$ protein (5 to 400 ng) for 2 hours at 4° C. After washing four times with TBST buffer and twice with PBS, gel loading dye was added directly to the beads and the amount of bound His$_6$Gal80 was determined as described above. A second gel containing known amounts of pure His$_6$Gal80 was analyzed simultaneously and was used as a standard to quantitate the amount of His$_6$Gal80 retained on the beads.

Lysate Experiment. *E. coli* lysate was prepared by growing BL21 cells to an OD$_{600}$ of 0.8. Cells were lysed by sonication in PBS buffer. After sonication, triton X-100 was added to 1%. His$_6$Gal80 was doped into the *E. coli* lysate (67 μg/mL) such that it constituted 5% of the total protein. Approximately 0.02 g of Tentagel beads on which the Gal80-binding peptide had been synthesized and deprotected were added to 300 μL of the *E. coli* lysate containing His$_6$Gal80 and incubated for 2 hours at 4° C. The beads were washed four times for ten minutes each time at 4 with PBS buffer+1% triton X-100 at 150 mM NaCl at 4° C. and then twice with PBS buffer. GSTGal4 AD (activation domain) was pre-incubated with glutathione sepharose beads and then used as a positive control to pull-down His$_6$Gal80 from the lysate under the same conditions. Gel loading dye was added directly to the beads, loaded onto a SDS polyacrylamide gel and analyzed by silver stain.

Example 2

Mixed Element Capture Agent Studies—Results

Complex half life of immobilized peptides and dimeric proteins. Peptide libraries are rich sources of protein-binding molecules and there exist many straightforward methods to screen such libraries. As mentioned in the introduction, most such screens result in the isolation of ligands that form protein complexes with K$_D$s in the μM range. To test the surface-mediated avidity concept, a collection of peptides known to bind different proteins were assembled, some homodimers and some monomers. Table 1 presents a list of equilibrium dissociation constants for the complexes used in this study. These values were determined by titrating a low level of fluorescein-labeled peptide with increasing amounts of its protein partner and monitoring the level of binding by fluorescence polarization spectroscopy (Heyduk et al., 1996). The values range from 0.3 μM for the G80BPA/Gal80 protein complex (Han and Kodadek, 2000) to 8 μM for the KIXBP1/KIX protein complex. To determine the rate of dissociation of the peptide/protein complexes in solution, a large excess of unlabeled peptide was added to the protein/fluorescent peptide complex and the time-dependent decrease in polarization of the fluorescence was monitored. As expected from the modest equilibrium dissociation constants, the half-lives of all of these complexes were all shorter than the time required to mix the solutions, which was about 10 seconds (data not shown).

Figure 6A:
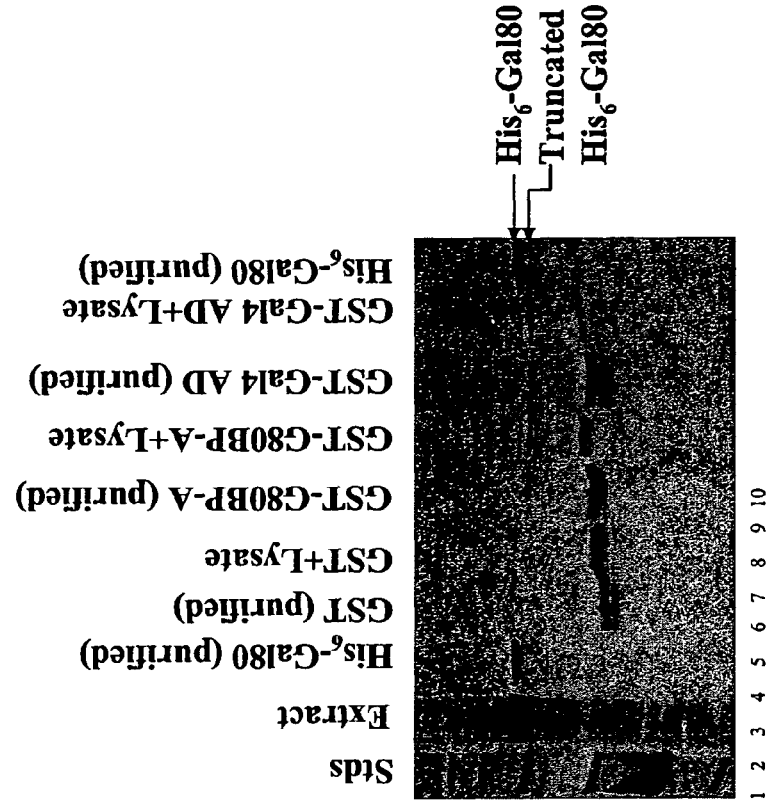
FIGS. 6A-6B illustrate an example of slow dissociation of Gal80 protein from Tentagel-bound binding peptide.

With these solution values in hand, the binding properties of the same peptides immobilized on Tentagel beads were evaluated. Each peptide was synthesized on Tentagel resin modified with an acid-stable linker, allowing deprotection of the peptide side chains without severing the link to the bead. FIG. 6A shows the protocol that was employed to evaluate the kinetic stability of the immobilized peptide/protein complexes. The complex was formed by addition of excess protein to 18 mg of peptide-coated beads. After washing, the beads were divided equally into 9 tubes and then added to a large volume of buffer (10 or 15 ml), such that if the bound protein dissociated from the bead, it would presumably be unable to re-associate due to its high dilution. To further inhibit reassociation, the buffer was also changed every 15 minutes to remove any free protein. The amount of protein remaining on the beads was monitored at fifteen-minute intervals by denaturing gel electrophoresis and Western blotting.

TABLE 1

Peptides employed in this study and the equilibrium dissociation constants (K$_D$) of the peptide/protein complexes.

| Name | Reference | Sequence | K$_D$S (μM) |
|---|---|---|---|
| Gal80bp | Han and Kodadek, 2000 | YDQDMQNNTFDDLFWKEGHR (SEQ ID NO: ID NO: 3) | 0.3 |
| Gal80bpscram | | DLQRDTNKGFHEMFDWDYQN (SEQ ID NO: ID NO: 4) | Nd |
| Pre1bp | | SHSTARGEQERAAVYLWFTYDHRSER (SEQ ID NO: ID NO: 5) | A |
| Pre1bpscram | | SEFARDLAYGEYSQHVRWTHERATSR (SEQ ID NO: ID NO: 6) | nd |
| VEGFbp | Fairbrother et al., 1998 | RGWVEICAADDYGRCLTEAQ (SEQ ID NO: ID NO: 7) | >1[b] |
| VEGFbpscram | | CQECDYWREVRGADALITGA (SEQ ID NO: ID NO: 8) | Nd |
| Mdm2bp | Kussie et al., 1996 | PLSQETFSDLWKLLPENNV (SEQ ID NO: ID NO: 9) | 2 |
| Mdm2bpscram | | NVKWLDPNQELPSFLTSLE (SEQ ID NO: ID NO: 10) | Nd |
| KIXbp1 | | SVPGSVSWFEFWSAVDAVET (SEQ ID NO: ID NO: 11) | 8 |

TABLE 1-continued

Peptides employed in this study and the equilibrium
dissociation constants ($K_D$) of the peptide/protein complexes.

| Name | Reference | Sequence | $K_D$S (µM) |
|---|---|---|---|
| KIXbp1scram | | FSASFTEVVDAGWVSPWSVE (SEQ ID NO: ID NO: 12) | Nd |

Abbreviations:
bp = binding peptide.
Nd = not determined.
Scram = scrambled.
The residues shown in bold in the Pre1 bp were added to enhance solubility. All peptide sequences are written with the N-terminus at the left end.
[a] Could not be determined due to limited solubility of the peptide.
[b] Lower limit. The true value could not be measured due to a limited amount of protein.
The peptide names indicate the protein they recognize.

Figure 6B:
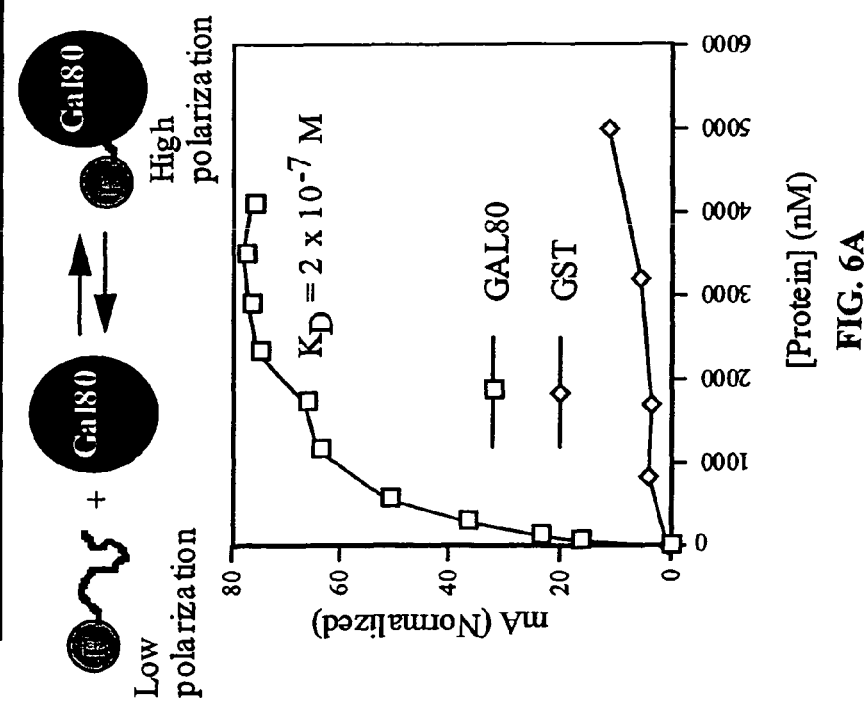

FIG. 6B shows the results of experiments that employed the Gal80, GST-Pre1 and VEGF proteins, all native dimers, as well as dimeric fusions of Mdm2 (GST-Mdm2) and KIX domain of Creb Binding Protein (GST-KIX). In the case of Gal80 protein the level of bound protein decreased to approximately 50% of the original level within 30 minutes after which the level of retained protein remained constant for at least an additional one and a half hours. This biphasic behavior was expected based on the fact that the stable Gal80 dimers associate to form tetramers with a $K_D$ in the mid to high nM range (Fancy and Kodadek 1999; Melcher and Xu, 2001). Since the beads were originally exposed to excess Gal80 at a protein concentration near or above the $K_D$ of the tetramer, it seems likely that this form of the protein was the dominant species bound, but that only one of the component dimers was in contact with the immobilized peptides. Thus, the inventors interpret these results as an initial dissociation of the Gal80 tetramer, leaving behind a tightly bound Gal80 dimer that does not dissociate from the beads during the course of the experiment. GST-Pre1, VEGF, GST-KIX and GST-Mdm2 were also bound very stably to the beads. Little, if any dissociation of these dimeric proteins was observed over the course of two hours. To ensure that these results truly represented stable, specific peptide/protein complexes, several controls were performed. Lane 10 in FIG. 6B shows the result of adding an amount of protein equal to the "t=0" level to the highly dilute bead+buffer mixture and incubating for two hours. In accordance to the procedure mentioned above, the buffer was exchange every fifteen minutes to discourage association of the free protein to the peptide immobilized on Tentagel. This control was done to assess whether the protein could re-associate with the beads in the diluted sample if it dissociated. No association of the VEGF, GST-Pre1, GST-KIX or GST-Mdm2 was observed under these conditions and only a trace of Gal80 was present. The experiment was also repeated with beads displaying a scrambled version of the binding peptide (see Table 1) and beads lacking any peptide. In each case, no bound protein was observed with the exception of a small amount of binding of the Pre1 protein to the scramble peptide that presumably represents a minor non-specific interaction. The half-lives of these immobilized peptide/protein complexes are several hours or more, an increase of at least three orders of magnitude compared to that measured in solution.

Kinetic stability of immobilized peptides with analogous monomeric and dimeric proteins. It seems likely that the huge difference between the kinetic stabilities of these peptide/protein complexes in solution and on beads is due to bidentate binding of the immobilized peptides to the dimeric proteins. However, other possibilities cannot be ruled out based on these data alone. To probe this issue further, similar experiments were carried out using dimeric and monomeric versions of the same protein.

The domain of the human Mdm2 protein represented by residues 1-188 is a structurally characterized monomer. This Mdm2 fragment is known to bind a peptide derived from the p53 activation domain (Kussie et al., 1996.). Two different Mdm2-containing fusion proteins were expressed and purified. In one, the Mdm2 domain was fused to maltose-binding protein (MBP), a monomer. In the other it was fused to GST, a native dimer. Titration experiments showed that, in solution, the p53 derived peptide bound each form of the protein with similar affinity and kinetics ($K_D$ approx. 2 µM (Table 1) with a half life of less than 10 seconds). The p53-derived peptide had no detectable affinity for GST or MBP alone (data not shown).

The kinetic stabilities of each of these complexes were then probed with the peptide immobilized on Tentagel beads, using a dilution protocol similar to that shown in FIG. 6A, except that fewer time points were taken. As shown in FIG. 8A (lanes 6-9), monomeric MBP-Mdm2 dissociated from the beads rapidly. Only a small fraction of the input protein was detectable immediately after completion of the washing steps (lane 7) and no trace of protein was detectable on the beads after a one hour incubation (lane 8). In stark contrast, little or no dissociation of the dimeric GST-Mdm2 fusion protein was observed even after two hours. Again, a dilution control demonstrated that if the protein had dissociated from the beads under these conditions, reassociation would not have occurred.

Similar experiments were also carried out with monomeric and dimeric forms of the KIX domain (Radhakrishnan et al., 1997) of the CRES-binding protein (CBP), a transcriptional coactivator. In this case, the peptide employed was isolated by phage display from a library of 20 mers (see Materials and Methods). The peptide/protein complexes (including either monomeric $His_6$-KIX or dimeric GST-KIX) exhibited $K_D$s of approximately 8 µM in solution (Table 1). However, the half-lives of the two peptide-protein complexes differed greatly when the peptide was immobilized on Tentagel. FIG. 8B (lanes 2 and 4) displays the amount of protein remaining on the beads immediately after the washing steps. Monomeric $His_6$-KIX was undetectable whereas dimeric GST-KIX was present. As was shown in FIG. 6, GST-KIX and immobilized KIXbp1 possessed a half-life in excess of two hours.

The striking differences between the half-lives of complexes containing monomeric and dimeric forms of the same proteins on the peptide-coated Tentagel beads strongly supports the idea that stable binding of native dimers is due to bidentate binding.

Figure 7:
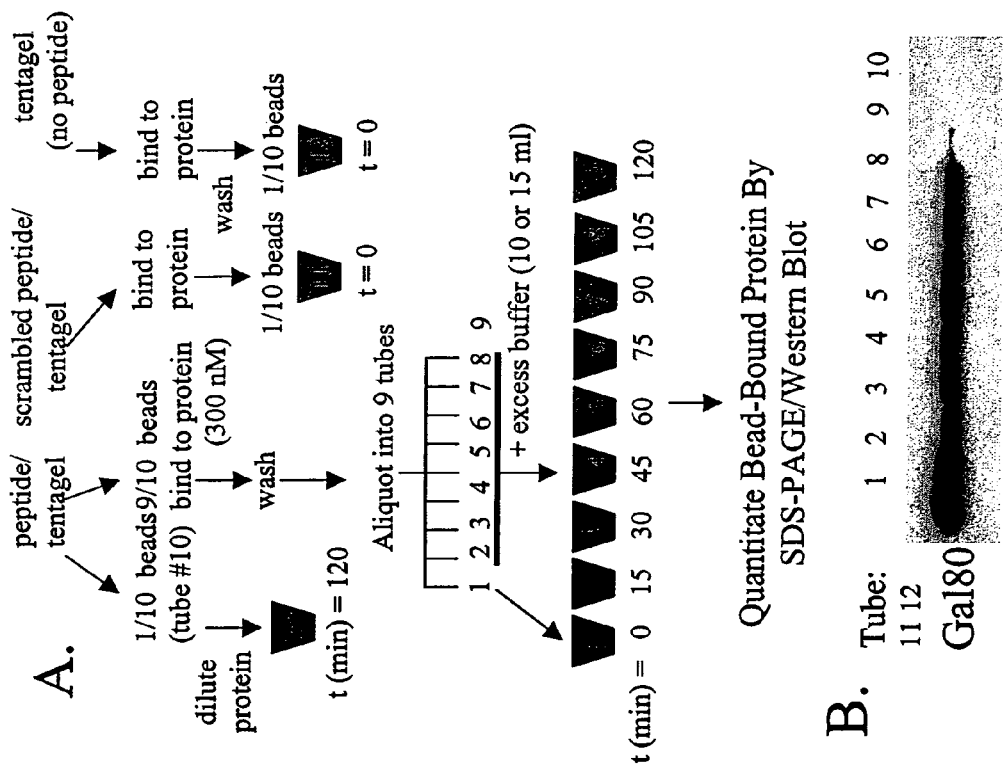
FIGS. 7A-7B illustrate an example of efficient capture of a dilute dimeric protein by immobilized peptides.

Efficient capture of dilute proteins. In all of the above examples, the protein was loaded onto the peptide-coated bead at a relatively high concentration (300 nM) prior to dilution. Since the concentration of most proteins of interest in a biological sample will be lower, it was of interest to evaluate the ability of a Tentagel-bound peptide to capture a dimeric protein from more dilute solutions. FIG. 7 shows the results of a study in which 2 mg of Gal80 bp-coated Tentagel beads (approximately 0.4 μmoles of peptide) was incubated with the indicated amounts Gal80 protein in a volume of 500 μl. After washing, the bound protein was detected by boiling the beads in denaturing loading buffer followed by SDS-PAGE/western, blot analysis of the resulting supernatant. The bottom panel in FIG. 7 shows a western blot in which known amounts of purified Gal80 were applied to the gel, allowing quantitation of the amount of protein retained by the bead-bound peptide in the experiment. The results show that a constant amount of Gal 80 protein was captured by the beads at protein concentrations ranging from 40 nM to 0.4 nM. Even at the lowest protein concentration detectable, essentially 100% of the protein was bound to the beads, as can be seen by comparing the band intensities in the experimental and calibration blots. Further dilution of the protein in this assay format exceeded the sensitivity of the western blot. This suggests that the $K_D$ of the immobilized peptide/Gal80 complex must be at least an order of magnitude lower than 0.4 nM. At all of the higher protein concentrations, a constant amount of Gal80 protein (approximately 50 ng) was retained on the beads. This must reflect the binding capacity of the beads.

Specificity of the peptide-protein interaction. In a protein-detecting array, a complex solution such as a blood sample or cell extract containing thousands of proteins would be applied to the array. For proper interpretation of the results, it is critical that the specificity of binding of the target protein to its cognate capture agent is high.

To address this point, the Gal80 bp/Gal80 pair was again employed. $His_6Gal80$ was doped into an *E. coli* lysate such that Gal80 represented 5% of the total protein concentration. This solution was then incubated with the Tentagel-bound Gal80 bp followed by thorough washing to remove any unbound material. The composition of the proteins captured by the peptide was then addressed by SDS-PAGE followed by silver staining. As shown in FIG. 5, Gal80 was the only detectable protein retained from the extract, at least at the level detectable by silver staining. No detectable proteins were retained in a control experiment using a scrambled version of Gal80 bp. To provide context for this result, the same Gal80-doped extract was applied to glutathione-sepharose-bound GST-Gal4 AD. This 34 residue fragment of Gal4 is the native ligand for Gal80 and is known to form a high affinity and specificity complex with the repressor (Johnston et al., 1987). As can be seen by comparing lanes in FIG. 5, the results obtained using the peptide and the native Gal4 AD were quite similar (the large doublet of bands near the bottom of the gel is due to the GST-Gal4 AD fusion protein that was eluted from the beads).

Figure 9:
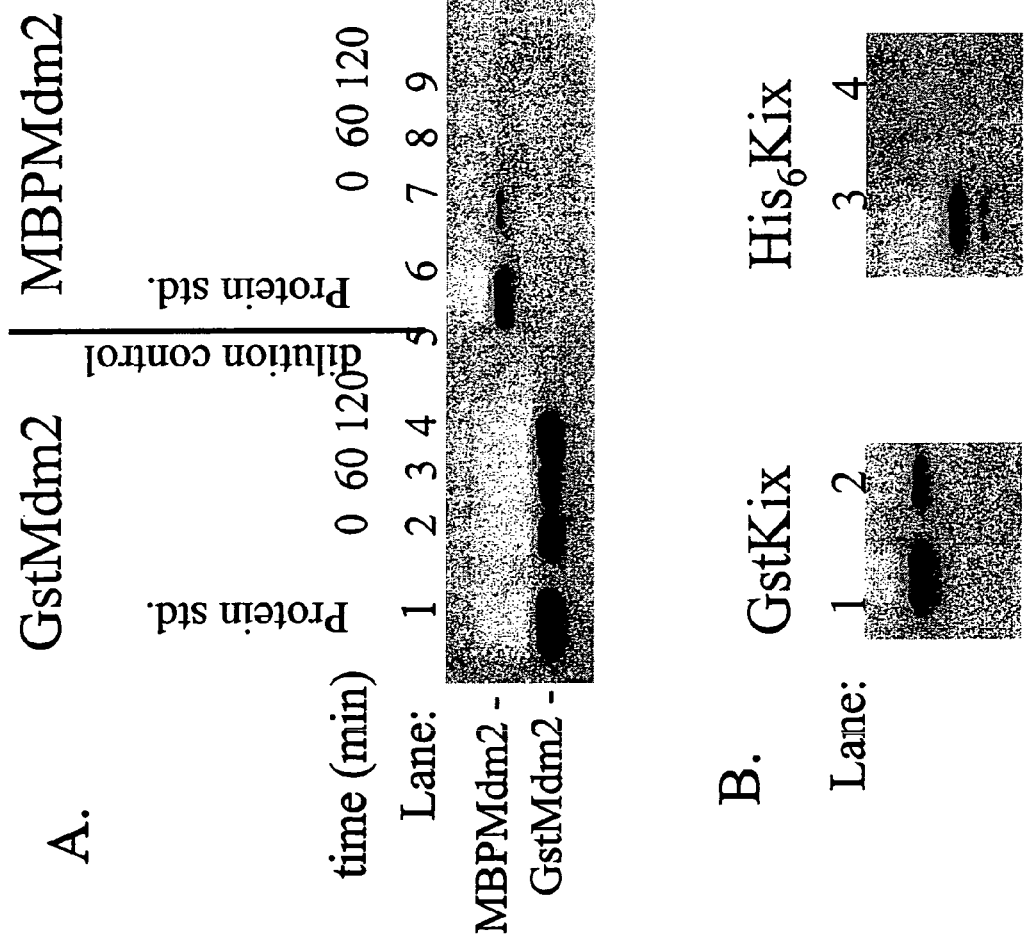
FIGS. 9A-9B illustrate exemplary results from a study using two different binding elements that bind different surfaces of a monomer (i.e., a MBP-Mdm2 fusion protein). A fluorescently labeled fusion protein was incubated under demanding conditions (high salt and detergent) with beads that displayed either a MBP-binding peptide, a Mdm2-binding peptide, or both (i.e., a MECA comprised of a single linear peptide in which the two component binding elements were linked via a single serine residue, i.e. a chimeric binding element).
Figure 10:
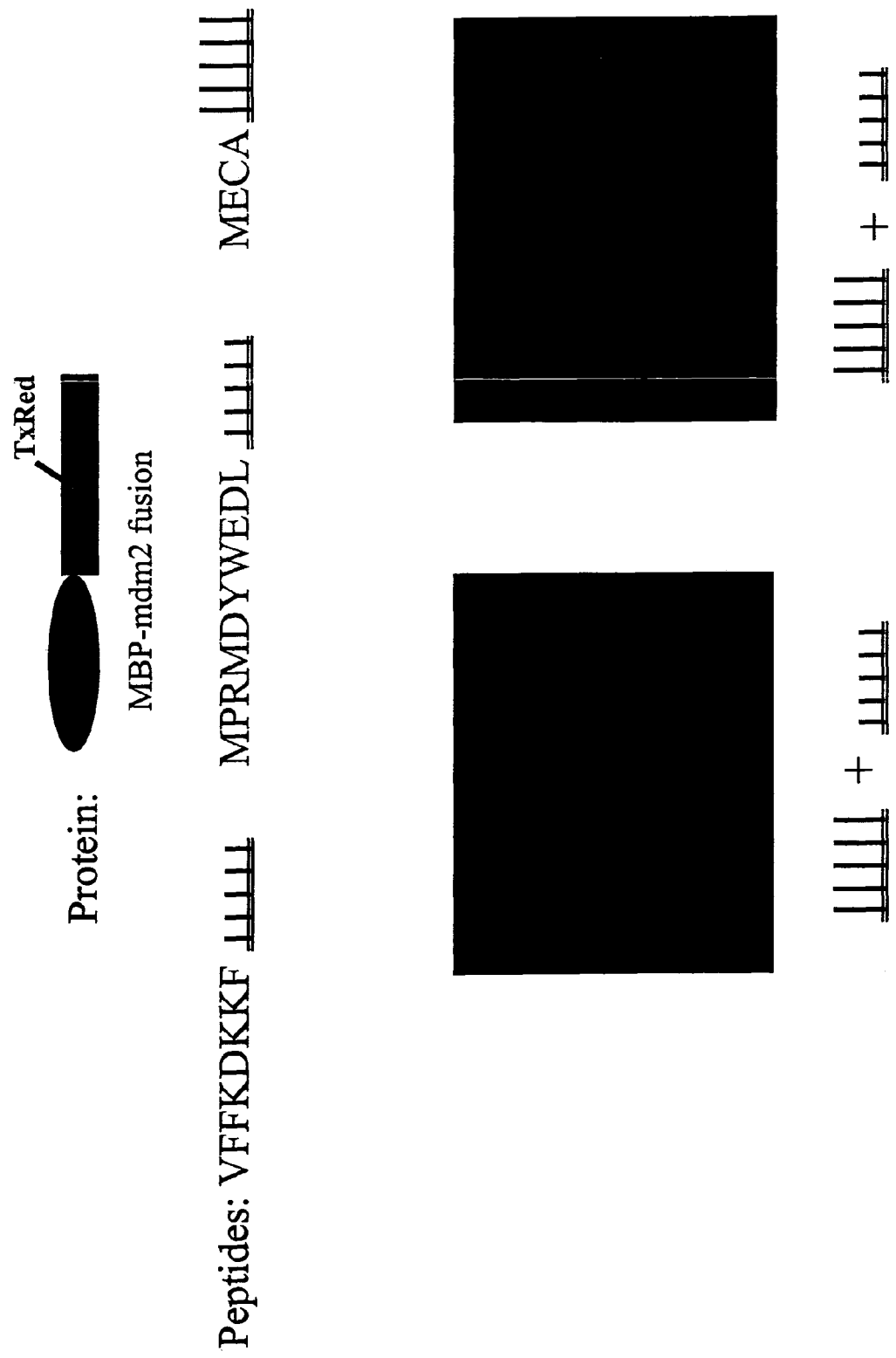
FIG. 10 is a schematic model of the presumed mode of binding of a two-domain protein (such as MBP-mdm2) to a MECA comprised of fused or chimeric binding elements. Note that 1:1 binding would be realized only in the unlikely event that the linker provided ideal geometry for bidentate interactions. This can be determined by asking if the solution $K_D$ of the MECA/protein complex is much lower than those of the individual binding element complexes.
Figure 11:
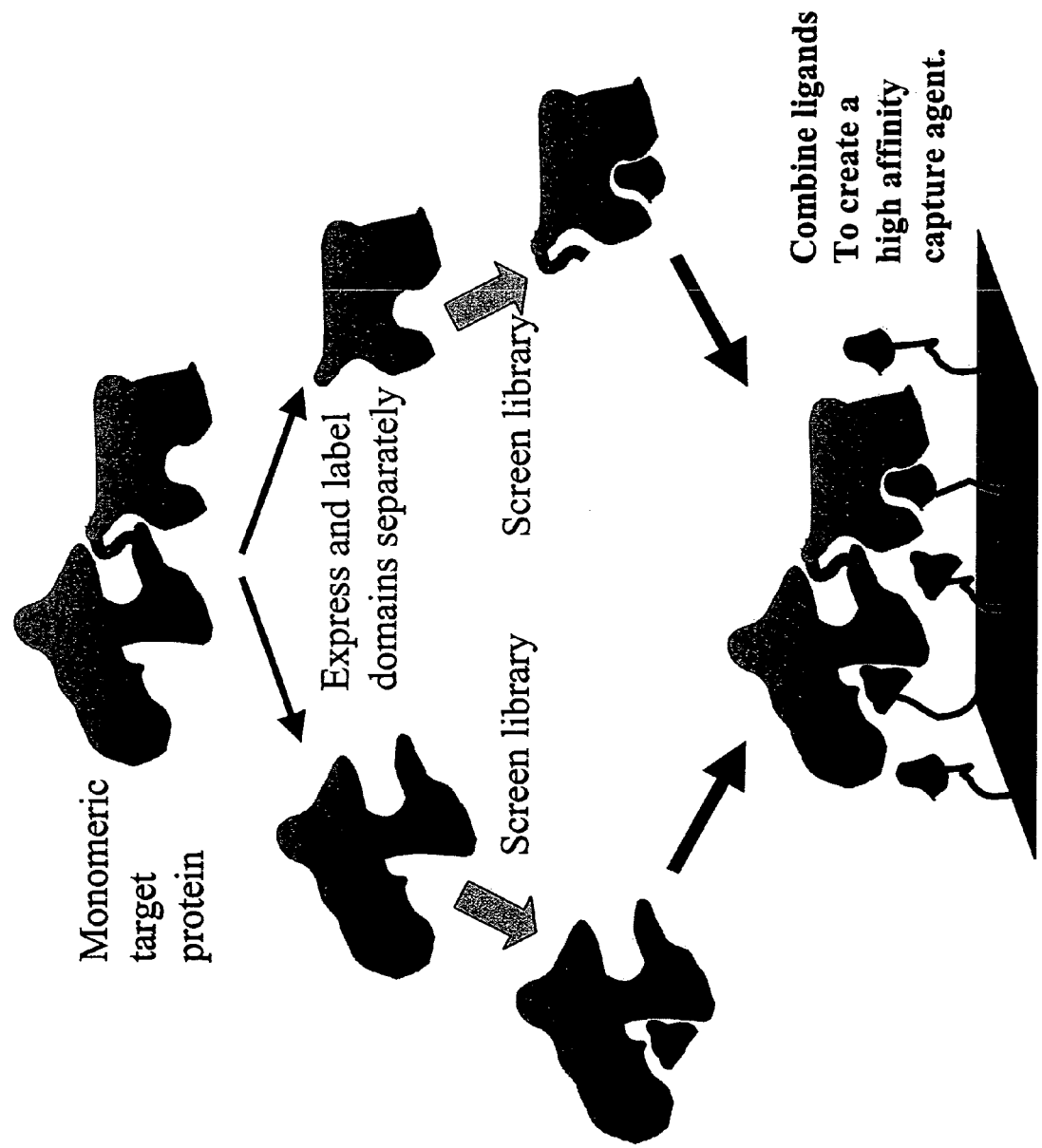
FIG. 11 is a schematic of a model for the rapid isolation of high affinity capture agents for monomeric proteins. The idea being to take advantage of the fact that most monomeric proteins are composed of separable, independently expressible domains. Two or more domains would then be combined on the support to provide a MECA for that protein.

Efficient capture of a monomeric, two domain model protein. FIGS. 9A-9B show that the MECA concept can be applied to a monomeric protein (as demonstrated by gel filtration; data not shown). Peptides that bind MBP and human mdm2 protein were identified. Each peptide/protein complex was found to have a $K_D$ in the μM range and both peptides bound a MBP-Mdm2 fusion protein with the same modest affinities (FIG. 9B). Both individual peptides bind the Texas Red-labeled fusion protein poorly under demanding conditions. However, a MECA comprised of the peptides fused together via a single intervening serine residue (a chimeric binding element) bound the protein efficiently (see FIG. 9A for a fluorescent micrograph of the two bead mixtures, showing the level of contrast). However, the MECA did not bind the fusion protein tightly in solution (FIG. 9B) exhibiting less than two-fold improvement over the individual peptides. This proves that the high affinity binding on the surface must have involved more than one immobilized molecule and the fusion protein (FIG. 10). In further support of this notion, the number of serines placed between the binding elements has no effect on the affinity of the MECA on the surface (data not shown.)

Example 3

Peptoid Library Studies—Materials and Methods

Reagents and Instrumentation. All reagents and solvents were purchased from commercial suppliers and used without further purification. TentaGel macrobeads (140-170 micron diameter; substitution: 0.51 mmol/g) were obtained from Rapp Polymere (Tübingen, Germany). Analytical HPLC was performed on a Biocad Sprint system with a C18 reverse-phase HPLC column (Vydac, Columbia, Md., 5 μM, 4.6 mm i.d.×250 mm). A gradient elution of 10-50% B in 20 minutes followed by 50-80% B in 5 minutes was used at a flow rate of 1 mL/min. (solvent A: $H_2O/0.1\%$ TFA; solvent B: $CH_3CN/0.1\%$ TFA). MALDI-TOF MS was performed on a Voyager-DE PRO biospectrometry workstation (Applied Biosystems, Foster City, Calif.) using α-hydroxy cinnamic acid as the matrix. A New Brunswick Scientific (Edison, N.J.) Innova 4400 incubator shaker was used to perform the peptoid syntheses at 37° C. Microwave-assisted peptoid syntheses were performed on a 1000W Whirlpool (Benton Harbor, Mich.) microwave oven (model MT1130SG) set to deliver 10% power. Edman sequencing of peptoids was performed on an ABI 476A Protein Sequencer (Applied Biosystems, Foster City, Calif.). The fluorescence spectra of the beads were recorded with a hyperspectral microscope constructed in the laboratory of Professor Harold Garner (UT-Southwestern) (Schultz et al., 2001). The on-bead fluorescence assays were visualized with a Nikon Eclipse TE300 fluorescence microscope equipped with a Chroma 61002 triple band filter set and a CCD camera (Preston, United Kingdom). MetaMorph software (Universal Imaging Corp., Downingtown, Pa.) was used to acquire and process the photomicrographs. Isothermal titration calorimetry (ITC) experiments were performed on a MicroCal VP-ITC instrument (Northampton, Mass.).

Syntheses of peptoid libraries at 37° C. The syntheses of 8-mer libraries were performed in standard 25 ml glass peptide synthesis reaction vessels (Chemglass, Vineland, N.J.) in an incubator shaker at 37° C. One and a half grams of TentaGel macrobeads (140-170 μm; substitution: 0.51 mmol/g) were distributed equally into 5 peptide synthesis reaction vessels, 5 ml of DMF was added and the beads were allowed to swell at room temperature for 60 minutes. The DMF was drained and 1.5 ml of 2M bromoacetic acid and 1.5 ml of 3.2M diisopropylcarbodiimide (DIC) was added to each vessel. The reaction vessels were placed on an incubator shaker set at 37° C. and 225 rpm for 40 minutes. The vessels were drained and the beads were thoroughly washed with DMF (8×3 ml). The beads in each of the vessels were treated with one of five amines (see FIG. 13) at 2M concentration and allowed to react in the shaker at 37° C. for 60 minutes. All the amines were dissolved in DMF, except 4-(2-aminoethyl)benzene sulfonamide which was dissolved in DMSO. The vessels were drained and washed thoroughly with DMF (8×3 ml). The beads in each of the reaction vessels were pooled into a large 250 ml peptide synthesis vessel, drained, suspended in 50 ml of dichloromethane/DMF (2:1) and randomized by bubbling argon for 15 minutes. The beads were distributed equally into five 25 ml peptide synthesis vessels and the procedure was repeated. The protocol was slightly modified for the final 4 residues of the library, where the displacement of the bromide by the primary amine was carried out for 90 minutes, instead of 60 minutes. In the case of the 78,125 compound library, the fourth residue from the amino terminus was fixed and thus, all the reaction vessels were treated with ethanolamine for the bromide displacement step.

Microwave-assisted peptoid library syntheses. The syntheses of 5-mer and 6-mer libraries were performed employing a microwave-assisted protocol (Olivos et al., 2002) on 1 g and 2 g of beads, respectively. In this protocol, both the acylation and bromide displacement by the primary amine were performed twice for 15 seconds in a 1000W microwave oven set to deliver 10% power. The beads were shaken manually for 30 seconds between microwave pulses to ensure proper mixing. All other steps were identical to the 37° C. procedure.

Protection and deprotection in primary amines. The functional groups in amine 1 (hydroxy), amine 3 (primary amino) and amine 7 (secondary amino) were protected following previously reported literature procedures (Uno et al., 1999; Pons et al., 1998). The following procedure was used to cleave the protecting groups at the end of the library synthesis. The beads were washed thoroughly with DMF (8×3 ml) then dichloromethane (3×3 ml), drained and treated with 6 mL of 95% TFA, 2.5% water and 2.5% anisole for 2 hours. The cleavage cocktail was drained and the beads were washed thoroughly with dichloromethane (8×3 ml). The beads were neutralized by treating with 10% diisopropylethyl amine in DMF for 5 minutes, washed with dichloromethane (5×3 ml), and dried until further use.

For re-synthesis and characterization of peptoids by HPLC and MALDI-TOF, syntheses were performed on 50 mg of Fmoc-Rink amide MHBA resin (substitution: 0.73 mmol/g; Nova Biochem, Laeufelfingen Switzerland). The beads were swollen in DMF for 30 minutes, drained, treated twice with 20% piperidine in DMF for 10 minutes (2×2 ml) and washed with DMF (8×3 mL). The peptoid sequence was constructed by the microwave-assisted protocol (Chene et al., 2000) and washed thoroughly with DMF (8×3 mL) and dichloromethane (3×3 mL). The peptoid was released from the resin with concomitant removal of protecting groups by treating the beads with 6 mL of 95% TFA, 2.5% water and 2.5% anisole for 2 hours. The suspension was filtered and the filtrate concentrated by blowing nitrogen over the solution. The concentrated filtrate was dissolved in 2 mL of 1:1 acetonitrile/water and lyophilized. The resultant solid was subjected to HPLC and MALDI-TOF analysis.

Sequencing peptoids by Edman degradation. The sequencing of peptoids was performed on an ABI 476A protein sequencer, using the FSTNML program and a standard gradient (Gradient 1). The FSTNML program was slightly modified by adding a 60 second "wait" step at the end of the cycle to enable the gradient to run slightly longer than normal.

Protein purification. Glutathione-S-Transferase (GST) was expressed in $E.\ coli$ BL21-RIL from the commercially available plasmid pGEX-2T (Amersham Biosciences, Piscataway, N.J.). The cells were grown until an $OD_{600}$ of 0.8 was reached, at which time 1 mM IPTG was added to the medium to induce protein expression. After further growth at 37° C. for 3 hrs, the cells were harvested, sonicated and centrifuged at 22,000 rpm. The cleared lysate was then incubated with glutathione-agarose beads equilibrated with PBS at 4° C. for 1 hr. The beads were washed with 10–12 volumes of PBS, packed into a column and further rinsed with PBS. GST bound to the beads was eluted with 10 mM reduced glutathione/PBS and fractions were collected and analyzed on a 12% denaturing polyacrylamide gel. The fractions containing highly purified GST were pooled and dialyzed against PBS+ 10% glycerol. The protein concentration was estimated using Coomassie Plus Protein Assay Reagent Kit using BSA as a standard. MBP-mdm2 was overexpressed from pMAL-mdm2 in BL21-RIL cells (Bachawat-Sikder and Kadadek; 2003). Herein, the conditions were slightly modified; cells were grown in the presence of 0.2% glucose and induced at $OD_{600nm}=0.5$ with 0.3 mM IPTG and grown for an additional 3 hrs. A buffer consisting of 20 mM Tris-HCl+200 mM NaCl+1 mM EDTA, pH 7.4 was used. The protein was bound to amylose resin and after thorough washing, was eluted with 10 mM maltose.

Protein labeling with Texas Red. The protein solution (preferably 2 mg/ml) was adjusted to pH 8.3 with 0.2 M $NaHCO_3$ buffer. To this 5 µl of 50 mg/ml Texas Red solution in DMF was added with mild vortexing to mix the sample. This solution was incubated with tumbling at room temperature for one hour, after which the reaction was quenched with 1.5 M hydroxylamine. Dye-conjugated protein was separated from excess dye using a desalting column. Measurement of the absorbance of the sample at 280 nm and 595 nm indicated that, on average, these conditions resulted in each protein molecule acquiring one molecule of Texas Red.

Preparation of $E.\ Coli$ lysate for screening studies. The $E.\ coli$ (BL21-RIL strain) cells were grown overnight at 37° C. in Luria broth. The cells were harvested by low speed centrifugation, washed and resuspended in sonication buffer (50 mM $NaH_2PO_4$ pH 8.0, 300 mM NaCl, 0.1% Tween 20+protease inhibitor). The cells were then sonicated and centrifuged at 22,000 rpm to remove cell debris and provide the cleared cell lysate. The concentration of the lysate was estimated using the Bradford assay with BSA as a standard.

Library screening and identification of hits. TentaGel beads (150 mg; approx. 78,000 beads) harboring the combinatorial library $X_3$-Nser-$X_4$ were swollen in TBST (50 mM Tris pH 7.4, 150 mM NaCl, 0.1% Tween 20) for 1 hour, after which they were blocked with $E.\ coli$ lysate at room temperature for one hour. The lysate was removed and the beads were incubated with 50 nM Texas Red-conjugated MBP-Mdm2 in TBST containing 1 M NaCl+1% Tween-20, in the presence of a 1000-fold excess of $E.\ coli$ lysate (assuming the average molecular mass of the proteins in the lysate to be the same as of the target protein), for one hour at room temperature. The beads were washed with TBST (6×1 mL) and visualized under a fluorescence microscope fitted with a Texas Red filter. The brightest beads were isolated manually with a pipette tip. In another experiment, 100 mg of library $X_5$ was screened for GST binding peptoid ligands. The beads were blocked with 5% milk/TBST and then incubated with 1 µM Texas Red-labeled GST in the presence of 1000-fold excess of $E.\ coli$ lysate.

After picking the putative "hits," each bead was heated in a 1% SDS solution for 20 minutes, followed by three washes with 1×PBS. They were then sequenced by Edman degradation.

Isothermal titration calorimetry (ITC). ITC experiments were conducted on a MicroCal VP-ITC instrument. For the titration, 70 µM MBP-hmdm2 or 30 µM GST in PBS+10% DMSO was taken in the sample cell. To this, 15 µl aliquots of the peptoid solution in the same buffer were added from a computer-controlled 250 µl rotating syringe. The syringe was set at 400 rpm with intervals of 3 minutes between injections to attain baseline stabilization. The heat absorbed or released accompanying the titration was recorded as differential power (DP) by the instrument software. Experiments were carried out with C values between 1 and 400. The total heat recorded was then fitted via a non-linear least-squares minimization method. Titration of the ligand solution with the buffer alone gave the heats of dilution. Titration with MBP alone was recorded under identical conditions.

Protein capture assays using TentaGel-displayed peptoids. Five milligrams of TentaGel beads (displaying the respective hit sequences, Nlys-Nbsa-Nlys-Nser-Nbsa-Npip-Nbsa-Npip-CONH$_2$ and Nbsa-Nlys-Nbsa-Npip-Nlys-CONH$_2$ or a random sequence Npip-Nser-Nbsa-Nall-Nlys-Npip-CONH$_2$) were equilibrated in phosphate-buffered saline (PBS) for 60 minutes. The buffer was removed and the beads were blocked with 2% BSA for 60 minutes to saturate any non-specific binding sites. The beads were then washed with PBS (3 times), and incubated with 500 nM (unless indicated otherwise) of a Texas Red-labeled protein (MBP-MDM2 or GST) in 2% BSA (in 1×TBST buffer), in a 300 µL volume for 60 minutes. The beads were washed with TBST six times to remove any unbound protein and photographed under a fluorescence microscope. Studies that employed native (unlabeled) proteins were performed as follows. Ten milligrams of beads displaying the peptoid were exposed to 1 µM protein in the presence of 1000-fold excess *E. coli* lysate, 0.2% Tween-20 and 0.2 M NaCl in a total volume of 2 ml at RT for 2 hrs. The beads were washed three times with TBST (20 mM Tris buffered saline+0.1% Tween-20). Ten microliters of 2×SDS-PAGE loading dye was then added directly to these beads and they were boiled for 10 mins. The entire supernatant was loaded onto a 12% denaturing polyacrylamide gel and analyzed by Western blot using anti-Mdm2 antibodies for MBP-Mdm2 and anti-GST antibodies for GST.

Dilution experiment. Fifteen milligrams TentaGel beads displaying Nbsa-Nlys-Nbsa-Npip-Nlys-CONH$_2$ were equilibrated in PBS for 60 min. The buffer was removed and the beads were incubated with *E. coli* lysate for 60 minutes to block any non-specific binding sites. The beads were washed with PBS three times and split into three Eppendorf tubes. The beads were incubated with 1 µM, 500 nM or 100 nM respectively, of Texas Red-labeled GST in the presence of a 100-fold excess of *E. coli* lysate in a 300 µL volume for 60 minutes. The beads were washed with TBST six times to remove any unbound protein and visualized under a fluorescence microscope. The experiment was also done at 10 nM protein, but little or no fluorescence above background was observed (not shown).

Example 4

Peptoid Library Studies—Results

Figure 21:
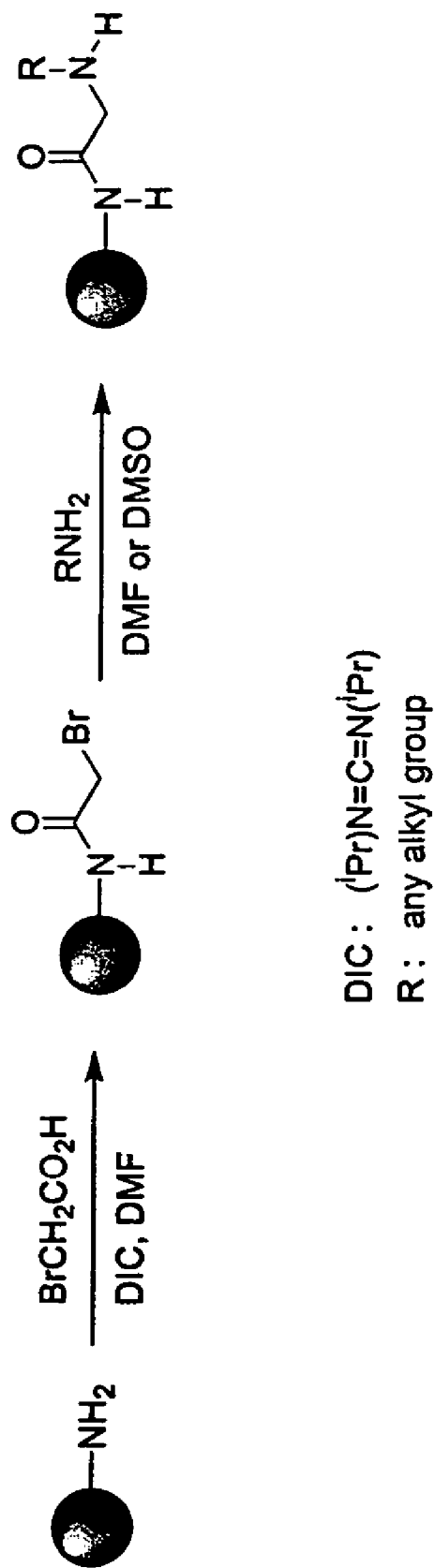
FIG. 21 illustrates an exemplary peptide sub-monomer scheme.

Synthesis and characterization of a peptoid library. One goal was to construct a peptoid library of many thousands of compounds. As a first step, some new amines were confirmed as good building blocks (for example compounds 2, 5, 8 and 11 in FIG. 12). Various other amines may work well in peptoid synthesis including, but not limited to the amines illustrated in FIG. 12 (Kirshenbaum et al., 1998; Zuckerman et al., 1994; Figliozzi et al., 1996; Wender et al., 2000; Burkoth et al., 2002). The exemplary amines shown in FIG. 12 were found to provide excellent yields in the sub-monomer protocol (FIG. 21). In each case, this was determined by the synthesis of a test pentameric peptoid in which the amine in question was used in steps two and four and residues 1, 3 and 5 were derived from the well-characterized benzylamine (Figliozzi et al., 1996). In each case, the desired pentamer was isolated in at least a 85% yield.

One aspect of the invention is the identification of compounds or binding elements capable of capturing proteins, i.e., identifying a capture agent, when immobilized on arrays. In one embodiment, the inventors screen libraries on a resin, rather than physically segregating beads and releasing the compound into solution as is generally done for chemical genetics (Clemons et al., 2001; Blackwell et al., 2001). Thus, in certain embodiments, the inventors preferred a resin with: 1) good swelling properties in organic solvents and in water to support both efficient synthesis and to provide ready access of the bound peptoids to proteins in aqueous buffer, 2) a sufficiently high loading capacity that the structure of "hits" from a screen can be determined unambiguously by direct Edman or mass spectrometry (MS)-based sequencing, eliminating the need for encoding, 3) a low fluorescence background, since the screening experiments will most conveniently be carried out with fluorescently labeled protein. PEGA, a polyacrylamide based resin, which is employed by several workers in the combinatorial chemistry field, generally satisfied these criteria. However, these beads are extremely fragile mechanically and this introduced some difficulty in the screening studies due to the large number of broken beads that were present in any given library. Therefore, the inventors preferred to employ a more stable polystyrene-based bead. After assessment of various options, TentaGel-Macrobeads (140-170 µm in diameter from Rapp Polymere) were selected as the preferred resin. While it has a hydrophobic core, the TentaGel resin is derivatized with polyethylene glycol chains that not only greatly improve the swelling of the beads in aqueous solution, but also provide a "non-sticky" surface that is ideal for reducing non-specific protein binding during screening. TentaGel beads do demonstrate an intrinsic fluorescence, which complicates screening, but is tolerable.

Figure 12:
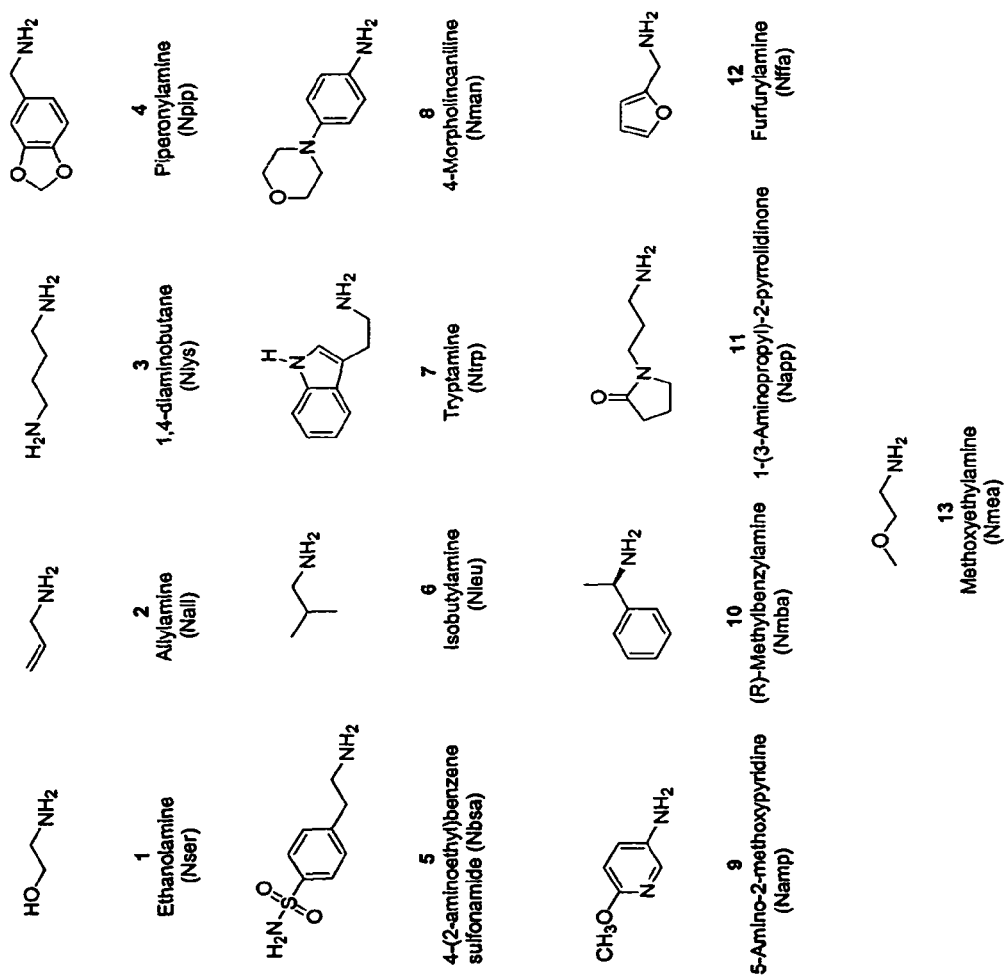
FIG. 12 is a list of exemplary amines used for the preparation of peptoid libraries. Included in brackets is the corresponding nomenclature of the peptoid units.

The initial library employed amines 1-5 of FIG. 12 and had the general formula $X_3$-Nser-$X_4$, where X represents any of the monomers derived from amines 1-5 of FIG. 12. A standard split and pool synthesis scheme (Lam et al., 1991) using 1.5 g of beads was employed to create the combinatorial library, which has a theoretical diversity of 78,125 compounds. The protocol employed to create the first four residues was a slight modification of the published sub-monomer procedure (Figliozzi et al., 1996; Kirshenbaum et al., 1998) in which the acylation step was carried out with 2 M bromoacetic acid and 3.2 M diisopropylcarbodiimide (DIC) in DMF for 40 minutes at 37° C. followed by displacement of the bromide with 2 M primary amine for one hour. For the subsequent residues, the amine addition step was allowed to proceed for 90 minutes at 37° C. All primary amines were dissolved in DMF, except 4-(2-aminoethyl)benzene sulfonamide, which was dissolved in DMSO. The resin was pooled into a 250 ml glass peptide synthesis reaction vessel, mixed by bubbling argon through the suspension for 15 minutes and split before each acylation step. At the end of the synthesis, the side chain protecting groups, if present, were removed by treating with 95% TFA, 2.5% water and 2.5% anisole for 2 hours. The resin was then neutralized with 10% DIEA in DMF, washed with DCM and dried until further use.

To determine the quality of the library, several tests were conducted. Unfortunately, the amount of compound present on a single bead is too small to allow direct characterization by HPLC or spectroscopic means, but to further address the likely purity of the library members, an 8-mer peptoid was synthesized on Rink amide MHBA resin using amines 1-5 of FIG. 12 (sequence: Nser-Nlys-Nall-Nlys-Nbsa-Npip-Nbsa-Npip-CONH$_2$). The final product was released from the beads using 95% TFA, 2.5% water, 2.5% anisole and the material was characterized by HPLC and mass spectrometry. Data indicated that the major peak in the HPLC corresponded to the expected compound. While this experiment cannot account for potential context-dependent effects in the synthesis of a combinatorial library, it does demonstrate that all of the monomers work well in the synthesis, consistent with the previous tests of each monomer using the benzyl amine assay described above.

To evaluate diversity, ten beads from the library were chosen at random and the displayed peptoids were sequenced by automated Edman degradation. Boeijen and Liskamp (1998) reported that peptoids can be sequenced by Edman chemistry using several beads as the input. However, for library screening studies, the ability to sequence a single bead is preferred. An automated approach would be even more advantageous, as it would eliminate the practical difficulties involved in handling individual beads for long periods of time, over several cycles of chemistry. A commercial peptide sequencer (ABI 476A) was adapted for the sequencing of peptoids. Although larger (400-500 μm) TentaGel macrobeads are available commercially that allow spectroscopic analysis of the compounds derived from a single bead, such beads introduce practical limitations on the size of the libraries that can be constructed and hence, were not employed in this study. The typical HPLC protocol used for sequencing peptides was modified slightly to allow the gradient to run longer. As shown in FIG. 13, when ten beads were picked from the library and subjected to Edman degradation, the derived sequence of each peptoid was different, as expected for a large, diverse library. The chromatographic traces from these sequencing runs also showed that each of the peptoids was full-length. At each step of the Edman process, only one major peak was generally observed, with the exception of a small amount of signal resulting from the previous and subsequent monomers in the peptoid, which is commonly observed in peptide sequencing using this chemistry.

Figure 14:
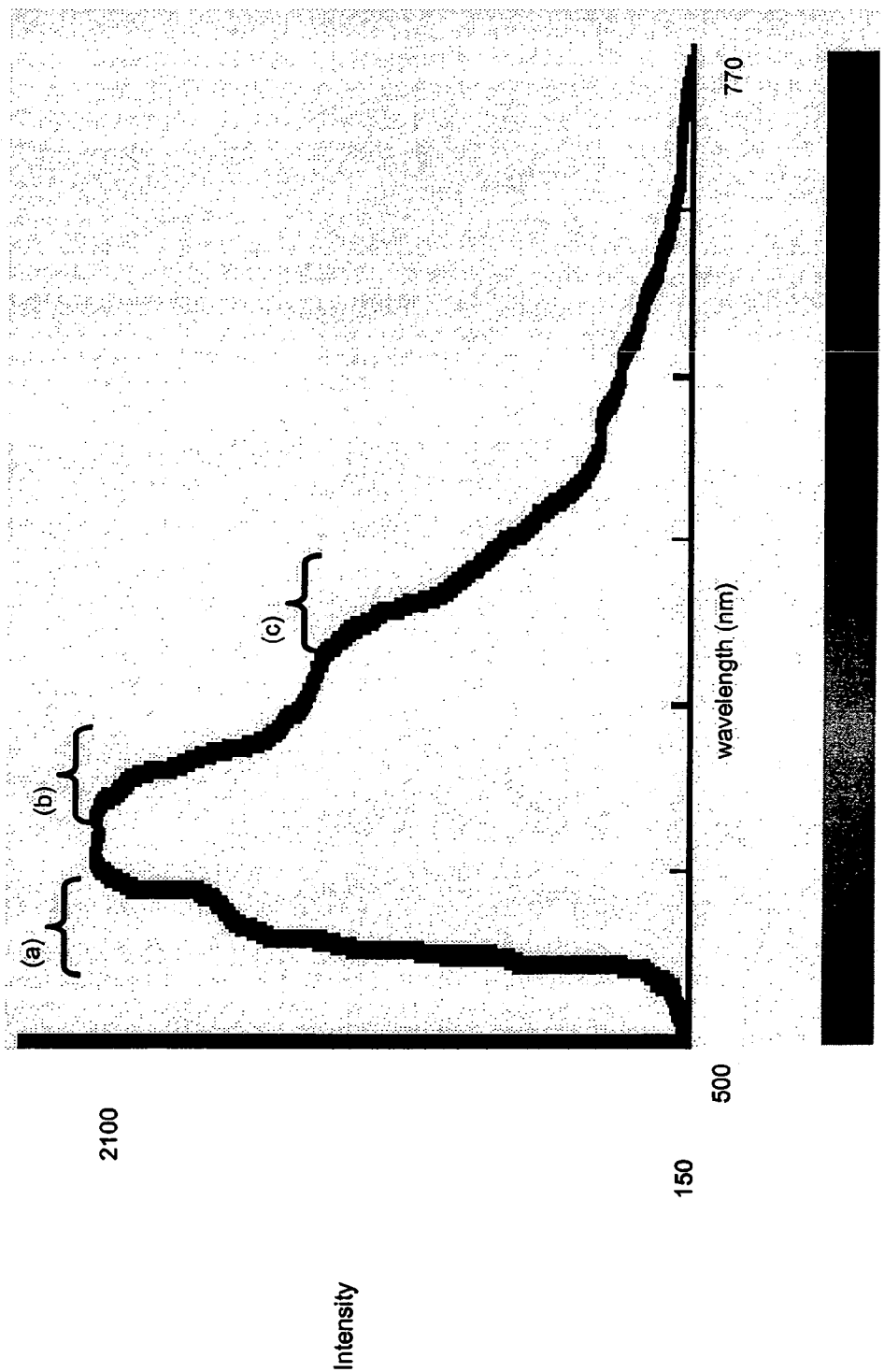
FIG. 14 illustrates the fluorescence emission spectrum of a TentaGel bead. Excitation: 460-490 nm. Emission of some fluorescent dyes: (a) Fluorescein, (b) Tetramethylrhodamine, and (c) Texas Red.

Isolation of Mdm2-binding peptoids from the library. With a high quality peptoid library in hand, the inventors developed appropriate conditions for on-bead screening. To facilitate future efforts to automate screening using a fluorescence-activated bead sorter fluorescently labeled proteins were to be employed in screening. However, TentaGel resin had an intrinsic fluorescence, particularly in the green region of the spectrum (FIG. 14). This "background fluorescence" rendered the use of many organic dyes, such as fluorescein, impractical for screening with TentaGel resin. However, the intensity of the bead fluorescence dropped significantly in the red region of the spectrum. Thus, Texas Red-labeled proteins were evaluated as potential targets in the screening process.

The human Mdm2 protein is a negative regulator of p53 function and a potential anti-cancer drug target. A fragment of Mdm2 (residues 1-188) was fused to maltose-binding protein (MBP) and used as an initial target, since this fusion protein expressed at higher levels than the Mdm2 fragment alone. This region of Mdm2 includes the region of the native protein that binds the p53 activation domain (Kussie et al., 1996) and there have been several previous reports of isolation of a peptide or small molecule ligands for this region of Mdm2 (Stoll et al., 2001; Bottger et al., 1997; Chene et al., 2000). Thus, the inventors suspected that this protein would represent a reasonable target for the initial peptoid library screening studies.

Detailed screening conditions are describe above. In general, it was found to be optimal to employ challenging conditions in order to eliminate low affinity or low specificity hits. For example, the use of a high salt- and detergent-containing buffers (1M NaCl and 1% Tween-20) are preferred. The concentration of the Texas Red-labeled protein was only 50 nM since studies conducted at higher protein concentrations indicated that a larger fraction of the library registered as "hits," presumably representing weaker ligands. A 1,000-fold excess (based on mass) of cleared E. coli lysate was used in order to demand high specificity. Screening experiments that employed only a single competitor protein such as bovine serum albumin (BSA) provided poorer results.

Figure 15:
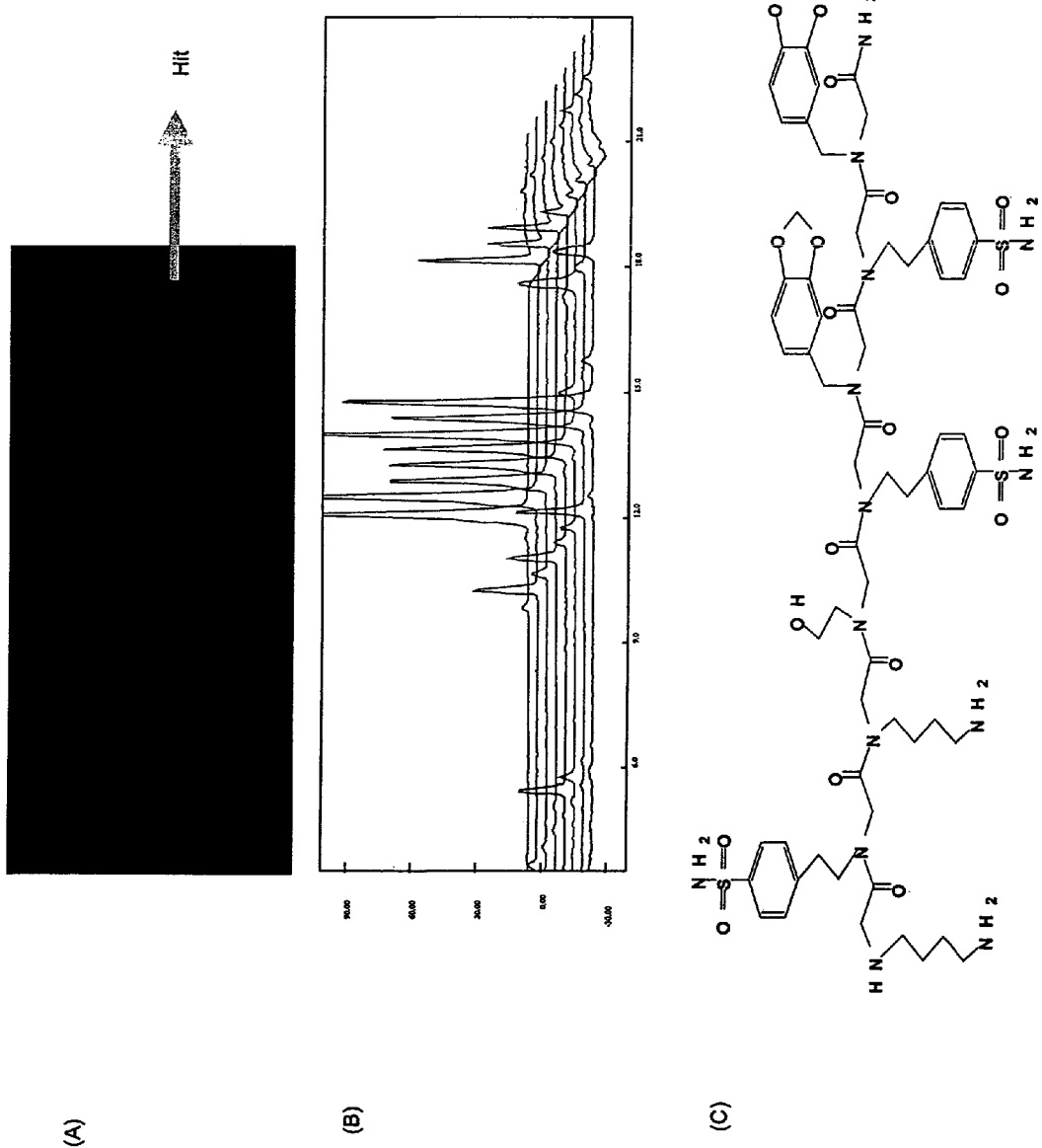
FIGS. 15A-15C show isolation of a putative peptoid ligand for MBP-Mdm2.

After incubating the labeled maltose-binding protein MBP-Mdm2 fusion protein with the bead library for one hour under these conditions and then washing the beads six times with the same buffer, beads that exhibited above background fluorescence were identified visually using a fluorescence microscope. FIG. 15 shows a photomicrograph of a field containing a bead that was scored as a hit. This bead (marked with the arrow in the figure) is clearly brighter than the surrounding beads, but that all of the others are far from dark. This is, in part, a reflection of the intrinsic fluorescence of the beads (FIG. 14) as well as the low level, non-specific binding of some of the labeled protein to many beads in the library, despite the presence of high levels of competitor. Fortunately, while this background is annoying and reduces the speed at which libraries can be screened visually, it is tolerable. Eleven hits (approximately 0.014% of the input beads) with a fluorescence well above background were identified.

To identify the sequence of each peptoid hit, bright beads were picked manually using a pipette. The individual beads were then heated to 95° C. in 1% SDS and placed in the chamber of an automated Edman sequencer. Some consensus was observed among the hits at positions 1, 2 and 8. The Edman sequencing trace of the brightest bead among the eleven hits is shown in FIG. 15B, which clearly identified its sequence (FIG. 15C).

Validation of the putative Mdm2 ligands. An issue in any library screening experiment is to validate the resynthesized ligands. Bead library-derived ligands often fail in typical solution binding assays for many reasons. For example, avidity or context effects unique to the solid surface on which the library was constructed could allow it to work well on resin but behave poorly in solution binding assays. Even more problematic is the possibility that the true ligand might have been a minor component on the bead due to some sort of side reaction during the synthesis and is not the compound expected from the sequencing data.

Figure 16:
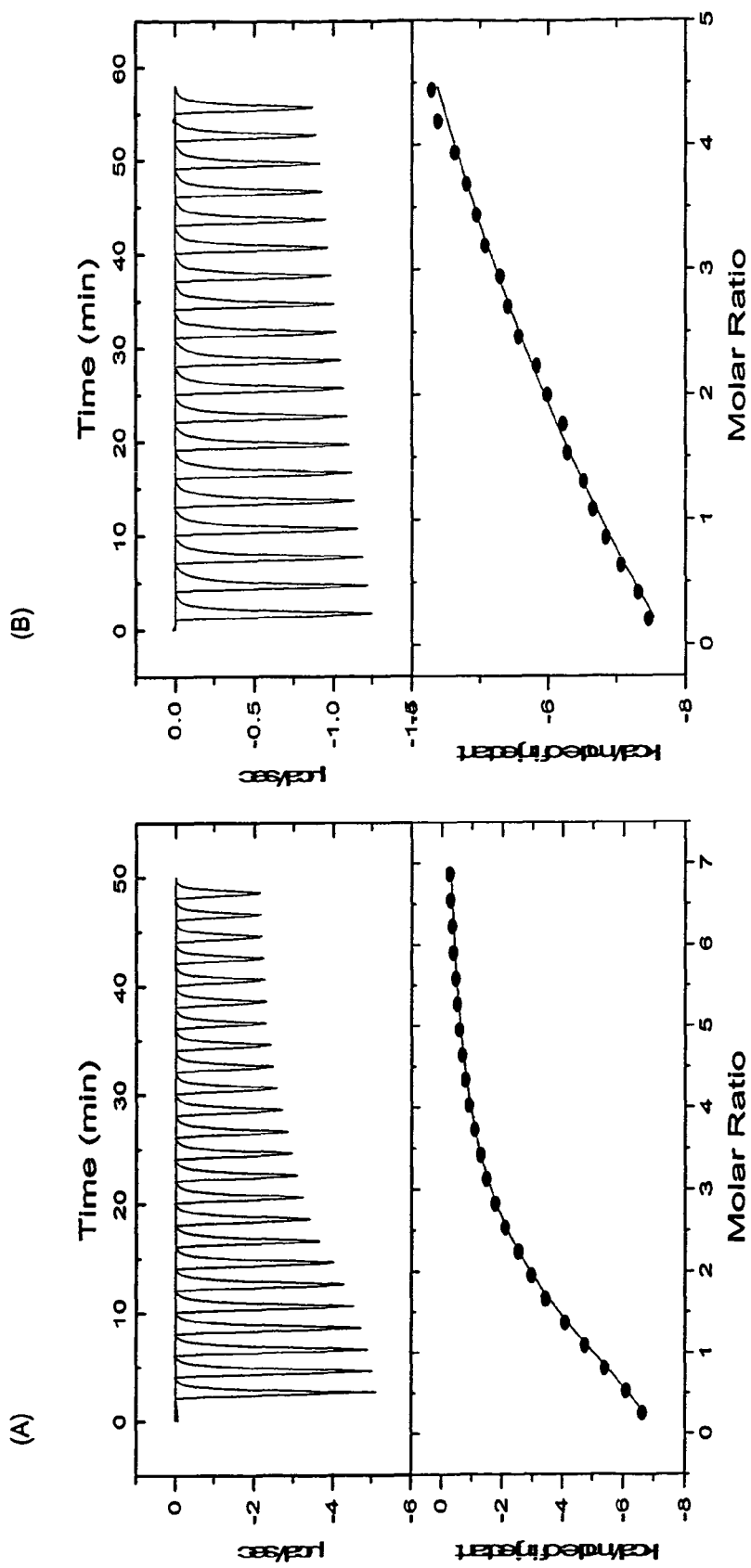

The putative hit (see FIG. 15C) was resynthesized on Rink resin, cleaved and purified to apparent homogeneity by HPLC. Binding of the synthetic peptoid to MBP-Mdm2 was then analyzed by isothermal titration calorimetry (ITC) (Leavitt and Freire, 2001). The data (see FIG. 16A) indicated an equilibrium dissociation constant of 37 μM. When the titration experiment was repeated with MBP, little or no binding was observed (FIG. 16B). This observation both suggests that the peptoid ligand isolated is specific and that it recognizes the Mdm2-derived domain of the MBP-Mdm2 fusion protein against which it had been selected.

Figure 17:
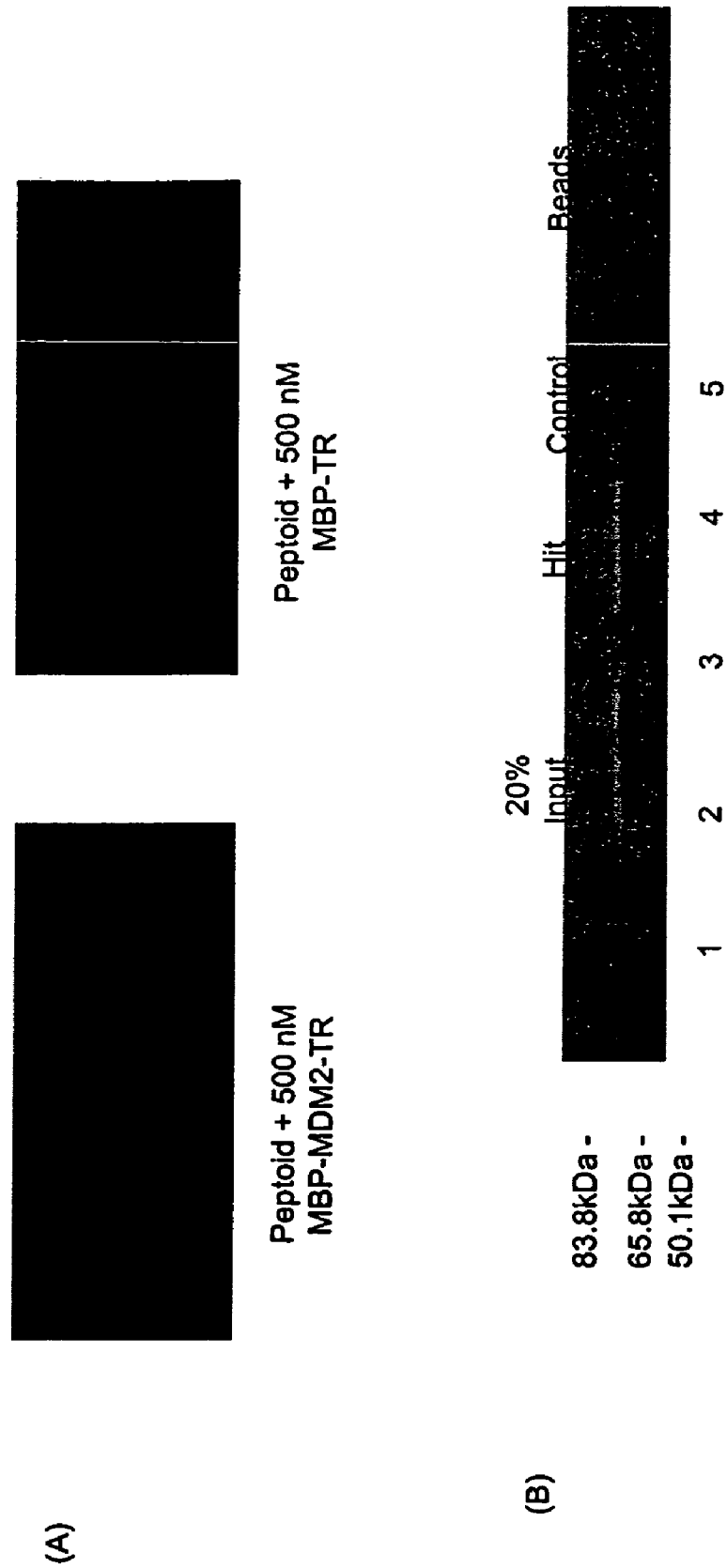
FIGS. 17A-17B show characterization of the on-resin binding properties of the Mdm2-binding peptoid.

Given the goal of constructing protein-detecting microarrays based on peptoids or other synthetic compounds, it was of even greater interest to us to determine the binding properties of the resynthesized compound when affixed to a solid surface. To this end the experiments shown in FIG. 17 were carried out. First, the hit was resynthesized on TentaGel and the protecting groups removed without removing the peptoid from the bead. It was then incubated with either Texas Red-labeled MBP-Mdm2 or Texas Red-labeled MBP at the protein concentration indicated in the figure in the presence of 2% bovine serum albumin (BSA) as competitor. As shown in FIG. 17A, the beads captured the MBP-Mdm2 protein efficiently, while little MBP binding was observed. This corroborates the ITC data. To eliminate the possibility that the Texas Red label contributes significantly to binding of the protein to the immobilized peptoid, a study was conducted using native MBP-Mdm2. Unlabeled protein was incubated with the peptoid hit on TentaGel beads in the presence of a 1000-fold excess of *E. coli* proteins. The beads were then pelleted and washed. As shown in FIG. 17B, lane 3, SDS-PAGE/Western blot analysis revealed that the immobilized peptoid had retained about 10% of the MBP-Mdm2 protein present (note that the protein was present in molar excess over the peptoid, so complete retention of the input was not possible). No detectable MBP-Mdm2 protein was retained when this study was repeated with a random peptoid, (lane 4) or TentaGel beads lacking a displayed peptoid (lane 5). The peptoid selected in the library screen is an Mdm2-binding compound capable of capturing the protein from complex mixtures such as model cell extracts.

Larger, chemically diverse peptoid libraries. The inventors have constructed larger and/or more chemically diverse libraries to support future larger scale screening against various other protein targets. As before, standard split/pool synthesis (Lam et al., 1991) on TentaGel was employed. The first library utilized amines 3-6 and 8-13 of FIG. 12 and consisted of five residue peptoids, providing a theoretical diversity of 100,000 compounds. While not much larger than the 78,125 member library discussed above, this library is far more diverse chemically, since 10 different amines were employed in its construction, with each position randomized. The second library employed only five monomers, but was longer, consisting of randomized octamers, providing a theoretical diversity of 390,625 compounds. Finally, an extremely large library of randomized hexamers was made using nine different amines, providing a theoretical diversity of 531,441 compounds.

All of these libraries were characterized for quality in the same way as described above for the 78,125 compound library. Some of the data for the largest of the libraries are presented in FIG. 18A. FIG. 18A shows the results of sequencing 10 beads chosen at random from the library. As expected, all were different. The Edman traces again suggested that full-length peptoids were obtained in each case (FIG. 18B). Two mixed sequence hexamers, Ntrp-Nmea-Npip-Nlys-Nffa-Nmba-CONH$_2$ and Nbsa-Nleu-Napp-Nffa-Nmea-Npip-CONH$_2$, were synthesized and shown by HPLC to be >85% pure. Between them, these hexamers contain all of the monomers that were subsequently employed in the library construction. The results again suggest that in the absence of unexpected context effects, all of the coupling steps proceed in high yield.

Figure 19:
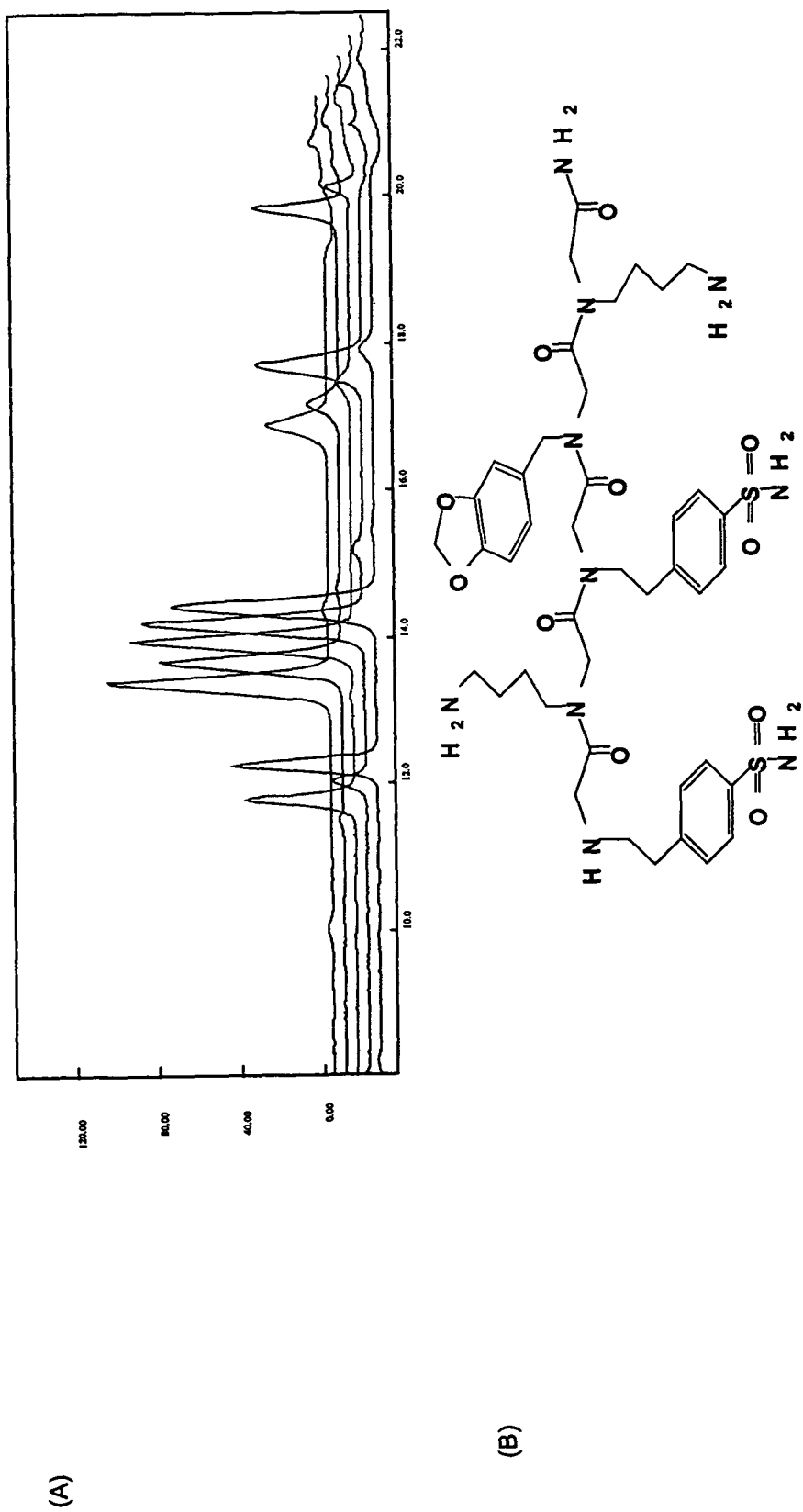
FIGS. 19A-19B show identification of a GST-binding peptoid from a library of 100,000 pentamers.
Figure 20:
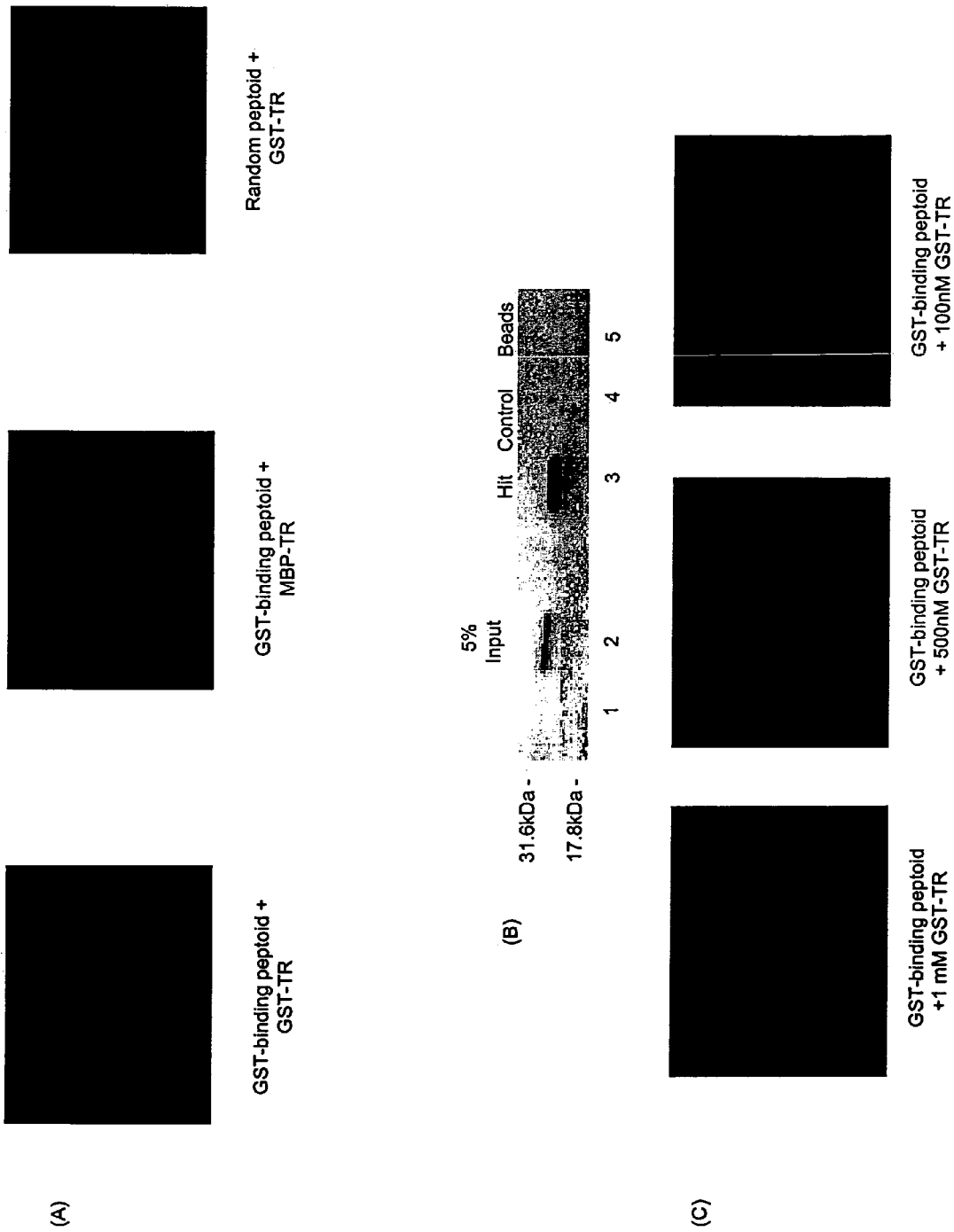
FIGS. 20A-20C show characterization of the on-bead binding properties of the peptoid obtained in the screen against GST.

To determine if these libraries would be facile sources of protein ligands or binding elements as well, part of the 100,000 compound library was screened against Texas Red-labeled GST using conditions similar to those described above except that lower salt and detergent concentrations were employed. Of the approximately 50,000 beads used in this screen, (0.5% of total population) displayed red fluorescence well above the background. One of the brightest beads was picked and the peptoid sequence determined by Edman degradation to be Nbsa-Nlys-Nbsa-Npip-Nlys-CONH$_2$ (FIG. 19). Since the primary interest is in evaluating the ligands or binding elements isolated from these screens for their ability to retain proteins from biological samples when attached to a surface, a number of on bead assays were conducted with Nbsa-Nlys-Nbsa-Npip-Nlys-CONH$_2$ (FIG. 20). As shown in FIG. 20A, the resynthesized compound retained Texas Red-labeled GST, but not a control protein (MBP) when immobilized on TentaGel. Furthermore, unlabeled GST was retained by the TentaGel-peptoid beads in the presence of a 1000-fold excess of *E. coli* extract (FIG. 20B). As shown in FIG. 20C, this was the case using GST concentrations of 1 µM to 100 nM. When the protein concentration was 10 nM, little or no fluorescence above background was observed (not shown). Finally, solution binding studies were performed employing isothermal titration calorimetry (ITC) resulting in an equilibrium dissociation constant of 62 µM for the peptoid/protein complex.

Example 5

Chimeric Binding Element Studies

Semi-Automated Screening of a Library. Stoll et al. previously reported that the chalcone general formula 1 (FIG. 22) associates with the p53-binding domain of the proto-oncoprotein Mdm2 weakly ($K_D$=220 µM) (Stoll et al., 2001). A structural model derived from NMR data (Stoll et al., 2001) suggested that the carboxylate group of the chalcone was oriented away from the protein and could be utilized for attachment to other moieties. The inventors employed chalcone (i.e., as a first binding element of a chimeric binding element) as a test case for a screening strategy to identify chimeric binding elements for use in compositions and methods of the present invention. A combinatorial library of peptoids (Figliozzi et al., 1996; Kirshenbaum et al., 1998; Burkoth et al., 2002) was synthesized by split and pool solid phase synthesis (Lam et al., 1991) using the five amines pictured in FIG. 22. This library contains 78,125 ($5^7$) different compounds. The library has seven positions that were randomized completely, a central Nser (see FIG. 22 for nomenclature) unit and two constant Npip residues between the library and the polyethylene glycol layer that coats the surface of the Tentagel bead. The Npip-Npip linker was included to facilitate eventual identification of hits since these are identified by Edman degradation and the quality of the sequence falls off drastically close to the polyethylene glycol layer. Enough beads were employed in the split and pool chemistry that each compound should be represented approximately ten times in the library.

Figure 22:
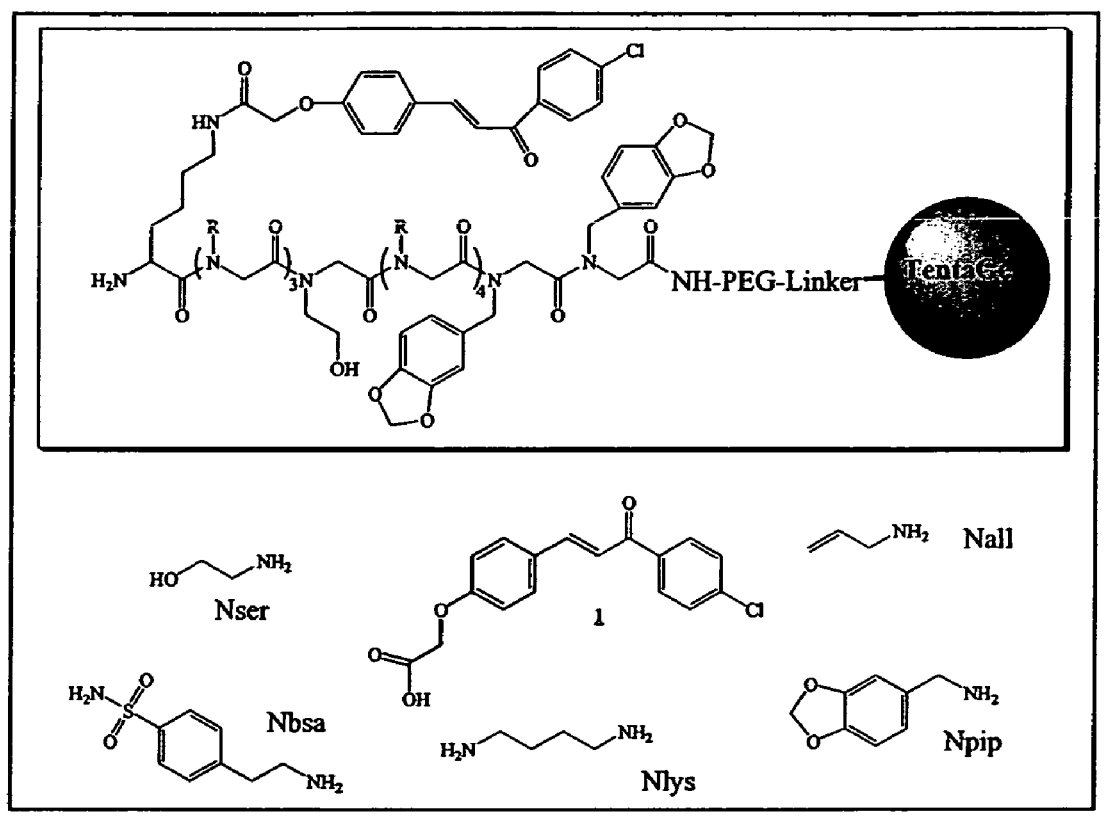
FIG. 22 illustrates at the top: a structure of the chalcone-capped peptoid library. The linker consisted of a long polyethylene glycol chain to minimize non-specific protein binding. At the bottom: amines used for the synthesis of the library along with their designations.

To make a chalcone-capped library, approximately 10% (=78,000 beads) of the aforementioned library (with side chain protecting groups intact) was capped at its N-terminal end with a lysine residue modified with chalcone formula 1 via a side chain amide bond (FIG. 22). The protecting groups were then removed to provide the desired library ready for screening.

Figures 23A, 23B, 23C:
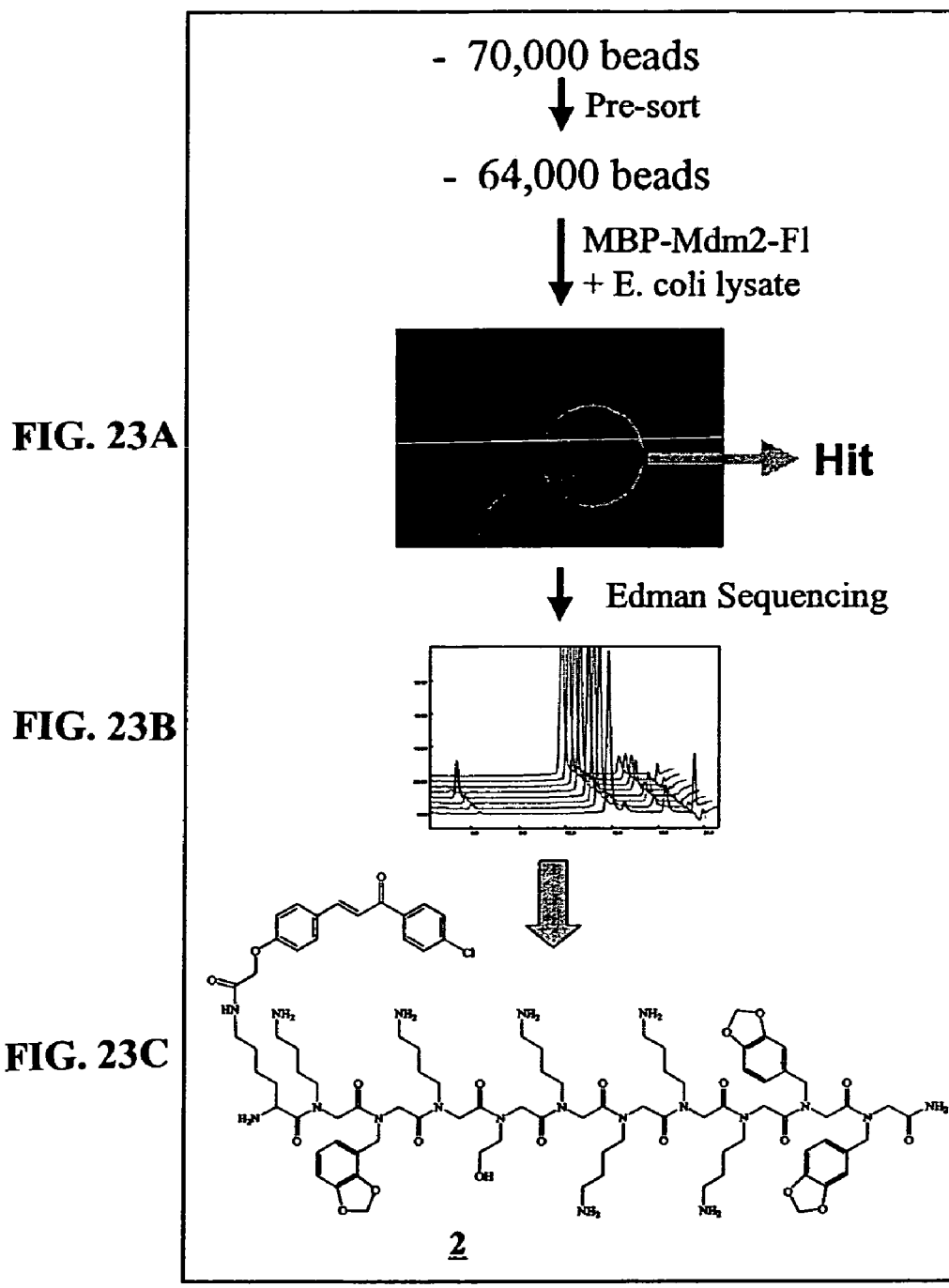
FIGS. 23A-23C illustrate a sequence of experiments leading to the identification of MBP-MDM2 chimeric binding element.

Approximately 78,000 beads was pre-sorted using a fluorescent bead sorter (COPAS SELECT 500 from Union Biometrica, Inc., Somerville, Mass.) to remove beads that exhibited intense autofluorescence. The remaining 66,862 beads were then incubated with fluorescein-labeled MBP-Mdm2 protein under conditions that were too demanding for the chalcone alone to support detectable binding of the labeled protein to a bead (500 nM MBP-Mdm2+10,000-fold excess of *E. coli* lysate in TBST+1M NaCl+1% Tween-20). After a two-hour incubation followed by thorough washing, the beads were then poured into the COPAS instrument and sorted by fluorescence intensity. Only four beads (0.00598% of the library) exhibited fluorescent well above the background. These were collected by the sorter. This low hit rate suggested that the conditions employed had indeed selected stringently for the best ligands in the library. To validate that the instrument had identified the appropriate beads, one of the "hits" was placed on a microscope slide along with several of the "negative" beads from the sort. A fluorescence micrograph of part of this field is shown in FIG. 23. The identity of the compounds on each of the four beads was determined by automated Edman sequencing. Two of the four were identical, having the structure: NH$_2$-Lys(Chalcone)-<u>Nlys</u>-Npip-Nlys-Nser-<u>Nlys</u>-<u>Nlys</u>-<u>Nlys</u>-<u>Nlys</u>-Npip-Npip (residues that were varied in the library are underlined) (FIG. 23). The other two hits (NH$_2$-Lys(Chalcone)-<u>Npip</u>-<u>Nser</u>-<u>Nlys</u>-Nser-Npip-<u>Nlys</u>-<u>Nlys</u>-<u>Nlys</u>-Npip-Npip and NH$_2$-Lys(Chalcone)-<u>Nlys</u>-<u>Nlys</u>-<u>Nbsa</u>-Nser-<u>Nall</u>-<u>Nlys</u>-<u>Nlys</u>-Npip-Npip, were also Nlys-rich, indicating that a highly basic peptide facilitates higher affinity binding to the target protein.

Binding studies confirm high affinity Mdm2/MECA binding. NH$_2$-Lys(Chalcone)-Nlys-Npip-Nlys-Nser-Nlys-Nlys-Nlys-Nlys-Npip-Npip (formula 2) was resynthesized and purified by reverse-phase HPLC. Titration experiments using MBP-Mdm2 monitored by isothermal calorimetry (ITC) revealed a solution equilibrium dissociation constant of 1.3 (±0.4) μM. The K$_D$ of the chalcone formula 1/MBP-Mdm2 complex was not able to be determined under the same conditions by ITC due to insufficient solubility of the small molecule. However, under conditions used by the inventor, the K$_D$ must be at least the reported 220 μM or higher. Therefore, the ITC data indicate an improvement of at least 170-fold in the affinity of the chalcone-peptoid chimera formula 2 relative to the parent compound formula 1. Interestingly, the K$_D$ of the complex of MBP-Mdm2 and the peptoid NH$_2$-Nlys-Npip-Nlys-Nser-Nlys-Nlys-Nlys-Nlys-Npip-Npip lacking the chalcone cap was poor (378 μM, FIG. 24B), demonstrating that neither piece of the binding element is itself a high affinity capture agent. An ITC experiment was also done with chimera formula 2 and MBP lacking the Mdm2 fusion. Only the heat of dilution of the titrant was observed in this experiment (FIG. 24C), demonstrating little or no binding (K$_D$>6 mM). These data demonstrate that interactions between formula 2 and MBP contribute little or nothing to the observed binding affinity and that the MECA derived from the chimeric binding element is specific for Mdm2.

It is also interesting to note that the same library employed above, but lacking the Chalcone-Lys cap, was screened against MBP-Mdm2 under less demanding conditions and a completely different set of peptoid sequences was isolated, strengthening the idea that the binding element of formula 2 is a unique species that is greater than the sum of its parts.

Figures 24A, 24B, 24C, 24D, 24E, 24F:
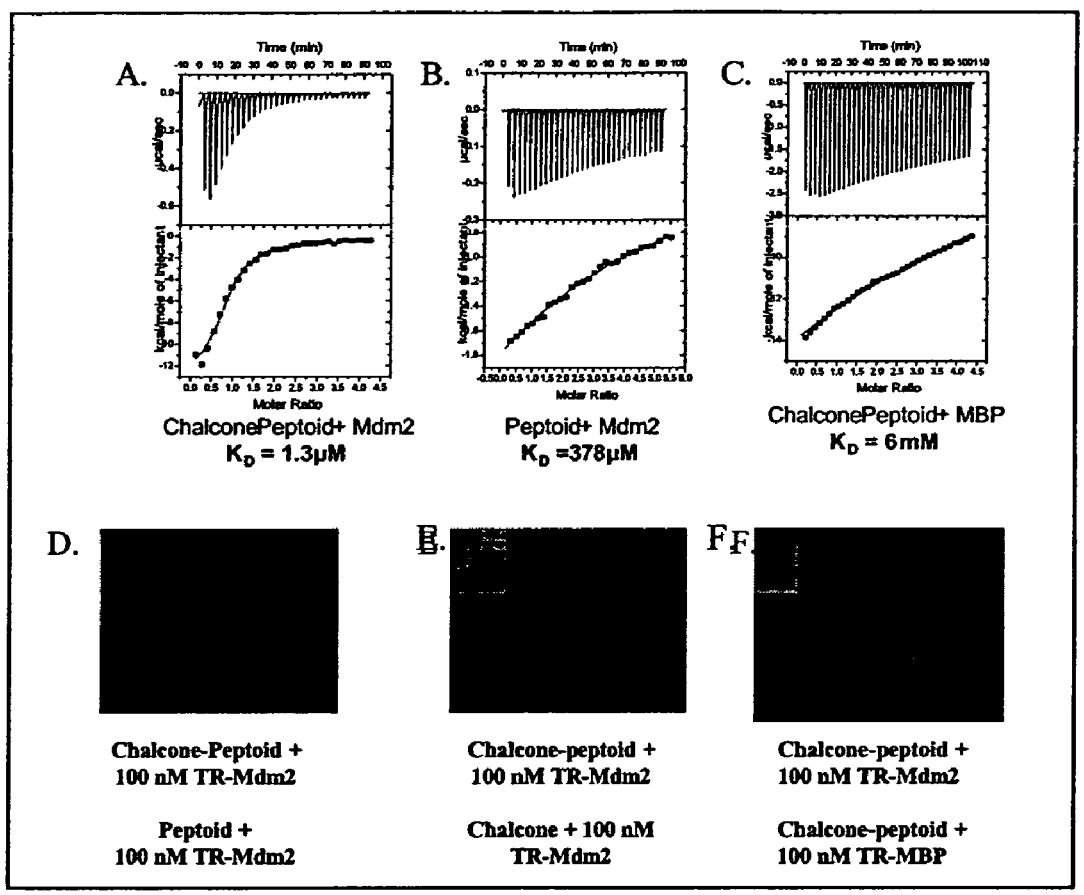
FIGS. 24A-24F illustrate the characterization of the binding properties of chimeric binding element general formula 2 and related compounds in solution and immobilized on Tentagel beads. Top: Isothermal titration calorimetry data for the titration of (FIG. 24A) chalcone-peptoid formula 2 and (FIG. 24B) the peptoid $NH_2$-Nlys-Npip-Nlys-Nser-Nlys-Nlys-Nlys-Nlys-Npip-Npip lacking the chalcone cap with MBP-Mdm2 and (FIG. 24C) chalcone-peptoid formula 2 with MBP alone. The equilibrium dissociation constants derived from these data are shown. Bottom (FIGS. 24D-24F): Tentagel beads displaying the compound indicated were incubated with the Texas Red-labeled proteins indicated and, after washing, the beads were mixed and photographed under a fluorescence microscope.

To probe the binding chemistry of chimeric binding ligand formula 2 on a solid support, which is more relevant to the issue of creating high affinity protein capture agents, Tenta-Gel beads were prepared that display either chalcone formula 1 alone, the 10 mer peptoid NH$_2$-Nlys-Npip-Nlys-Nser-Nlys-Nlys-Nlys-Nlys-Npip-Npip alone, or the chalcone-peptoid chimeric binding element of formula 2. In the experiment shown in FIG. 24D, the beads and the Texas Red-labeled proteins (100 nM) indicated in the figure were incubated under demanding buffer conditions (1M NaCl and 1% Tween-20 in the presence of a 100-fold excess of E. coli proteins), then washed thoroughly. Two populations of beads were then mixed in a 1:1 ratio and photographed under a fluorescence microscope to provide a direct comparison. FIG. 24D and FIG. 24E show the contrast between the solid phase MBP-Mdm2-binding affinity of the chalcone-peptoid formula 2 and the peptoid alone (FIG. 24D) and chalcone formula 1 alone (FIG. 24E), respectively. In each case one set of beads is much brighter than the other and subsequent Edman sequencing of the bright and dark beads confirmed that in both cases the bright beads displayed chimeric binding element formula 2. FIG. 24F shows the high level of contrast between the chalcone-peptoid-displaying beads that had been incubated with either labeled MBP-Mdm2 or MBP, again demonstrating specificity. These data agree qualitatively with the ITC results in that they show the chalcone-peptoid chimera has a higher affinity for Mdm2 than does either individual component of the chimera.

Figure 25:
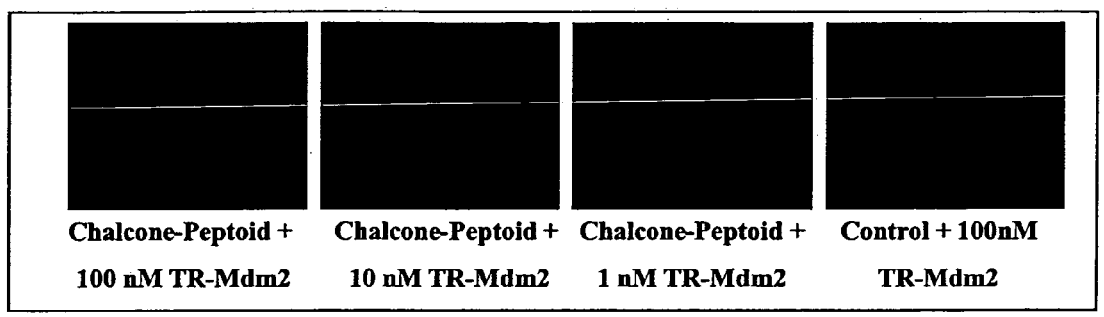
FIG. 25 is photomicrographs of Tentagel beads displaying the chimeric binding element of formula 2 after incubation with the indicated concentration of Texas Red-labeled MBP-Mdm2 protein followed by thorough washing.

To better judge the apparent affinity of the immobilized chalcone-peptide chimera formula 2 for labeled Mdm2, the study shown in FIG. 25 was conducted. In this case, a more typical biochemical buffer (150 mM NaCl and 0.1% detergent) was employed and the indicated concentration of labeled Mdm2 was mixed with 100-fold excess of E. coli proteins. After thorough washing, the beads were photographed in the fluorescence microscope using identical settings in each case. As can be seen in FIG. 24, capture of Mdm2 was apparent down to a protein concentration of 10 nM. The image at 1 nM Mdm2 was similar to that of a control bead displaying a different ligand.

A high affinity ubiquitin capture agent. For many proteins, even modest affinity lead compounds are not available. Therefore to evaluate a chimeric binding element from scratch, a high-affinity ubiquitin capture agent was generated by a two-step screening process in which a naïve peptide library was first screened under relatively mild conditions and then a hit from this screen was used to cap a chimeric binding element library that was then screened under more demanding conditions.

Figures 26A, 26B, 26C:
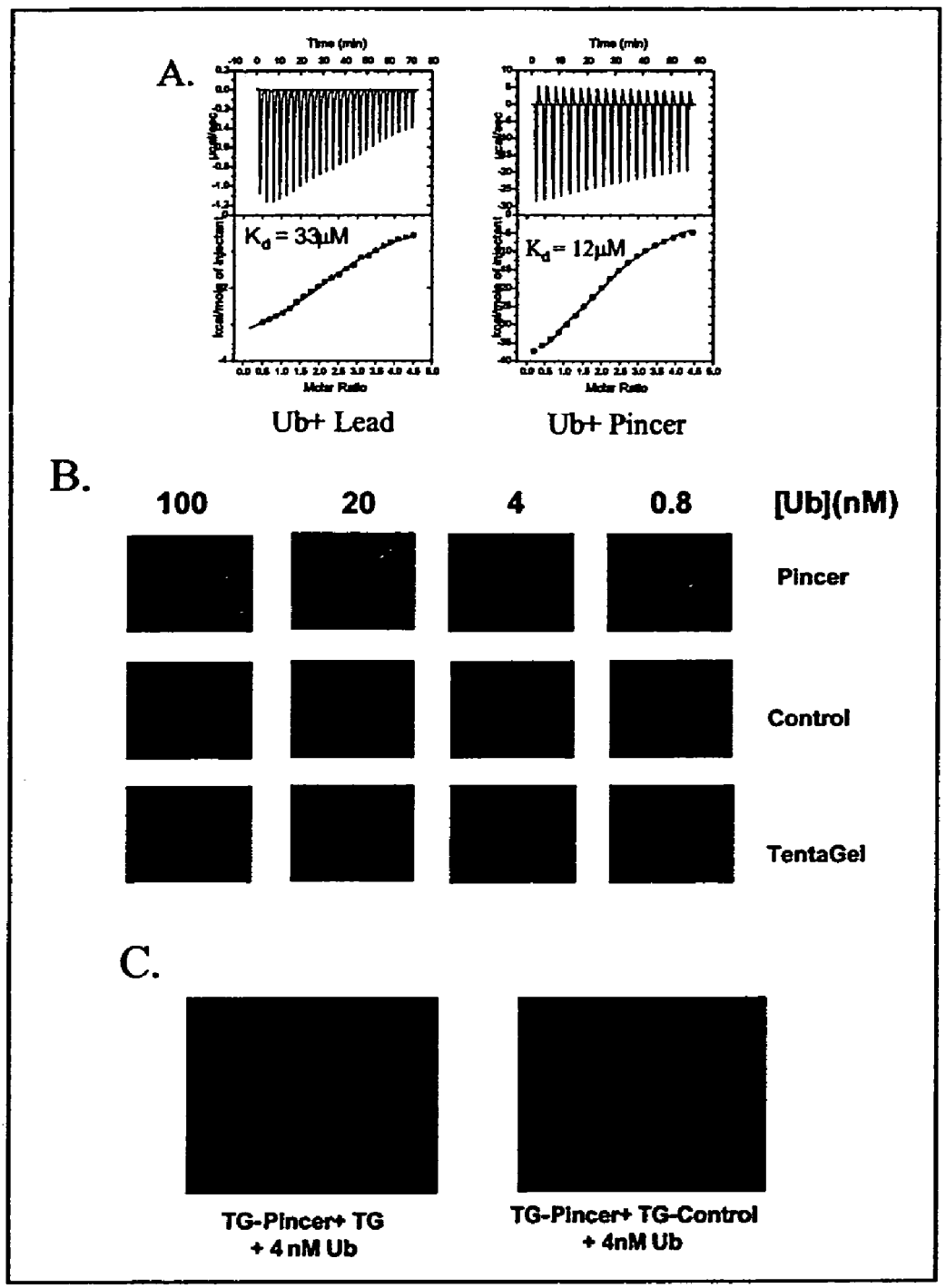
FIGS. 26A-26C illustrate the characterization of the solution and solid-phase binding properties of the ubiquitin lead peptide ($NH_2$-WGLRALESRWDRYYF) and the chimeric binding element ($NH_2$-WGLRALESRWDRYYF) and a control peptide.

In the first round a library of seven residue peptides was screened, resulting in the isolation of the peptide NH$_2$-RW-DRYYF. Titration experiments monitored by ITC revealed a K$_D$ of 33 (±5) μM for the peptide/ubiquitin complex (FIG. 26A). A new peptide library was then constructed on Tenta-Gel beads by split and pool synthesis of the form NH$_2$—X$_7$—S-RWDRYYF, where X represents a randomized position using the amino acids A, E, G, H, K, L, N, R, T, or W. A fraction of this library (=250,000 beads) was then incubated with fluorescently-labeled ubiquitin (200 nM) in the presence of a 10,000-fold excess of unlabeled proteins in a buffer containing 0.5 M NaCl and 0.5% Tween-20 detergent. In addition, a 1000-fold excess of synthetic lead peptide (NH$_2$-RWDRYYF) was also included in the buffer to block capture of ubiquitin by molecules that represent only a modest improvement over the lead peptide. Under these conditions, only three beads (0.0012% of the library) fluoresced well above background. The structure of the peptides was deduced by Edman sequencing. One of them (NH$_2$-WGLRALESRW-DRYYF) was resynthesized and purified. ITC experiments revealed that the chimeric binding element exhibited only a slight improvement over the lead in terms of its solution affinity for ubiquitin (FIG. 26A; K$_D$=12 (±4) μM).

To study the behavior of the ubiquitin-targeted chimeric binding element in capture assays, the peptide was synthesized on Tentagel and employed in "pull-down" assays. Beads displaying NH$_2$-WGLRALESRWDRYYF, a control peptide NH$_2$-HHRSHYKSMPRFMDYWEDL, or no peptide at all, were incubated with the indicated concentration of unlabeled ubiquitin in the presence of a 1000-fold excess of E. coli proteins (FIG. 26B). After thorough washing, the beads were then probed with Texas Red-labeled anti-ubiquitin-labeled polyclonal antibodies to visualize the bound protein. As shown in FIG. 26B, binding of ubiquitin by the chimeric binding element was very strong at 4 nM ubiquitin and easily detectable even at 0.8 nM ubiquitin. In all cases, the level of fluorescence from the chimeric binding element-displaying beads was much higher than from either set of control beads (see FIG. 26C for a direct comparison). Moreover, when the experiment was repeated with ubiquitin omitted from the solution, all of the beads exhibited the same low-level background signal (data not shown). While these binding assays are only semi-quantitative in nature, the data indicate that the functional dissociation constant of the immobilized chimeric binding element for ubiquitin is at least in the low nanomolar range.

Capture agents compared to solution ligands. The apparent binding affinity of the chimeric binding elements were considerably better when these compounds were immobilized than was the case free in solution. Of course, the bead-binding assays employed here are only semi-quantitative and in any case, one cannot compare apparent affinities to true solution $K_D$s rigorously. Furthermore, it is common to observe enhanced binding of a soluble analyte to a resin-bound compound since once the target molecule is bound, it finds itself in a local environment of very high ligand concentration, making escape from the environment of the bead unlikely. It may be that this effect can explain much of the apparent differences in binding affinity between the solution and immobilized Mdm2 chimeric binding element. Protein-binding compounds isolated from naive (i.e., non-chimeric binding element) libraries of peptides or peptoids generally form complexes with solution $K_D$s in the low to mid µM range. But when binding of the labeled target protein to the TentaGel-immobilized binding element is examined, binding can be detected routinely at a soluble protein concentration 10-100-fold lower than the solution $K_D$ value (unpublished results), even in cases where multivalent contacts are not possible. However, it seems unlikely that this mechanism could account completely for the much larger difference between these values observed in the ubiquitin study (solution $K_D$ of approximately 12 µM, but efficient capture at or below 1 nM). Another clear difference between the two chimeric binding elements is that the Mdm2-binding molecule formula 2 shows a large enhancement in its solution affinity over the lead chalcone formula 1, whereas the ubiquitin-binding chimeric binding element is only ≈3-fold better in solution than the lead peptide. Thus, a more likely explanation is that the immobilized ubiquitin-binding peptide NH$_2$-WGLRALES-RWDRYYF binds ubiquitin tightly because two different surface-bound molecules collaborate in an avidity-based event. Specifically, the lead peptide from one chimeric binding element molecule and the library-derived segment from another converge on a single molecule of ubiquitin. This is not surprising since the screen was carried out with resin-immobilized molecules and in fact is not a problem if the chimeric binding elements will be employed as immobilized protein capture agents.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,946,778
U.S. Pat. No. 5,582,981
U.S. Pat. No. 5,617,060
U.S. Pat. No. 5,719,060
U.S. Pat. No. 5,756,291
U.S. Pat. No. 5,780,610
U.S. Pat. No. 5,792,613
U.S. Pat. No. 5,840,867
U.S. Pat. No. 6,225,047
U.S. Pat. No. 6,329,209
U.S. Pat. No. 6,344,334
U.S. Pat. No. 6,461,515
U.S. Pat. No. 6,475,391
Alberts et al., In: *Molecular Biology of the Cell*, 3rd ed., Garland Publishing, Inc. NY, 1994.
Bachhawat-Sikder and Kodadek, *J. Amer. Chem. Soc.*, 125: 9550-9551, 2003.
Barany and Merrifield, In: *The Peptides*, Gross and Meienhofer (Eds.), Academic Press, NY, 1-284, 1979.
Blackwell et al., *Chem. Biol.*, 8:1167-1182, 2001.
Boeijen and Liskamp, *J. Tetrahedron Lett.*, 39:3589-3592, 1998.
Bottger et al., *Curr. Biol.*, 7:860-869, 1997.
Brocchini et al., *J. Am. Chem. Soc.*, 119:4553-4554, 1997.
Burkoth et al., *Chem. Biol.*, 9:647-654, 2002.
Chene et al., *J. Mol. Biol.*, 299:245-253, 2000.
Cho et al., *Bioorg Med Chem* 7, 1171-1179, 1999.
Clemons et al., *Chem. Biol.*, 8:1183-1195, 2001.
Colas et al., *Nature*, 380:548-550, 1996.
Cole et al., In: *Monoclonal Antibodies and Cancer Therapy*, Alan R. Liss, Inc., 77-96, 1985.
Cussac et al., *FASEB J.*, 13:31-38, 1999.
Eggers et al., *Biotechniques*, 17:516-525, 1994.
Eichler et al., *Medicinal Research Reviews* 15, 481-496, 1995.
Fairbrother et al., *Biochemistry*, 37:17754-17764, 1998.
Famlouk and Jenne, *Curr. Opin. Chem. Biol.*, 2:320-327, 1998.
Fancy and Kodadek, *Proc. Natl. Acad. Sci. USA*, 96:6020-6024, 1999.
Figliozzi et al., *Methods Enzymol.*, 267:437-447, 1996.
Gallop et al., *J. Med. Chem.*, 37(9):1233-1251, 1994.
Gordon et al., *J. Med. Chem.*, 37(10):1385-401, 1994.
Haab et al., *Genome Biol.*, 2(2):RESEARCH0004, 2001.
Han and Kodadek, *J. Biol. Chem.*, 275:4979-14984, 2000.
Heyduk, et al., *Method Enzymol.* 274:492-503, 1996.
Hornak, In: *The Basics of MRI*, 2002.
Huang et al., *Anal. Biochem.*, 294:55-62, 2001.
Huang, *J. Immunol. Methods*, 255:1-13, 2001.
Hunag et al. *Cancer Res.*, 62:2806-2812, 2002.
Huse et al., *Science*, 246:1275-1281, 1989.
Jhaveri et al., *Nature Biotechnol.*, 18:1293-1297, 2000.
Johnston et al., *Cell*, 50:143-146, 1987.
Kanemitsu, *Comb Chem High Throughput Screen*, 5(5):339-360, 2002.
Kiessling et al., *Curr. Opin. Chem. Biol.*, 4:696-703, 2000.
Kirshenbaum et al., *Proc. Natl. Acad. Sci. USA*, 95:4303-4308, 1998.
Kitov et al., *Nature*, 403:669-672, 2000.
Kitov et al., *J. Amer. Chem. Soc.*, 125:3284-3294, 2003.
Kodadek, *Chem. Biol.*, 8:105-115, 2001.

Kodadek, *Trends Biochem. Sci.,* 27(6):295-300, 2002.
Koehler et al., *J. Amer. Chem. Soc.,* 125:8420-8421, 2003.
Kohler and Milstein, *Nature,* 256:495-497, 1975.
Kozbor et al., *Immunology Today,* 4:72, 1983.
Kuruvilla et al., *Nature,* 416:653-657, 2002.
Kussie et al., *Science,* 2(74):948-953, 1996.
Lam et al., *Nature,* 354:82-84, 1991.
Leavitt and Freire, Curr. Opin. Struct. Biol., 11:560-566, 2001.
LePlae et al., *J. Amer. Chem. Soc.,* 124:6820-6821, 2002.
Lodish et al., In: *Molecular Cell Biology,* 4th ed., W.H. Freeman and Company, 2000.
Maly et al., *Proc. Natl. Acad. Sci. USA,* 97:2419-2424, 2000.
Melcher and Xu, *EMBO J.,* 20:841-851, 2001.
Merrifield, *Science,* 232(4748):341-347, 1986.
Merritt et al., *J. Amer. Chem. Soc.,* 124:8818-8824, 2002.
Needels et al., *Proc. Natl. Acad. Sci. USA,* 90:10700-10704, 1993.
Olejniczak et al., *J. Amer. Chem. Soc.,* 119:5828-5832, 1997.
Oliver et al., *Clinical Chemistry,* 44:2053-2060, 2000.
Olivos et al., *Org. Lett.,* 4:4057-4059, 2002.
Osborne et al., *Curr. Opin. Chem. Biol.,* 1: 5-9, 1997.
Ostergaard and Holm, Mol. Divers., 3:17-27, 1997.
PCT Appln. WO 00/56934
PCT Appln. WO 98/59360
PCT Appln. WO 99/51773
PCT Appln. WO98/59360
Pons et al., *Eur. J. Org. Chem.,* 853-859, 1998.
Radhakrishnan et al., *Cell,* 91:741-752, 1997.
Roberts and Szostak, *Proc. Natl. Acad. Sci. USA,* 94:12297-12302, 1997.
Schreiber, *Chem. Eng. News,* 81:51-61, 2003.
Schultz et al., *Cytometry,* 43:239-247, 2001.
Seethsnunan et al., *Nature Biotechnol.,* 19:336-341, 2001.
Shukery et al., *Science,* 274, 1531-1534, 1996.
Stemsdorf et al., *J. Biol. Chem.* 274(18):12555-66, 1999.
Stewart and Young, In: *Solid Phase Peptide Synthesis,* 2d. ed., Pierce Chemical Co., 1984.
Stoll et al., *Biochemistry,* 40:336-344, 2001.
Tam et al., *J. Am. Chem. Soc.,* 105:6442, 1983.
Terskikh et al., *Proc. Natl. Acad. Sci. USA,* 94:1663-1668, 1997.
Thompson and Ellman, *Chem. Rev.,* 96(1):555-600, 1996.
Thom et al., *J. Amer. Chem. Soc.,* 123:10113-10114, 2001.
Uno et al., *Terahedron Lett.,* 40:1475-1478, 1999.
Vaish et al., *Nature Biotech.,* 20:810-815, 2002.
Vignali, *J. of Immunol. Methods,* 243:243-255, 2000.
Walter et al., *Curr. Opin. Microbiol.,* 3:298-302, 2000.
Wender et al., *Proc. Natl. Acad. Sci. USA,* 97:13003-13008, 2000.
Wiese et al., *Clinical Chemistry,* 47:1451-1457, 2001.
Wilson et al., *Proc. Natl. Acad. Sci. USA,* 98:3750-3755, 2001.
Yang et al., *J. Amer. Chem. Soc.,* 121:589-590, 1999.
Zuckerman et al., *J. Med. Chem.,* 37:2678-2685, 1994.

What is claimed is:

1. A device for assessing the presence of at least a first target molecule in a sample comprising at least two distinct low-to-moderate affinity peptoid binding elements randomly distributed on a surface of and operatively coupled to a support, wherein a first peptoid binding element and a second peptoid binding element cooperatively bind the first target molecule with high affinity.

2. The device of claim 1, wherein a spacer is operatively coupled to the first peptoid binding element, the second peptoid binding element or both the first and second peptoid binding element.

3. The device of claim 1, wherein the first peptoid binding element is operatively coupled to a terminal monomer of the second peptoid binding element.

4. The device of claim 1, wherein the first peptoid binding element is operatively coupled to an internal monomer of the second peptoid binding element.

5. The device of claim 1, wherein a plurality of first peptoid binding elements are operatively coupled to the second peptoid binding element.

6. The device of claim 1, wherein the support is a cross-linked polymer bead or a chemically-modified glass slide.

7. The device of claim 1, further comprising at least a third and a fourth low-to-moderate affinity peptoid binding element that bind a second target molecule, the third and fourth peptoid binding element distributed on a surface of, and operatively coupled to, the support, wherein concomitant binding of the second target molecule to the third and fourth peptoid binding elements results in a high affinity interaction with the second target molecule.

8. The device of claim 7, wherein the third and fourth low affinity peptoid binding elements have distinct binding specificity as compared to each other.

9. The device of claim 7, wherein the third and fourth peptoid binding elements have distinct binding specificity as compared to the first and second low affinity peptoid binding elements.

10. The device of claim 7, wherein the first and second low affinity peptoid binding elements are segregated from the third and fourth low affinity peptoid binding elements.

11. The device of claim 7, wherein the first and second low affinity peptoid binding elements are segregated from the third and fourth low affinity peptoid binding elements on the surface of the support.

12. The device of claim 11, wherein the first and second peptoid binding elements, and the third and fourth peptoid binding elements, are distributed randomly on the surface of the support within their respective segregated areas.

13. A method of determining the presence of a target molecule in a sample comprising:
   (a) exposing the sample to a plurality of low-to-moderate affinity peptoid binding elements distributed on a surface of, and operatively coupled to a support, wherein concomitant binding of the target molecule to at least two of the binding elements results in a specific high affinity interaction with the target molecule; and
   (b) evaluating binding of the target molecule to the peptoid binding elements.

14. The method of claim 13, wherein binding is observed by spectroscopy.

15. The method of claim 14, wherein spectroscopy is fluorescent spectroscopy.

16. The method of claim 14, wherein spectroscopy is magnetic resonance imaging.

17. The method of claim 13, wherein the target molecule is a biological molecule or metabolite.

18. The method of claim 13, wherein the target molecule is a protein.

19. The method of claim 18, wherein the protein is a modified protein.

20. The method of claim 19, further comprising
   (c) comparing the binding in step b) with the binding of an unmodified protein.

* * * * *